United States Patent [19]

Mutsukado et al.

[11] Patent Number: 4,783,462
[45] Date of Patent: Nov. 8, 1988

[54] 3(2H)PYRIDAZINONE, AND ANTI-ALLERGIC AGENT CONTAINING IT

[75] Inventors: Motoo Mutsukado, Sakura; Keizo Tanikawa, Tokyo; Ken-ichi Shikada, Kuki; Ryozo Sakoda, Kashiwa, all of Japan

[73] Assignee: Nissan Chemical Industries Ltd., Tokyo, Japan

[21] Appl. No.: 833,607

[22] Filed: Feb. 27, 1986

[30] Foreign Application Priority Data

Feb. 27, 1985 [JP] Japan ................. 60-038559

[51] Int. Cl.$^4$ .................. C07D 237/06; A61K 31/50
[52] U.S. Cl. .................. 514/249; 544/238; 544/239
[58] Field of Search .................. 544/238, 239; 514/249

[56] References Cited

U.S. PATENT DOCUMENTS

| 4,115,575 | 9/1978 | Foei et al. | 544/239 |
| 4,360,672 | 6/1982 | Parg | 544/240 |
| 4,558,128 | 12/1985 | Ganelin et al. | 544/238 |

FOREIGN PATENT DOCUMENTS

| 784639 | 5/1968 | Canada . |
| 0088384 | 9/1983 | European Pat. Off. . |
| 0183212 | 6/1986 | European Pat. Off. . |
| 1670169 | 11/1970 | Fed. Rep. of Germany . |
| 1170970 | 12/1981 | U.S.S.R. . |
| 917849 | 2/1963 | United Kingdom . |

OTHER PUBLICATIONS

Chemical Abstracts, vol. 78, No. 11, Mar. 19, 1973, Columbus, OH., USA-Karklina, A.; Gudriniece, E. "Reactions of 1-phenyl-4-nitro-5-chloro-6-pyridazone", p. 466, Column 1, abstract-No. 72 037a & Latv. PSR Zinat. Akad. Vestis, Kim. Ser. 1972(6), 718-21.
Chemical Abstracts, vol. 97, No. 7, Aug. 16, 1982, Columbus, OH., USA-Matsuo, Toshiyasu et al. "Synthesis and Biological Activity of Pyridazinooxazines" p. 646, column 1, abstract-No. 55 755h & Chem. Pharm. Bull. 1982, 30(3), 832-42.
Chemical Abstracts, vol. 89, No. 3, Jul. 17, 1978, Columbus, OH., USA-Matsuo, Toshiyasu et al. "Pyridazinone derivatives" p. 656, column 1, abstract-No. 24 341a & Japan. Kokai 78 12, 880.
Bulletin De La Societe Chimique De France, vol. 9, No. 342, pp. 2124–2132, Paris, Fr: J. Bourdais: "Etudes en Série hétérocyclique: III-Action des amines aliphatiques et aryl–aliphatiques sur les dihalogéno-4,5(2-H)-pyridazinones—3".

Primary Examiner—Nicholas S. Rizzo
Attorney, Agent, or Firm—Oblon, Fisher, Spivak, McClelland & Maier

[57] ABSTRACT

A 3(2H)pyridazinone of the formula:

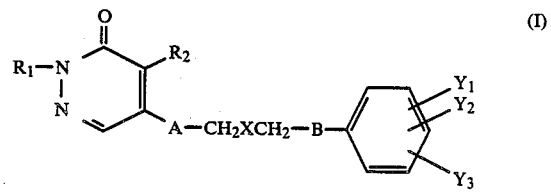

wherein $R_1$ is hydrogen or $C_1$-$C_5$ alkyl; $R_2$ is hydrogen, $C_1$-$C_8$ alkyl, chlorine or bromine; A is —$NR_3$— or —O—; X is —$(CH_2)_n$—, —$CH(OR_4)$—, —CO— or a single bond; when X is —$(CH_2)_n$— or a single bond, B is —O—, —S—, —NH—, —$OSO_2$—, or —OCO— or a single bond, when X is —$CH(OR_4)$—, B is —O—, —S—, —NH— or —$OSO_2$—, and when X is —CO—, B is —O— or —S—; and each of $Y_1$, $Y_2$ and $Y_3$ which may be the same or different, is hydrogen, $C_1$-$C_8$ alkyl, $C_2$-$C_8$ alkenyl, halogen,

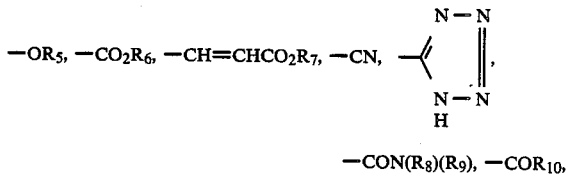

—$CON(R_8)(R_9)$, —$COR_{10}$, or two of $Y_1$, $Y_2$ and $Y_3$ together form

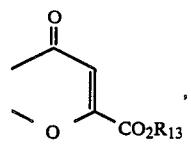

and a pharmaceutically acceptable salt thereof.

29 Claims, No Drawings

3(2H)PYRIDAZINONE, AND ANTI-ALLERGIC AGENT CONTAINING IT

The present invention relates to a 3(2H)pyridazinone which exhibits antagonism against slow reacting substance of anaphylaxis (SRS-A) which induces a contraction of bronchial smooth muscle, and thus is useful as an anti-allergic agent, a process for its preparation and a pharmaceutical composition containing it.

SRS-A is believed to be a principal etiologic substance which induces immediate allergy such as bronchial asthma or allergic rhinitis. Therefore, a medicine which controls the pharmacological effect of SRS-A, i.e. a SRS-A antagonist, is expected to be a useful anti-allergic agent.

However, a very few medicinal substances show antagonism against SRS-A, and no instance of their practical application has been reported.

As an example of a compound which is somewhat similar to the compound of the present invention, Canadian Patent No. 784,639 (hereinafter referred to as reference (a)) discloses 2-$C_1$-$C_8$-alkyl-4-chloro or bromo-5-benzylamino-3(2H)pyridazinone derivatives. However, the usefulness of the compounds disclosed in this reference (a) is restricted to a herbicide, and no mention is made as to its medical use or pharmacological activities.

As another example of a compound similar to the compound of the present invention, U.K. Patent No. 917,849 (Feb. 6, 1963) (reference (b)) discloses 2-alkyl-4-chloro-5-arylalkyloxy-3(2H)pyridazinones. However, this reference (b) contains no Examples disclosing the compounds of the present invention, and the usefulness of the compounds disclosed is restricted to a herbicide and no mention is made as to their medical use or pharmacological activities.

Likewise, as still another example of a compound similar to the compound of the present invention, published German Patent Application No. 1670169 (published on Nov. 5, 1970) (reference (c)) discloses 2-alkyl-4-chloro-5-arylalkylamino-3(2H)pyridazinones. This reference (c) discloses a process for the synthesis of pyridazinones including such compounds, their application for agricultural chemicals, their application as intermediates for medicines or dyestuffs, or their application as intermediates for various compounds. However, no mention is made to their pharmacological activities, and no specific examples are given for such compounds. Further, such compounds are not specifically described.

As still another example of a compound similar to the compound of the present invention, Chemical Abstract, 62, 2773b, (Bull. Soc. Chim, France, 1964 (9) p 2124–32) (reference d) discloses 2-methyl-4-chloro or bromo-5-benzylamino-3(2H)pyridazinones. This reference d is silent about medical use or pharmacological activities.

The present inventors have synthesized and studied various compounds for antagonistic activities against SRS-A, and it has been surprisingly found that 3(2H)pyridazinones of the formula I and their pharmaceutically acceptable salts exhibit antagonistic activities against SRS-A and thus are useful as an active ingredient for an anti-allergic agent.

Namely, the present invention provides a 3(2H)pyridazinone of the formula:

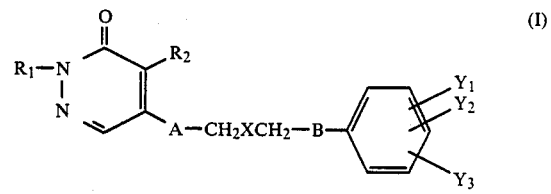

wherein $R_1$ is hydrogen or $C_1$-$C_5$ alkyl; $R_2$ is hydrogen, $C_1$-$C_8$ alkyl, chlorine or bromine; A is —$NR_3$— (wherein $R_3$ is hydrogen or $C_1$-$C_4$ alkyl) or —O—; X is —$(CH_2)_n$— (wherein n is an integer of 1 to 4), —CH(OR)— (wherein $R_4$ is hydrogen or $C_1$-$C_4$ alkyl), —CO— or a single bond; when X is —$(CH)_n$—(wherein n is as defined above) or a single bond, B is —O—, —S—, —NH—, —$OSO_2$—, or —OCO— or a single bond, when X is —CH($OR_4$)— (wherein $R_4$ is as defined above), B is —O—, —S—, —NH— or —O-$SO_2$13, and when X is —CO—, B is —O— or 13 S—; and each of $Y_1$, $Y_2$ and $Y_3$ which may be the same or different, is hydrogen, $C_1$-$C_8$ alkyl, $C_2$14 $C_8$ alkenyl, halogen, —$OR_5$ (wherein $R_5$ is hydrogen or $C_1$-$C_4$ alkyl), —$CO_2R_6$ (wherein $R_6$ is hydrogen or $C_1$-$C_4$ alkyl), —CH=$CHCO_2R_7$ (wherein $R_7$ is hydrogen or $C_1$-$C_4$ alkyl),

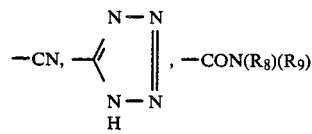

(wherein each of $R_8$ and $R_9$ which may be the same or different, is hydrogen or $C_1$-$C_4$ alkyl), —$COR_{10}$ [wherein $R_{10}$ is hydrogen, $C_1$-$C_5$ alkyl or

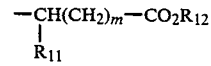

(wherein m is an integer of 0 to 3, $R_{11}$ is hydrogen or $C_1$-$C_3$ alkyl, and $R_{12}$ is hydrogen or $C_1$-$C_4$ alkyl)], or two of $Y_1$, $Y_2$ and $Y_3$ together form

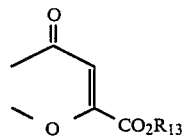

(wherein $R_{13}$ is hydrogen or $C_1$-$C_4$ alkyl), provided that when A is —NH— and both X and B are single bonds, $Y_1$, $Y_2$ and $Y_3$ are not simultaneously hydrogen, and a pharmaceutically acceptable salt thereof.

The present invention also provides a process for producing the pyridazinone of the formula I:

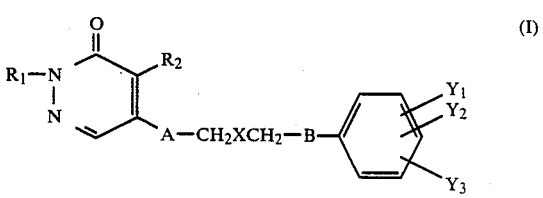

wherein $R_1$ is hydrogen or $C_1$-$C_5$ alkyl; $R_2$ is hydrogen, $C_1$-$C_8$ alkyl, chlorine or bromine; A is —$NR_3$— (wherein $R_3$ is hydrogen or $C_1$-$C_4$ alkyl) or —O—, X is —$(CH_2)_n$— (wherein n is an integer of 1 to 4), —CH(O$R_4$)— (wherein $R_4$ is hydrogen or $C_1$-$C_4$ alkyl) or a single bond; B is —O—, —S— or —NH—; and each of $Y_1$, $Y_2$ and $Y_3$ which may be the same or different, is hydrogen, $C_1$-$C_8$ alkyl, $C_2$-$C_8$ alkenyl, halogen, —$OR_5$ (wherein $R_5$ is hydrogen or $C_1$-$C_4$ alkyl), —$CO_2R_6$ (wherein $R_6$ is hydrogen or $C_1$-$C_4$ alkyl), —CH=CH$CO_2R_7$ (wherein $R_7$ is hydrogen or $C_1$-$C_4$ alkyl),

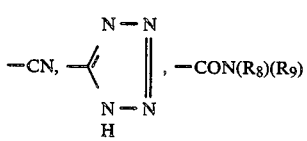

(wherein each of $R_8$ and $R_9$ which may be the same or different, is hydrogen or $C_1$-$C_4$ alkyl), —$COR_{10}$ [wherein $R_{10}$ is hydrogen, $C_1$-$C_5$ alkyl or

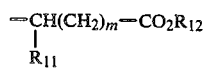

(wherein m is an integer of 0 to 3, $R_{11}$ is hydrogen or $C_1$-$C_3$ alkyl, and $R_{12}$ is hydrogen or $C_1$-$C_4$ alkyl)], or two of $Y_1$, $Y_2$ and $Y_3$ together form

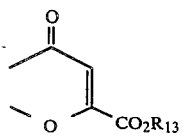

(wherein $R_{13}$ is hydrogen or $C_1$-$C_4$ alkyl), which comprises reacting a compound of the formula:

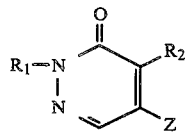

wherein $R_1$ and $R_2$ are as defined above, and Z is chlorine or bromine, with a compound of the formula:

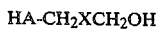

wherein A and X are as defined above, in the presence of a dehydrohalogenating agent to obtain a compound of the formula

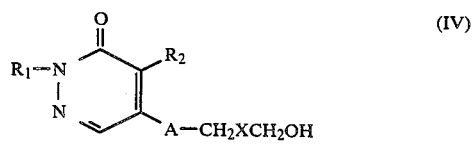

wherein $R_1$, $R_2$, A and X are as defined above, then reacting the compound of the formula IV with p-toluenesulfonyl chloride, methanesulfonyl chloride or a halogenating agent in the presence of a dehydrohalogenating agent to obtain a compound of the formula:

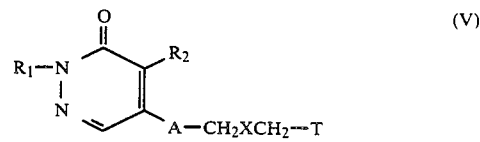

wherein $R_1$, $R_2$, A and X are as defined above, and T is

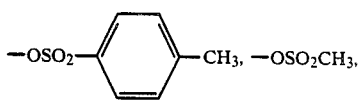

chlorine, bromine or iodine, and reacting the compound of the formula V with a compound of the formula VI:

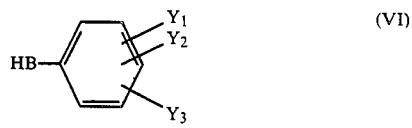

wherein B, $Y_1$, $Y_2$ and $Y_3$ are as defined above.

Now, the present invention will be described with reference to the preferred embodiments.

Specific examples of substituents $R_1$, $R_2$, A, X, B, $Y_1$, $Y_2$ and $Y_3$ will be described. However, it should be understood that the present invention is by no means restricted to such specific examples. In the following substituents, "n" means normal, "i" means iso, "sec" means secondary, and "t" means tertiary.

$R_1$ includes hydrogen, methyl, ethyl, n-propyl, i-propyl, n-butyl, i-butyl, sec-butyl, t-butyl, n-pentyl, i-pentyl and cyclopentyl.

$R_2$ includes chlorine, bromine, methyl, ethyl, n-propyl, i-propyl, n-butyl, i-butyl, sec-butyl, n-pentyl, n-hexyl, n-heptyl and n-octyl.

A includes oxygen, unsubstituted amino (—NH—), methylamino, ethylamino, n-propylamino, i-propylamino, n-butylamino, sec-butylamino and i-butylamino.

B includes oxygen, sulfur, sulfonyloxy, carbonyloxy, unsubstituted amino (—NH—) and a single bond.

X includes methylene, ethylene, propylene, butylene, a single bond, hydroxymethylene, methoxymethylene, ethoxymethylene, n-propoxymethylene, i-propoxymethylene, n-butoxymethylene, i-butoxymethylene, sec-butoxymethylene and oxomethylene

Each of $Y_1$, $Y_2$ and $Y_3$ which may be the same or different, includes hydrogen, methyl, ethyl, n-propyl, i-propyl, n-butyl, i-butyl, sec-butyl, n-pentyl, i-pentyl, sec-pentyl, n-hexyl, i-hexyl, sec-hexyl, n-heptyl, n-octyl, vinyl, 1-propenyl, allyl, 1-butenyl, 2-butenyl, 1-pentenyl, 1-hexenyl, 1-heptenyl, 1-octenyl, fluorine, chlorine, bromine, iodine, hydroxy, methoxy, ethoxy, n-propoxy, i-propoxy, n-butoxy, i-butoxy, sec-butoxy, carboxy, methoxycarbonyl, ethoxycarbonyl, n-propoxycarbonyl, i-propoxycarbonyl, n-butoxycarbonyl, i-butoxycarbonyl, sec-butoxycarbonyl, 2-carboxyethenyl, 2-methoxycarbonyl ethenyl, 2-ethoxycarbonyl ethenyl, 2-n-propoxycarbonyl ethenyl, 2-n-butoxycarbonyl ethenyl, cyano, lH-tetrazol-5-yl, carbamoyl, N-methylaminocarbonyl, N,N-dimethylaminocarbonyl, N-ethylaminocarbonyl, N,N-diethylaminocarbonyl, N-n-propylaminocarbonyl, N,N-di-n-propylaminocarbonyl, N-n-butylaminocarbonyl, carboxymethylcarbonyl, methoxycarbonylmethylcarbonyl, ethoxycarbonylmethylcarbonyl, 2-carboxyethylcarbonyl, 2-methoxycarbonylethylcarbonyl, 2-ethoxycarbonylethylcarbonyl, 1-methyl-2-carboxyethylcarbonyl, 1-methyl-2-methoxycarobnylethylcarbonyl, 1-carboxyethylcarbonyl, 1-methoxycarbonylethylcarbonyl, 1-carboxypropylcarbonyl, 1-methoxycarbonylpropylcarbonyl, formyl, acetyl, propionyl, butyryl, valeryl and hexyryl. Otherwise, two of $Y_1$, $Y_2$ and $Y_3$ together form

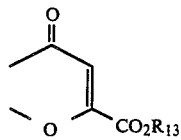

wherein $R_{13}$ is hydrogen, methyl, ethyl, n-propyl or n-butyl.

The compounds of the formula I of the present invention may be prepared in accordance with the following nineteen Processes 1 to 19.

Process 1

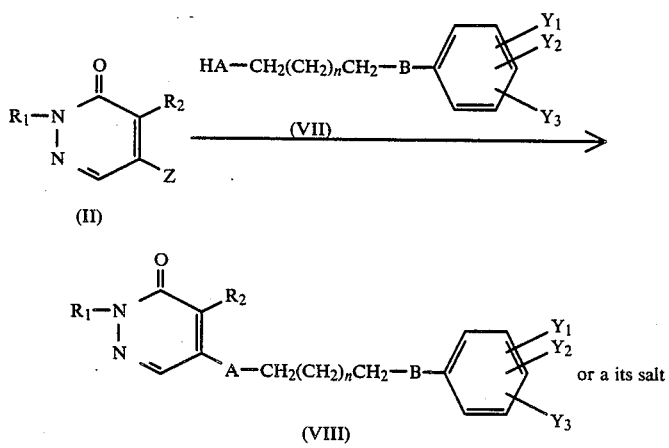

In the above formulas, $R_1$, $R_2$, A, $Y_1$, $Y_2$, $Y_3$ and n are as defined above with respect to the formula I, and Z is chlorine or bromine and B is —O—, —S— or a single bond. Namely, Process 1 is a process for producing a compound of the formula VIII by reacting a 3(2H)pyridazinone compound of the formula II with another starting material compound of the formula VII in an inert solvent in the presence of a dehydrohalogenating agent.

As the solvent, there may be employed an ether solvent such as isopropyl ether, tetrahydrofuran or 1,4-dioxane, an amide solvent such as N,N-dimethylformamide, N-methylacetamide or N-methylpyrrolidone, dimethylsulfoxide, an alcohol solvent such as methanol or ethanol, a hydrocarbon solvent such as toluene or benzene, pyridine or water, or a solvent mixture comprising two or more solvents selected from such solvents.

In the case where $R_2$ and Z are the same halogen atoms, good results are obtainable by using a solvent having high polarity such as water, an alcohol or an ether, or a solvent mixture thereof. The isolation and purification of the desired product can readily be accomplished by a usual method such as crystallization or silica gel chromatography.

As the dehydrohalogenating agent to be used, there may be employed an inorganic base such as potassium carbonate or sodium carbonate, and an organic base such as triethylamine or pyridine.

If necessary, an inter-phase transfer catalyst such as triethylbenzylammonium chloride may be added as a catalyst to the reaction system.

The reaction temperature may be within a range of from room temperature to the boiling point of the solvent used for the reaction system.

The molar ratio of the starting materials may optionally be set. However, preferred results are obtainable when the compound of the formula VII is used in an amount of from 1 to 5 mols relative to 1 mol of the pyridazinone derivative of the formula II.

There is no particular restriction as to the reation time. However, it is common to conduct the reaction for from 1 to 20 hours.

Process 2

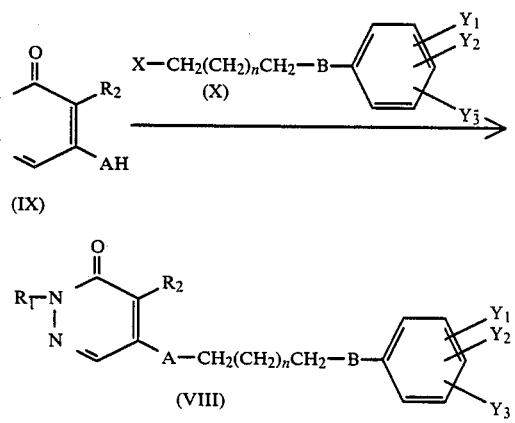

wherein $R_1$, $R_2$, A, $Y_1$, $Y_2$, $Y_3$ and n are as defined above with respect to the formula I, X is chlorine, bromine or iodine, and B is —O—, —S— or a single bond.

Namely, Process 2 is a process for producing a compound of the formula VIII by reacting a pyridazinone compound of the formula IX having —AH (wherein A is as defined above) at the 5-position, with a compound of the formula X in the presence of an organic or inorganic base. As the solvent, a usual solvent inert to the reaction may be employed. As the organic base, a usual amine such as triethylamine or pyridine may be mentioned. As the inorganic base, sodium carbonate or potassium carbonate may be mentioned. Further, a metal hydride such as sodium hydride may be employed, as the case requires. The reaction conditions and the isolation and purification of the desired product may be suitably selected in the same manner as in Process 1.

Process 3

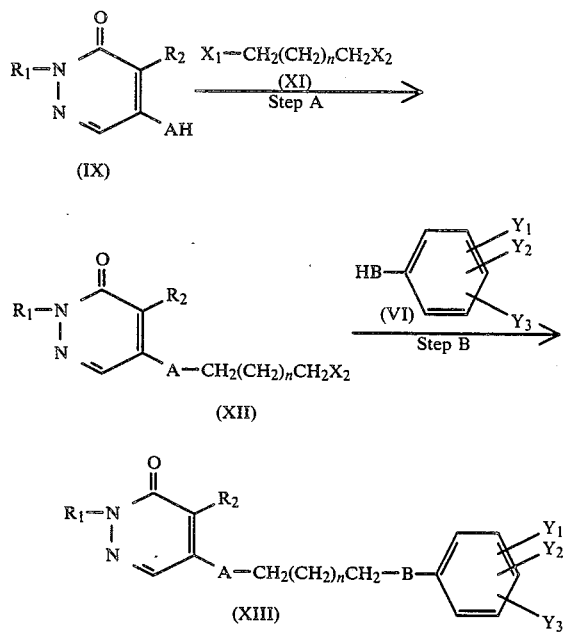

wherein $R_1$, $R_2$, A, $Y_1$, $Y_2$, $Y_3$ and n are as defined above with respect to the formula I, each of X and $X_2$ which may be the same or different, is chlorine, bromine or iodine, and B is —O—, —S— or —NH—.

Process 3 comprises Steps A and B. Namely, a compound of the formula IX is reacted with a compound of the formula XI in an inert solvent in the presence of a base to obtain a compound of the formula XII (Step A), and then the compound of the formula XII is reacted with a phenol, a thiophenol or an aniline of the formula VI in the presence of a dehydrohalogenating agent to obtain a compound of the formula XIII (Step B). The reaction conditions for Steps A and B and the isolation and purification of the desired product may suitably be selected in the same manner as in Process 1.

Process 4

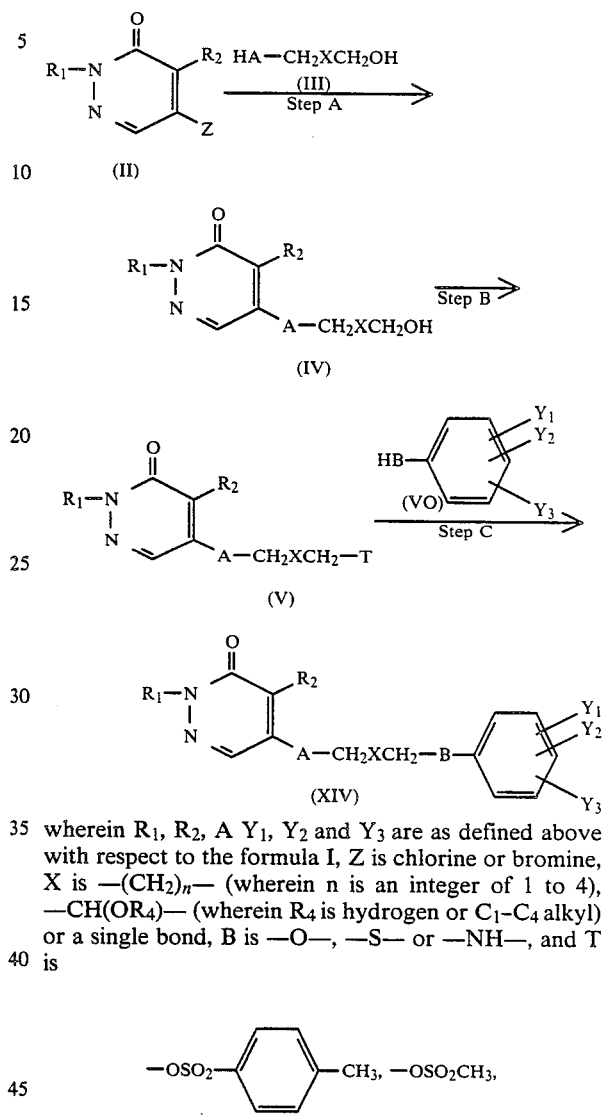

wherein $R_1$, $R_2$, A $Y_1$, $Y_2$ and $Y_3$ are as defined above with respect to the formula I, Z is chlorine or bromine, X is —$(CH_2)_n$— (wherein n is an integer of 1 to 4), —$CH(OR_4)$— (wherein $R_4$ is hydrogen or $C_1$-$C_4$ alkyl) or a single bond, B is —O—, —S— or —NH—, and T is

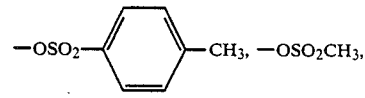

chlorine, bromine or iodine.

Process 4 comprises Steps A, B and C. Namely, Process 4 comprises reacting a compound of the formula II with a compound of the formula III in an inert organic solvent in the presence of a dehydrohalogenating agent to obtain a compound of the formula IV (Step A), then reacting this compound with p-toluenesulfonyl chloride, methanesulfonyl chloride or a halogenating agent as described hereinafter in the presence of a dehydrohalogenating agent to obtain a compound of the formula V (Step B), and reacting this compound with a phenol, a thiophenol or an aniline of the formula VI in an inert organic solvent in the presence of a dehydrohalogenating agent to obtain a compound of the formula XIV (Step C).

In Step A, the dehydrohalogenating agent which may be employed, includes an inorganic base such as potassium carbonate or sodium carbonate, and an organic base such as triethylamine or pyridine. There is no particular restriction as to the reaction temperature and the reaction time. However, it is common to conduct the reaction at a temperature within a range of from room temperature to the boiling point of the solvent for from 1 to 24 hours. The type of the solvent used, the molar ratio of the starting materials and the isolation and purification of the desired product may suitably be selected in the same manner as in Process 1.

In Step B, the dehydrohalogenating agent to be used together with p-toluenesulfonyl chloride or methansulfonyl chloride, includes an amine such as triethylamine or pyridine. Such an amine may also be employed as a solvent. Further, there may be employed a solvent which is inert to the reaction, for instance, a hydrocarbon solvent such as hexane, benzene, toluene or petroleum ether, an ether solvent such as ethyl ether, isopropyl ether or tetrahydrofuran, or a ketone solvent such as acetone or methyl ethyl ketone. With respect to the reaction temperature and the reaction time, it is common to conduct the reaction at a temperature of from $-15°$ to $40°$ C. for from 30 minutes to 2 hours. After the reaction, the desired product may be isolated by removing by-product amine salts, then drying the separated organic layer, distilling off the solvent, subjecting the oily substance or crystals thereby obtained to chromatography or crystallization. In a case where a halogenating agent is to be used, thionyl chloride, thionyl bromide, phosphorus trichloride or hydroiodic acid may be suitably employed. When a solvent is to be used, it is preferred to employ a solvent inert to the reaction, for instance, a hydrocarbon solvent such as benzene, hexane or petroleum ether, or an ether solvent such as ethyl ether or isopropyl ether. With respect to the reaction temperature and the reaction time, it is common to conduct the reaction at a temperature of from $-10°$ to $40°$ for from 30 minutes to 5 hours.

A compound of the formula V wherein T is iodine, can readily be obtained by reacting a compound of the formula V wherein T is chlorine, bromine, p-toluenesulfonyloxy or methanesulfonyloxy, with potassium iodide or sodium iodide in a suitable solvent.

The isolation of the desired product after the completion of the reaction can readily be carried out by distilling off the solvent, adding water and an organic solvent such as benzene or ethyl ether to the residue, vigorously shaking the mixture, drying and concentrating the organic layer thus separated, and subjecting the oily substance or crystals thereby obtained to chromatography or crystallization.

Process 5

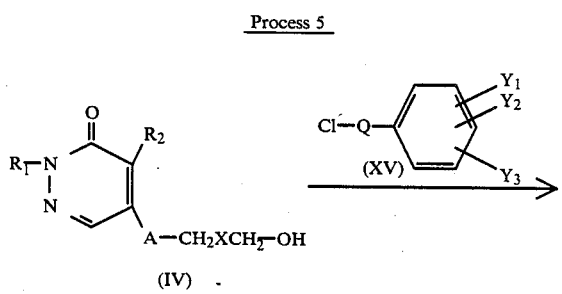

(IV)

-continued
Process 5

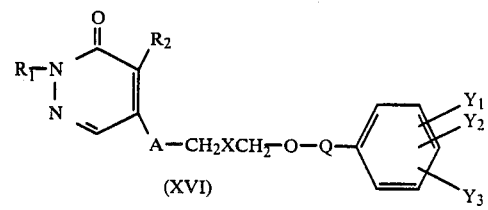

(XVI)

wherein $R_1$, $R_2$, A, $Y_1$, $Y_2$ and $Y_3$ are as defined above with respect to the formula I, X is $-(CH_2)_n-$ (wherein n is an integer of 1 to 4), $-CH(OR)-$ (wherein R is hydrogen or $C_1-C_4$ alkyl) or a single bond, and Q is $-CO-$ or $-SO_2-$.

Namely, Process 5 is a process for producing a compound of the formula XVI by reacting a 3(2H)pyridazinone compound of the formula IV obtained in Process 4, with an acid chloride of the formula XV in an inert solvent in the presence of a dehydrohalogenating agent such as triethyleamine or pyridine. As the solvent, there may be employed an ether solvent such as isopropyl ether, tetrahydrofuran or 1,4-dioxane, an amide solvent such as N,N-dimethylformamide, N,N-dimethylacetamide or N-methylpyrrolidone or a halogenated alkyl solvent such as chloroform or dichloromethane. The reaction temperature may be within a range of from $-15°$ C. to the boiling point of the solvent used, but is preferably from $-15°$ to $30°$ C.

The molar ratio of starting materials may optionally be set. However, it is preferred that the acid chloride of the formula XV is used in an amount of from 1 to 2 mols relative to 1 mol of the 3(2H)pyridazinone compound of the formula IV.

The isolation of the desired product after the completion of the reaction can readily be carried out by firstly removing the by-product amine hydrochlorides, adding water to the residue, vigorously shaking the mixture, drying and concentrating the organic layer thus separated, and subjecting the oily substance or crystals thereby obtained to chromatography or crystallization.

Process 6

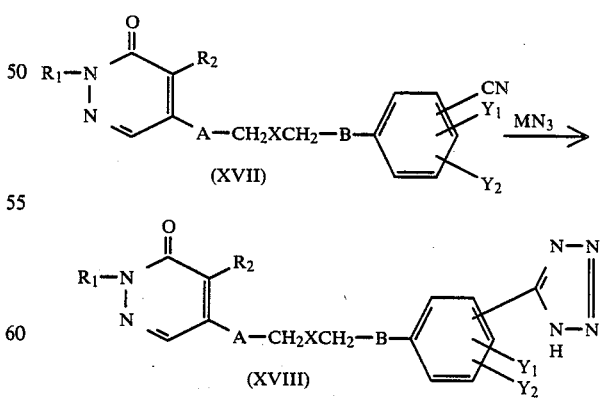

(XVIII)

wherein $R_1$, $R_2$, A, X, $Y_1$ and $Y_2$ are as defined above with respect to the formula I, and B is $-O-$, $-S-$, $-NH-$ or a single bond.

Namely, Process 6 is a process for producing a compound of the formula XVIII having a

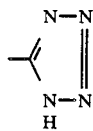

group by reacting a compound of the formula XVII having a —CN group, with a hydrazoate of the formula MN (wherein M is an alkali metal).

As the hydrazoate to be used for the reaction, there may be employed an alkali metal salt of hydrazoic acid such as lithium azide, sodium azide or potassium azide.

These hydrazoates may be used alone. Otherwise, for instance, sodium azide may be used in combination with a Lewis acid such as aluminum chloride, stannic chloride, zinc chloride or titanium tetrachloride, or with ammonium chloride. Among these combinations, a combination of sodium azide and ammonium chloride is particularly preferred.

It is usually preferred to conduct the reaction in an organic solvent. As such a solvent, there may be mentioned a hydrocarbon solvent such as benzene, toluene or petroleum ether, an ether solvent such as tetrahydrofuran, dioxane, ethylene glycol or dimethyl ether, an amide solvent such as dimethylformamide or formamide and dimethylsulfoxide. There is no particular restriction to the reaction conditions such as the reaction temperature and the reaction time. However, it is common to conduct the reaction at a temperature of from 50° to 150° C. for from 1 hour to two days.

When a salt of hydrazoic acid is used as one of the starting materials in the reaction of the present invention, the resulting compound of the formula XVIII will be in the form of a salt corresponding to the salt of hydrazoic acid used for the reaction due to the acidity of the tetrazole ring. By treating this salt with an acid i.e. a mineral acid such as hydrochloric acid or sulfuric acid, it is pssible to readily obtain the desired compound of the formula XVIII having a free tetrazole ring. By reacting the compound of the formula XVIII with sodium hydroxide, potassium hydroxide, an organic amine such as methylamine or L-lysine, or ammonia in a suitable solvent by a conventional method such as mixing or heating, it is possible to obtain an alkali metal salt, an organic amine salt or an ammonium salt of the compound of the formula XVIII.

Process 7

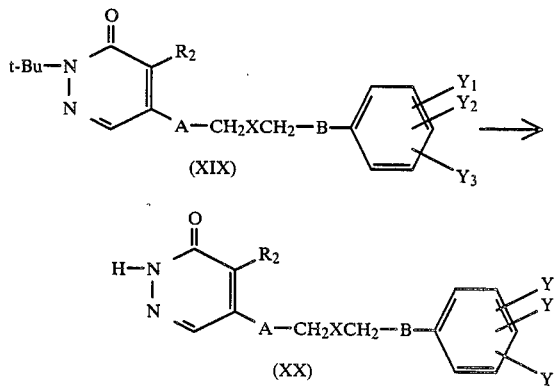

wherein $R_2$, A, $Y_1$, $Y_2$ and $Y_3$ are as defined above, X is —$(CH_2)_n$— (wherein n is an integer of 1 to 4), —CH-(OR$_4$)— (wherein $R_4$ is hydrogen or $C_1$-$C_4$ alkyl) or a single bond, and B is —O—, —S—, —NH— or a single bond.

Namely, Process 7 is a process for producing a compound of the formula XX by treating a compound of the formula XIX having a tertiary butyl group as a protective group at the 2-position, with a mineral acid such as sulfuric acid, hydrochloric acid or hydrobromic acid to remove the tertiary butyl group. As a solvent to be used, there may be employed an alcohol solvent, a hydrocarbon solvent, a halogenated hydrocarbon solvent or water, or a solvent mixture of such solvents.

In this process, when $Y_1$, $Y_2$ or $Y_3$ is a —CN group, it is possible to convert the —CN group to an ester or carboxylic acid group of the formula —$CO_2R_6$ simultaneously with the removal of the protective group by using as a solvent a compound of the formula $R_6OH$ (wherein $R_6$ is hydrogen or $C_1$-$C_4$ alkyl) in the above-mentioned mineral acid. The reaction conditions such as the reaction temperature or reaction time are not critical, but it is common to conduct the reaction at a temperature around the boiling point of the solvent used, for from 1 hour to 2 days. The isolation of the desired product after the completion of the reaction may be carried out by distilling off the solvent, adding an organic solvent such as ethyl acetate or chloroform and water to the residue, shaking the mixture, drying and concentrating the organic layer thereby separated, and purifying the substance thus obtained, by recrystallization or chromatography.

Further, in a case where a substituents susceptible to decomposition by a mineral acid, the same object can be achieved by employing a conventional hydrogenation method, as the case requires.

Process 8

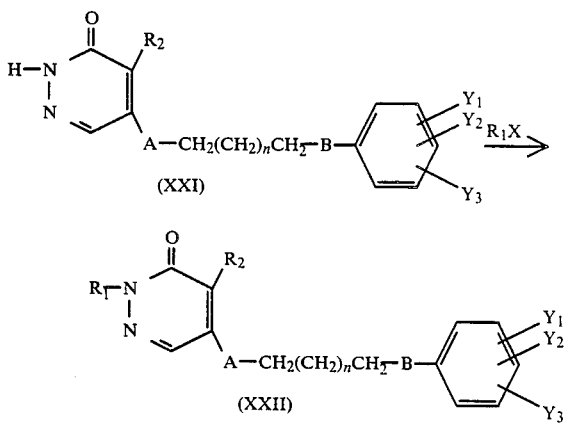

wherein $R_1$ is $C_1$-$C_5$ alkyl, B is —O—, —S— or a single bond, and $R_2$, A, n, $Y_1$, $Y_2$ and $Y_3$ are as defined above with respect to the formula I.

Namely, Process 8 is a process for producing a 3(2H)pyridazinone of the formula XXII with the 2-position alkylated, by reacting a compound of the formula XXI with an alkyl halide of the formula $R_1X$ in the presence of a base. As the solvent, there may be employed an ether solvent such as isopropyl ether, tetrahydrofuran or 1,4-dioxane, an amide solvent such as N,N-dimethylformamide, N-methylacetamide or N-methylpyrrolidone, dimethylsulfoxide, an alcohol solvent such as methanol or ethanol, a hydrocarbon solvent such as toluene or benzene, a ketone solvent such as acetone or methyl ethyl ketone, or water.

The purification of the desired product may readily be accomplished by crystallization or silica gel chromatography.

As the base, there may be employed an inorganic base such as potassium carbonate or sodium carbonate, or an organic base such as triethylamine or pyridine. An inter-phase transfer catalyst such as triethylbenzyl ammonium chloride may be added as a catalyst to the reaction system, as the case requires. The reaction temperature may be within a range of from room temperature to the boiling point of the solvent used for the reaction system.

The molar ratio of the starting materials may optionally be set. However, good results can be obtained when the compound of the formula $R_1X$ is used in an amount of from 1 to 5 mols relative to 1 mol of the pyridazinone derivative of the formula XXI.

Process 9

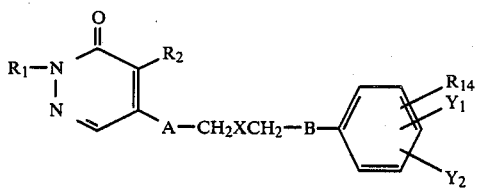
(XXIII)

wherein $R_1$, $R_2$, A, X, $Y_1$ and $Y_2$ are as defined above with respect to the formula I, B is —O—, —S—, —NH— or a single bond, and $R_{14}$ is —$CO_2R_6$ (wherein $R_6$ is $C_1$-$C_4$ alkyl) or —CN.

Namely, Process 9 is a process for converting a compound of he formula XXIII to the corresponding carboxylic acid or its salt by hydrolyzing $R_{14}$ (wherein $R_{14}$ is as defined above) of the compound of the formula XXIII under an acidic or alkaline condition. As the solvent for the reaction, there may be employed water or an organic solvent such as ethanol, methanol, tetrahydrofuran or dioxane, or a mixture of water with such organic solvents. There is no particular restriction as to the reaction temperature, the reaction time or other reaction conditions. However, it is common to conduct the reaction at a temperature of from 10° to 100° C. for from 1 to 5 hours.

The isolation of the desired product after the completion of the reaction may be conducted by separating and purifying the precipitated crystals or freed oily substance by recrystallization or silica gel chromatography.

Process 10

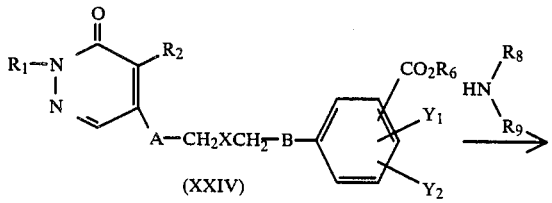
(XXIV)

-continued
Process 10

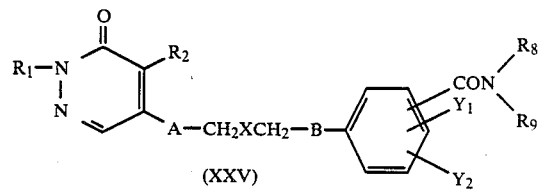
(XXV)

wherein $R_1$, $R_2$, $R_6$, $R_8$, $R_9$, A and X are as defiend above with respect to the formula I, and B is —O—, —S— or a single bond.

Namely, Process 10 is a process for producing an amide compound of the formula XXV by reacting a compound of the formula XXIV with an amine of the formula

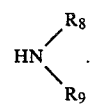

When the starting material compound of the formula XXIV is an ester (wherein $R_6$ is $C_1$-$C_4$ alkyl), the desired product can readily be obtained by a usual aminolysis or ammonolysis by an addition of an amine or by an addition of ammonia.

It is usually preferred to conduct the reaction in an organic solvent. As such an organic solvent, an alcohol solvent such as ethanol or methanol, or an ether solvent such as tetrahydrofuran or dioxane, may be mentioned. Further, it is possible to use a mixture of such an organic solvent with water. There is no particular restriction as to the reaction conditions such as the reaction temperature or the reaction time. However, it is common to conduct the reaction at a temperature of from 50° to 150° C. for from 1 to 15 hours.

When the starting material is a carboxylic acid (wherein $R_6$ is hydrogen), the desired product can readily be obtained by reacting it with an amine in the form of an acid halide or in the presence of a dehydration condensation agent, or heating an amine salt of the corresponding carboxylic acid.

The isoation of the desired product after the completion of the reaction, can readily be carried out by collecting crude crystals of the desired product precipitated in the reaction system by filtration, followed by recrystallization, or in a case where no crystals precipitate, by distilling off the solvent, adding an organic solvent, i.e. a usual solvent for extraction such as ethyl acetate or chloroform, and water, vigorously shaking the mixture, concentrating the organic layer thereby obtained, and subjecting the resulting crude crystals to recrystallization or silica gel chromatography.

Process 11

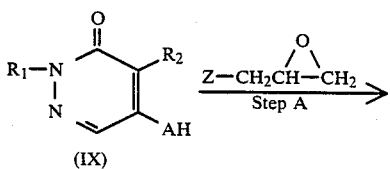
(IX)

-continued
Process 11

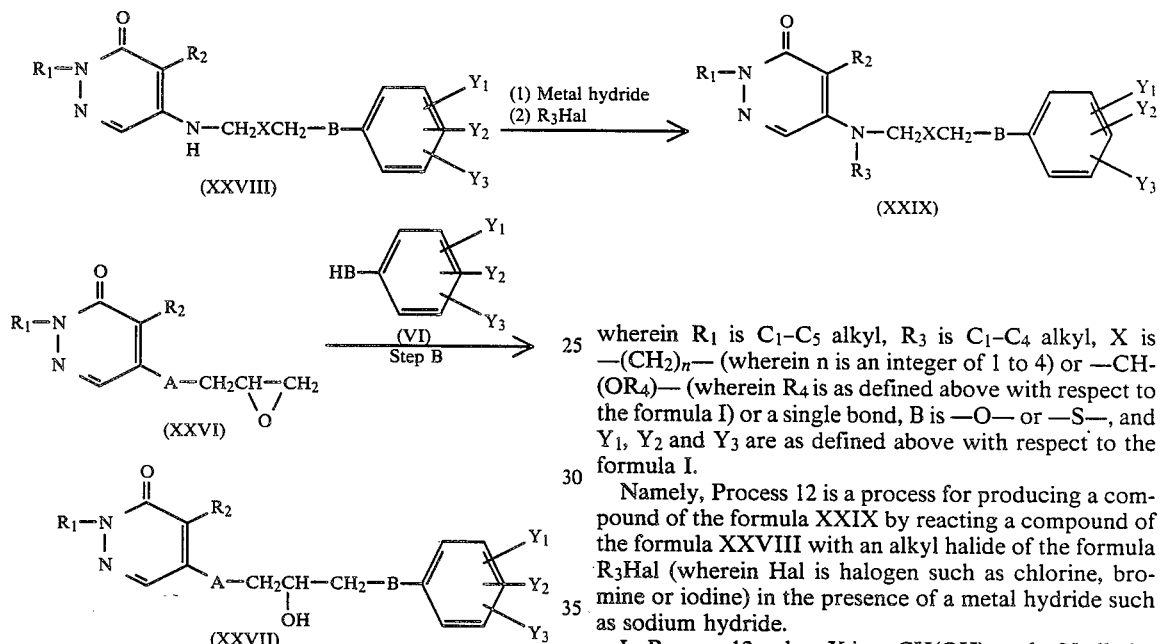

wherein $R_1$, $R_2$, A, $Y_1$, $Y_2$ and $Y_3$ are as defined above with respect to the formula I, Z is chlorine or bromine, and B is —O—, —S— or —NH—.

Namely, Process 11 comprises a step of reacting a compound of the formula IX as used in Process 2, with an epihalohydrin of the formula

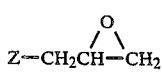

in an inert solvent in the presence of a base to obtain an epoxy compound of the formula XXVI (Step A) and a step of reacting the compound of the formula XXVI with a phenol, a thiophenol or an aniline in the presence of a basic catalyst to obtain a compound of the formula XXVII (Step B).

The reaction conditions for Step A and the isolation of the desired product may be similar to those in Process 1. However, in a case where A is —NR$_3$— (wherein R$_3$ is as defined above with respect to the formula I), it is preferred to use an aprotic solvent such as dimethylformamide, dimethylacetamide or tetrahydrofuran as the solvent and a metal hydride such as sodium hydride as the dehydrohalogenating agent.

With respect to the reaction conditions for Step B, the solvent may be the same as in Step A. However, the reaction can adequately be conducted in the absence of a solvent. As the basic catalyst, it is preferred to use a usual inorganic base such as sodium carbonate or potassium carbonate, or a quaternary ammonium base such as trimethylbenzylammoniumhydroxide. There is no particular restriction as to the reaction temperature and the reaction time. However, it is common to conduct the reaction at a temperature of from 20° C. to the boiling point of the solvent used, for from 20 minutes to two hours.

Process 12 wherein $R_1$ is $C_1$-$C_5$ alkyl, $R_3$ is $C_1$-$C_4$ alkyl, X is —(CH$_2$)$_n$— (wherein n is an integer of 1 to 4) or —CH(OR$_4$)— (wherein R$_4$ is as defined above with respect to the formula I) or a single bond, B is —O— or —S—, and $Y_1$, $Y_2$ and $Y_3$ are as defined above with respect to the formula I.

Namely, Process 12 is a process for producing a compound of the formula XXIX by reacting a compound of the formula XXVIII with an alkyl halide of the formula R$_3$Hal (wherein Hal is halogen such as chlorine, bromine or iodine) in the presence of a metal hydride such as sodium hydride.

In Process 12, when X is —CH(OH)—, the N-alkylation and the O-alkylation are simultaneously conducted by using at least 2 mols of each of the alkyl halide and the metal hydride relative to 1 mol of the compound of the formula XXVIII, whereby a compound of the formula:

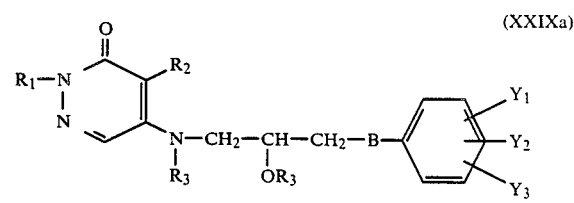

can be obtained in good yield.

When at least one of $Y_1$, $Y_2$ and $Y_3$ is

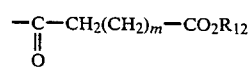

(wherein m and R$_{12}$ are as defined above with respect to the formula I), the N-alkylation and the alkylation of the active methylene of

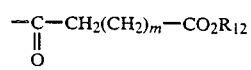

take place simultaneously, whereby a compound of the formula:

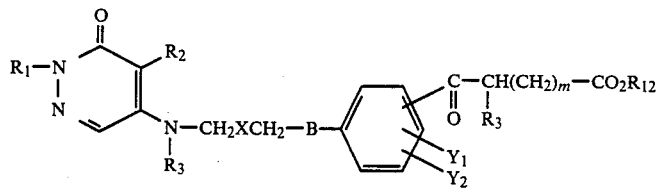

(XXIXb)

can be obtained.

The process can be conducted by reacting the compound of the formula XXVIII firstly with the metal hydride in an organic solvent, and then with the alkyl halide of the formula $R_3Hal$. As the organic solvent, an inert organic solvent such as dimethylformamide, tetrahydrofuran or diethyl ether is preferably employed. The reaction with the alkali metal hydride is conducted preferably at a temperature within a range of from $-15°$ to $10°$ C., and the reaction with the alkyl halide is conducted preferably a a temperature within a range of from $0°$ to $80°$ C. The isolation and purification of the desired product after the completion of the reaction, can be conducted in the same manner as in Process 8.

wherein $R_1$ is $C_1$-$C_5$ alkyl, $R_4$ is $C_1$-$C_4$ alkyl, B is —O— or —S—, X is chlorine, bromine or iodine, and $R_2$, A, $Y_1$, $Y_2$ and $Y_3$ are as defined above with respect to the formula I.

Process 13 is a process for producing a compound of the formula XXXI by reacting a compound of the formula XXX with an alkyl halide of the formula $R_4X$ (wherein $R_4$ and X are as defined above) to convert the —OH group in the side chain to a —OR$_4$ group.

The reaction conditions and the isolation of the desired product may be similar to those in Process 8.

Process 14

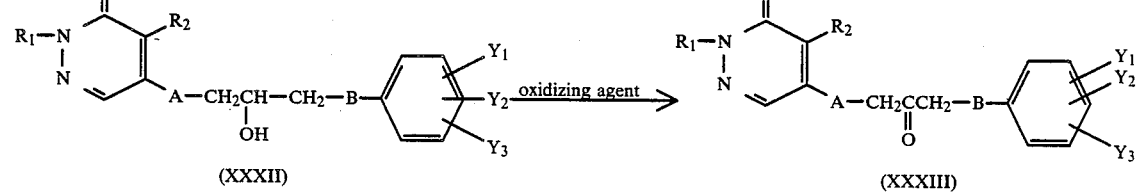

wherein $R_1$, $R_2$, A, $Y_1$, $Y_2$ and $Y_3$ are as defined above with respect to the formula I, and B is —O— or —S—.

Namely, Process 14 is a process for producing a compound of the formula XXXIII by reacting a compound of the formula XXXII having a —OH group with an oxidizing agent commonly employed for organic reactions to convert the >CHOH group to a >CO group.

For the oxidation, any oxidation method commonly employed for the oxidation of alcohols, such as Jone's oxidation, Collin's oxidation, Moffat oxidation (dimethylsulfoxide/N,N'-dicyclohexylcarbodimide) or a modification thereof (dimethylsulfoxide/acetic anhydride or trifluoroacetic anhydride) may be employed. However, it is preferred to employ a suitable oxidation method among these methods depending upon the types of the substitutents $Y_1$, $Y_2$ and $Y_3$.

The isolation and purification of the desired product after the completion of the reaction may readily be conducted by adding water and a usual organic solvent for extraction to the reaction solution, shaking the mixture, drying and concentrating the organic layer thereby obtained, and subjecting the crude crystals or oily substance thus obtained, to recrystallization or silica gel chromatography.

Process 13

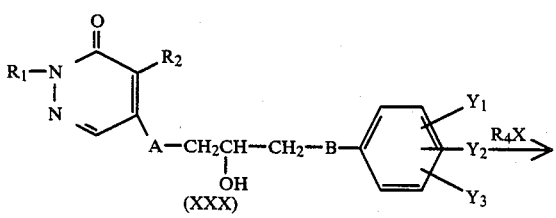

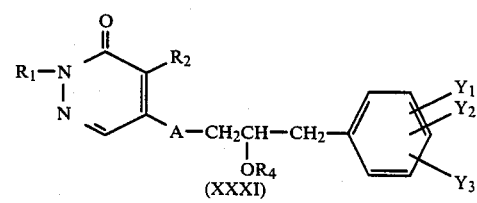

Process 15

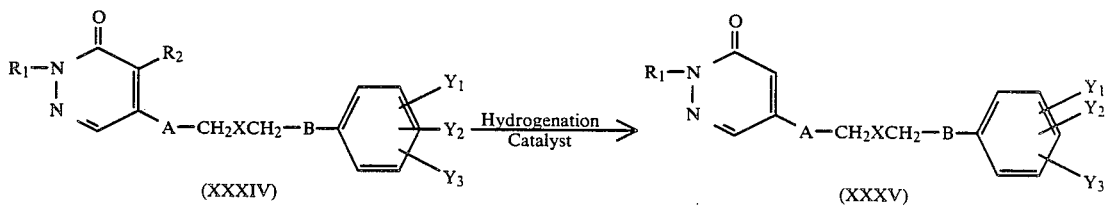

wherein $R_1$, A, X, B, $Y_1$, $Y_2$ and $Y_3$ are as defined above with respect to the formula I, and $R_2$ is chlorine or bromine.

Namely, Process 15 is a process for producing a compound of the formula XXXV by subjecting a compound of the formula XXXIV having chlorine or bromine at the 4-position of the pyridazinone, to usual hydrogenation (i.e. common hydrogenation wherein palladium or platinum is used as a catalyst) for dehalogenation.

As the organic solvent, a usual inert solvent may be employed, but an alcohol solvent such as ethanol or methanol is particularly preferred.

It is possible to facilitate the reaction by an addition of an organic amine such as triethylamine or pyridine. The reaction temperature may be within a range of from 10° C. to the boiling point of the organic solvent used, but is preferably within a range of from 20° to 60° C. The isolation of the desired product after the completion of the reaction can readily be conducted by firstly filtering off the catalyst, concentrating the filtrate, dissolving the residue in a usual solvent for extraction such as ethyl acetate, chloroform or benzene, adding water or an aqueous hydrochloric acid solution (about 10%), shaking the mixture, drying and concentratiing the organic layer, subjecting the crude crystals or oily substance thereby obtained, to recrystallization or silica gel chromatography.

tion with malonic acid or a malonic acid monoester of the formula

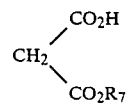

in the presence of an organic amine catalyst such as piperidine or pyrrolidine or an inorganic basic catalyst such as potassium acetate or sodium acetate to convert the —CHO group to a —CH=CHCO$_2$R$_7$ group.

As the organic solvent, a solvent inert to the reaction, for instance, a hydrocarbon solvent such as benzene or toluene, an ether solvent such as 1,4-dioxane or tetrahydrofuran, an alcohol solvent such as ethanol or propanol, or an amine solvent such as pyridine or triethylamine, may be employed. The reaction temperature and the reaction time may be set within wide ranges. Namely, the reaction may be conducted at a temperature of from 50° to 50° C. for from 5 to 24 hours.

The isolation and purification of the desired product after the completion of the reaciton, can readily be carried out by firstly acidifying the reaction solution with a mineral acid such as hydrochloric acid, extracting it with a suitable organic solvent such as ethyl acetate, chloroform or ethyl ether, distilling off the organic

Process 16

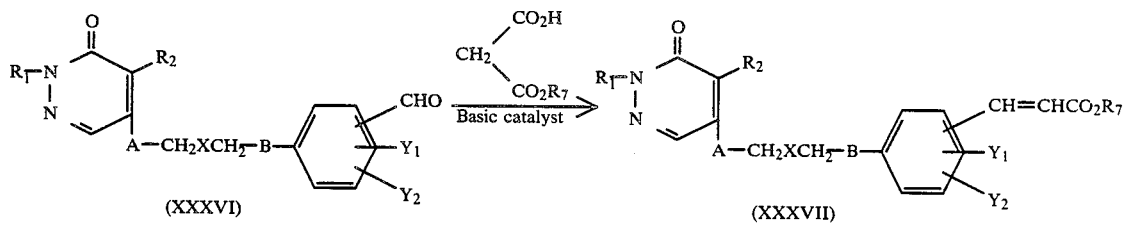

wherein $R_1$, $R_2$, $R_7$, A, X, $Y_1$ and $Y_2$ are as defined above, and B is —O— or —S—.

Namely, Process 16 is a process for producing a compound of the formula XXXVII by subjecting a compound of the formula XXXVI to a condensation reacsolvent, and subjecting the residue thereby obtained, to crystallization or silica gel chromatography.

Process 17

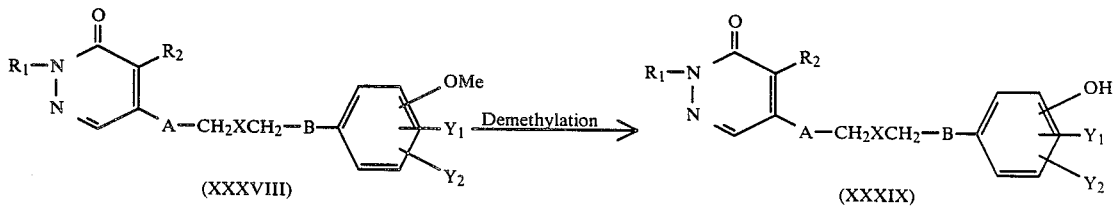

wherein $R_1$, $R_2$, A, X, $Y_1$ and $Y_2$ are as defined above with respect to the formula I, and B is —O— or —S—.

Namely, Process 17 is a process for producing a compound of the formula XXXIX by demethylating a compound of the formula XXXVIII to convert the —OMe group to a —OH group.

As the demethylating agent, it is preferred to use a reagent obtained by a combination of a hard acid and a soft base, such as aluminum chloride/di-n-propylsulfide.

As the solvent, a solvent inert to the reaction, such as dichloromethane or dichloroethane, is preferred. The reaction temperature and the reaction time may be set within wide ranges. However, it is common to conduct the reaction at a temperature of from 0° to 30° C. for from 5 to 48 hours.

-continued
Process 19

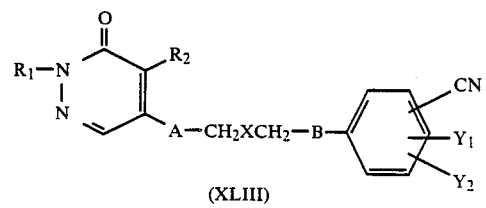

(XLIII)

wherein $R_1$, $R_2$, A, X, B, $Y_1$ and $Y_2$ are as defined above with respect to the formula I.

Process 18

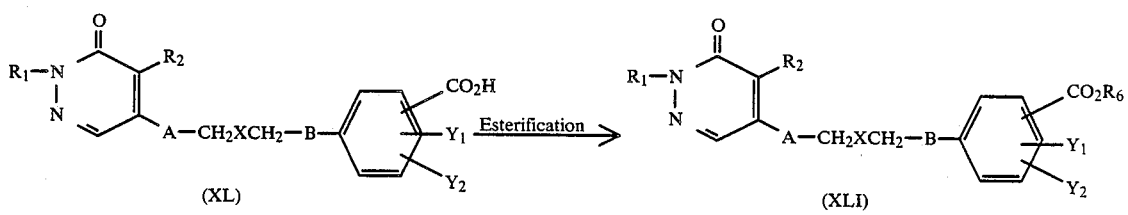

(XL)  (XLI)

wherein $R_1$, $R_2$, A, X, B, $Y_1$ and $Y_2$ are as defined above with respect to the formula I, and $R_6$ is $C_1$-$C_4$ alkyl.

Namely, Process 18 is a process for producing a compound of the formula XLI by esterifying a compound of the formula XL having a —$CO_2H$ group by means of various conventional esterification methods. The following methods (a) to (d) may be employed for the esterification.

(a) Esterification by an alcohol of the formula $R_6OH$ in the presence of an acid catalyst such as sulfuric acid or hydrochloric acid.

(b) Conversion of the —$CO_2H$ group to a —COCl group, followed by the reaction with an alcohol of the formula $R_6OH$ in the presence of a dehydrochlorinating agent such as triethylamine or pyridine.

(c) Conversion of the —$CO_2H$ group to a metal salt of the formula —$CO_2M$ (wherein M is Na, K, Ag, etc.), followed by the reaction with an alkyl halide of the formula $R_6Hal$ (wherein Hal is chlorine, bromine or iodine).

(d) When $R_6$ in the formula XLI is methyl, a compound of the formula XL is reacted with diazomethane.

It is possible to obtain a desired product by suitably selecting one of the above methods (a) to (d) depending upon the chemical or physical properties of X, B, $Y_1$ and $Y_2$.

Namely, Process 19 is a process for producing a compound of the formula XLIII by converting the —$CONH_2$ group in the compound of the formula XLII to a —CN group by various methods commonly employed. For the conversion of the amide to the nitrile, various reaction examples are disclosed, for instance, in Compendium of Organic Synthetic Method (1971) Vol. I, p 464–465. It is possible to obtain a desired product by suitably selecting one of the conventional methods depending upon the chemical or physical properties of A, X, B, $Y_1$ and $Y_2$ in the compound of the formula XLII.

The above-mentioned 3(2H)pyridazinone compound of the formula II having a substituent at the 2-position, as a starting material, wherein both $R_2$ and Z are the same and chlorine or bromine, i.e. the compound of the formula IIa, may be prepared by known processes as shown in reaction scheme 2 (for instance, Process 2-1 disclosed in Advances in Heterocyclic Chemistry, Vol. 9, p. 257(1968) or Process 2-2 disclosed in Chemical Abstract, 62, 2772g).

Reaction scheme 2

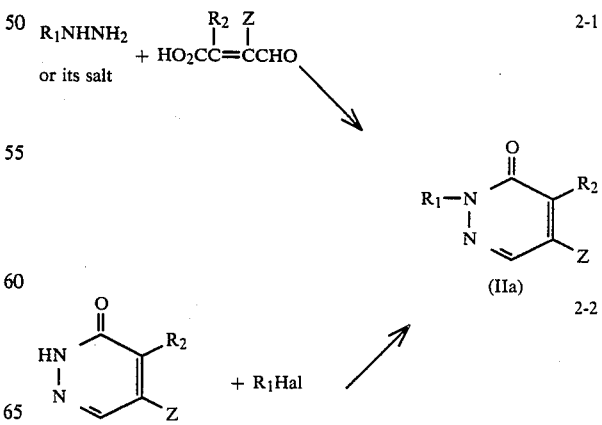

Process 19

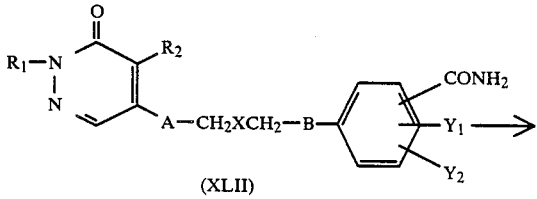

(XLII)

wherein $R_1$ is the same as defined above with respect to the formula I, and $R_2$, Z and Hal are chlorine or bromine. Process 2-1 is a reaction for the production of the compound of the formula IIa by the ring closure reaction of a hydrazine or its acid salt with a mucochloric acid or mucobromic acid. Process 2-2 is a reaction for the production of the compound of the formula IIa by reacting 4,5-(dichloro or bromo)-3(2H)pyridazinone with a compound of the formula $R_1$-Hal (wherein $R_1$ is alkyl, and Hal is chlorine, bromine or iodine). For the production of the compound of the formula IIa, Process 2-1 or Process 2-2 may optionally be selected. While it is advantageous to employ Process 2-1 from the viewpoint of the yield and operation efficiency, it is usually advantageous to employ Process 2-2 when a hydrazine is commercially hardly available or difficult to produce economically.

The compound of the formula II wherein $R_2$ is $C_1$–$C_8$ alkyl, may be prepared by a process as shown in reaction scheme 3 or 4.

Reaction scheme 3

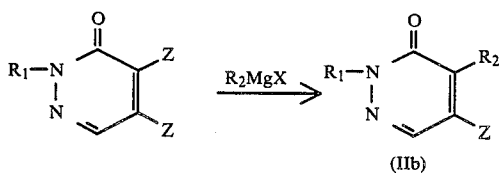

(IIb)

wherein $R_1$ and Z are the same as defined above with resect to the formula IIa, X is bromine or iodine, and $R_2$ is $C_1$–$C_8$ alkyl.

Namely, such a compound may readily be prepared by reacting a 2-alkyl-4,5-di-(chloro or bromo)-3(2H)-pyridazinone of the formula:

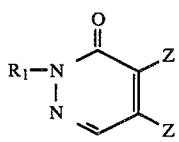

with a Grignard reagent of the formula $R_2$MgX in the presence of an inert gas. As the solvent, there may be employed a hydrocarbon solvent such as toluene or benzene, and an ether solvent such as tetrahydrofuran or ethyl ether.

The reaction temperature may be within a range of from 0° C. to the boiling point of the solvent used for the reaction.

The molar ratio of the starting materials may optionally be set. However, it is common to use from 1 to 5 mols, preferably from 1 to 3 mols, of the Grignard reagent relative to 1 mol of the 4,5-di-(chloro or bromo)-3(2H)pyridazinone.

Reaction scheme 4

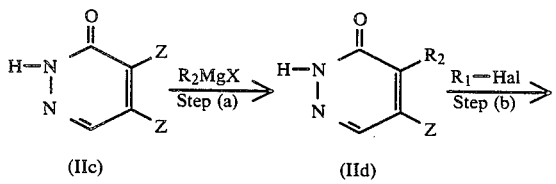

(IIc) (IId)

-continued
Reaction scheme 4

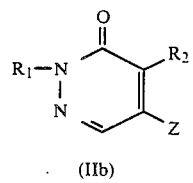

(IIb)

wherein $R_1$ and $R_2$ are the same as defined above with respect to reaction scheme 3, and Hal is the same as defined above with respect to Process 2-2.

Namely, the compound of the formula IIb may also be obtained by reacting 4,5-di-(chloro or bromo)-3(2H)-pyridazinone of the formula IIc having no substituent at the 2-position with a Grignard reagent of the formula $R_2$MgX to obtain a compound of the formula IId, and reacting the compound of the formula IId with an alkyl halide of the formula $R_1$Hal.

Step (a) may be conducted under the conditions similar to those of reaction scheme 3. Likewise, Step (b) may be conducted in the same manner as in reaction scheme 2-2.

The 3(2H)pyridazinone compound of the formula IIe having a hydroxyl group at the 5-position, as a starting material in processes 2, 3 and 11, may be prepared by a conventional method as shown by reaction scheme 5.

Reaction scheme 5

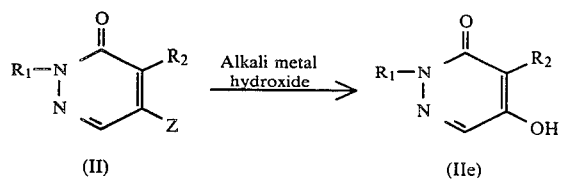

(II) (IIe)

wherein $R_1$ and $R_2$ are as defined above with respect to the formula I, and Z is chlorine or bromine.

Namely, the compound of the formula IIe can be readily obtained by reacting the 3(2H)pyridazinone compound of the formula II having chlorine or bromine at the 5-position, with an alkali metal hydroxide such as sodium hydroxide or potassium hydroxide in water or an alcohol solvent such as ethanol or methanol, or in a solvent mixture thereof at a temperature within a range of from 50° C. to the boiling point of the solvent used.

Likewise, the compound of the formula IIf having —NHR$_3$ (wherein $R_3$ is as defined above with respect to the formula I) at the 5-position, may be prepared by a conventional method as shown by the following Reaction scheme 6.

Reaction scheme 6

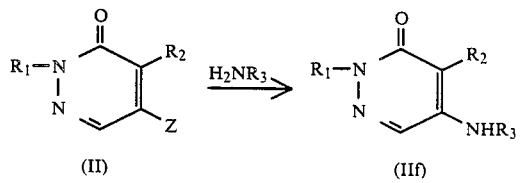

(II) (IIf)

wherein $R_1$, $R_2$ and $R_3$ are as defined above with respect to the formula I, and Z is chlorine or bromine.

Namely, the compound of the formula IIf can be obtained by reacting a pyridazinone compound of the formula II with a compound of the formula H₂NR₃. As the organic solvent, a polar solvent such as water, methanol, ethanol, tetrahydrofuran, 1,4-dioxane, dimethylformamide or pyridine, is particularly preferred. However, it is also possible to use an amine compound of the formula H₂NR₃ as the solvent. When R₃ is hydrogen i.e. H₂NR₃ is ammonia, the desired product can readily be obtained in good yield by reacting the compound of the formula II with ammonia under pressure.

Among the compounds of the formulas VII and X used as the other starting materials in processes 1 and 2, those which are not readily available as commercial products can be prepared by such a suitable method selected from the following conventional methods as A to L depending upon the reactivity of Y₁, Y₂, Y₃, X and B. Methods G to L will be described with respect to the preparation of the compounds of the formula VII wherein B is a single bond. Further, Y₁, Y₂, Y₃, B, A and n are as defined above with respect to the formula I, unless otherwise specifically indicated.

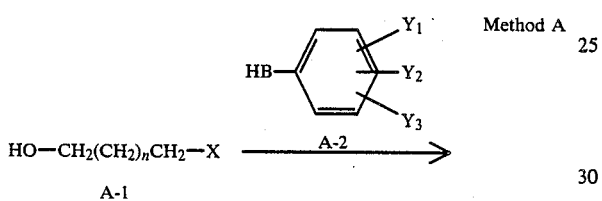

wherein X is chlorine, bromine or iodine, and B is —O—, —S— or —NH—. Method A is a process for producing a compound of the formula A-3 by reacting a compound of the formula A-1 with a phenol, a thiophenol or an aniline of the formula A-2 in a usual solvent in the presence of a dehydrohalogenating agent.

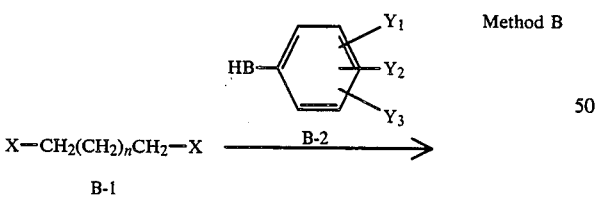

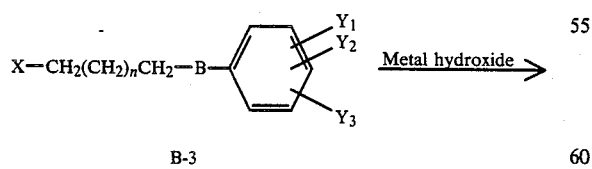

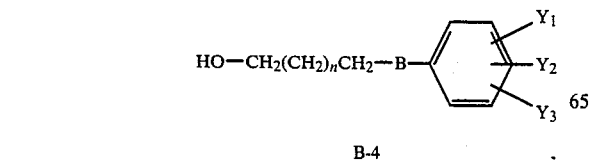

wherein X and B are as defined above with respect to Method A.

Method B is a process for producing a compound of the formula B-4 by reacting a compound of the formula B-1 with a phenol, a thiophenol or an aniline of the formula B-2 in the presence of a dehydrohalogenating agent to obtain a compound of the formula B-3, and then hydrolyzing this compound with an aqueous solution of a metal hydroxide such as sodium hydroxide, if necessary, after reacting it with a metal acetate such a sodium acetate to convert it into an acetate.

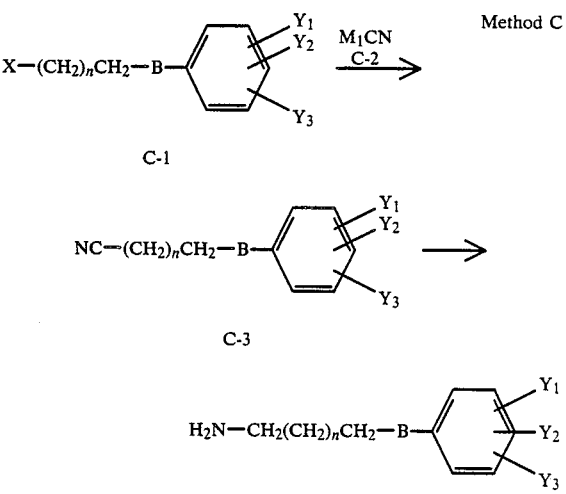

wherein X and B are as defined above with respect to Method A, and M₁ is sodium or potassium.

Method C is a process wherein the halide of the formula C-1 obtained in Method B is reacted with a metal cyanide of the formula C-2 to obtain a cyano compound, which is then converted by a reducing agent to a corresponding amino compound.

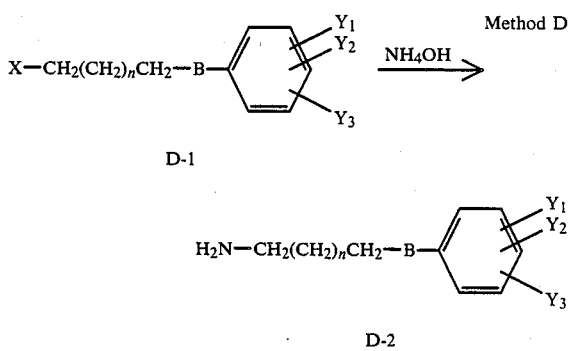

wherein X and B are as defined above with respect to Method A.

Method D is a process wherein a compound of the formula D-1 is subjected to ammonolysis reaction to convert it to a substituted amine of the formula D-2.

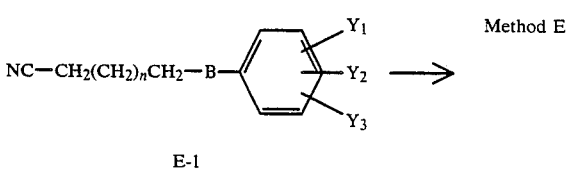

-continued

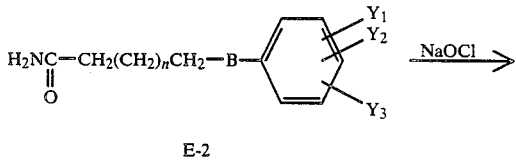
E-2

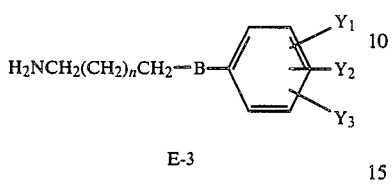
E-3 wherein B is —O— or —S—.

Method E is a process wherein a compound of the formula E-1 obtained in the same manner as in Method C, is subjected to amidation to obtain a corresponding amide compound of the formula E-2, which is then converted to an amino compound of the formula E-3 by a Hoffmann reaction.

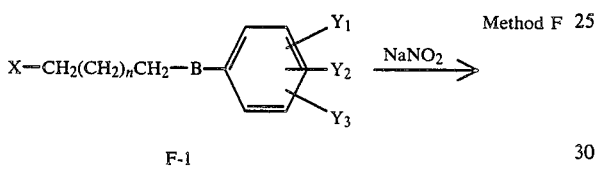
F-1

Method F

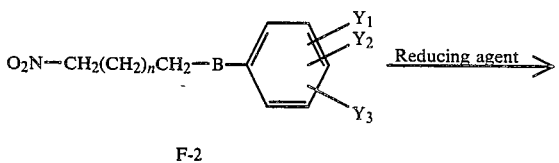
F-2

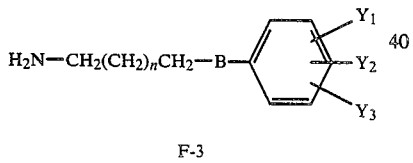
F-3 wherein X and B are as defined above with respect to Method A.

Method F is a process wherein a halide of the formula F-1 is reacted with NaNO$_2$ to obtain a corresponding nitro compound of the formula F-2, which is then treated with a reducing agent such as a Fe/FeSO$_4$ type reducing agent, to obtain a corresponding amine of the formula F-3.

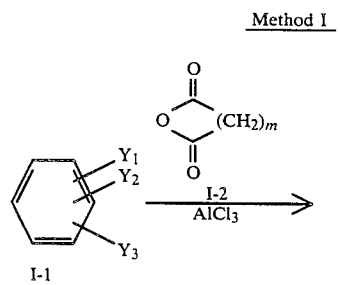
G-1     G-3

Method G wherein m is 2 or 3.

Method G is a process for producing a compound of the formula G-3 by reacting a benzene of the formula G-1 with a compound of the formula G-2 by a Friedel-Crafts reaction.

Method H

H-1

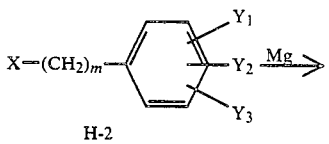
H-2

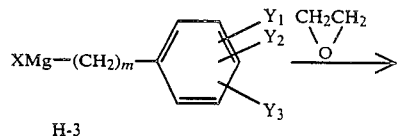
H-3

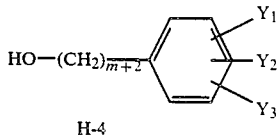
H-4 wherein X is chlorine or bromine, m is as defined above with respect to Method G.

Method H is a process wherein an alcohol compound of the formula H-1 is halogenated with a halogenating agent to a compound of the formula H-2, which is then converted to a Grignard reagent of the formula H-3, which is then reacted with ethylene oxide to obtain a compound of the formula H-4.

Method I

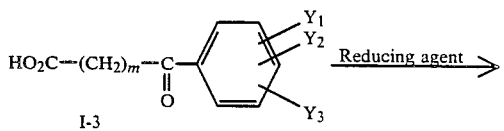
I-1

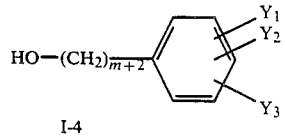
I-3

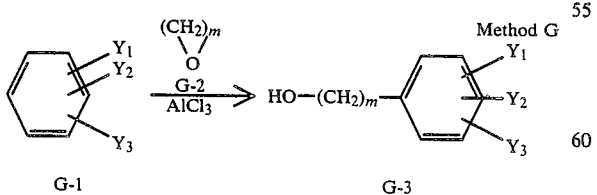
I-4 wherein m is as defined above with respect to Method G.

Method I is a process wherein a benzene of the formula I-1 is reacted with an acid anhydride of the formula I-2 by a Friedel-Crafts reaction to obtain a compound of the formula I-3, which is then reduced by a reducing agent to an alcohol compound of the formula I-4.

Method J

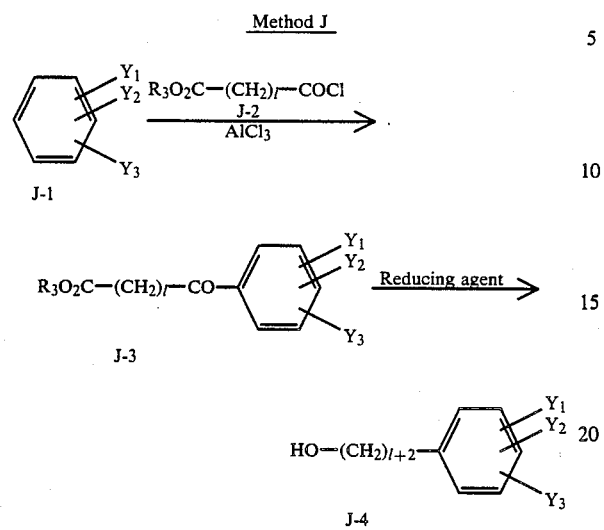

wherein is an integer of 0 to 4, and $R_3$ is $C_1$-$C_4$ alkyl.

Method J is a process wherein a benzene of the formula J-1 and an acid chloride of the formula J-2 are reacted by a Friedel-Crafts reaction to obtain a compound of the formula J-3, which is further reduced by a reducing agent to an alcohol compound of the formula J-4.

Method K

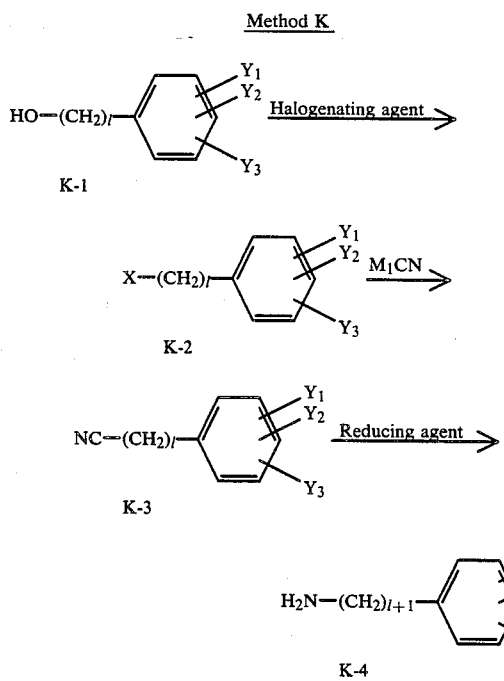

wherein X is as defiend above with respect to Method A, $M_1$ is as defined above with respect to Method C, and l is an integer of 1 to 5.

Method K is a process wherein an alcohol compound of the formula K-1 is halogenated by a halogenating agent to obtain a halide of the formula K-2, which is then reacted with a metal cyanide to obtain a cyanide of the formula K-3, and the —CN group of this cyanide is reduced to obtain an amine compound of the formula K-4.

Method L

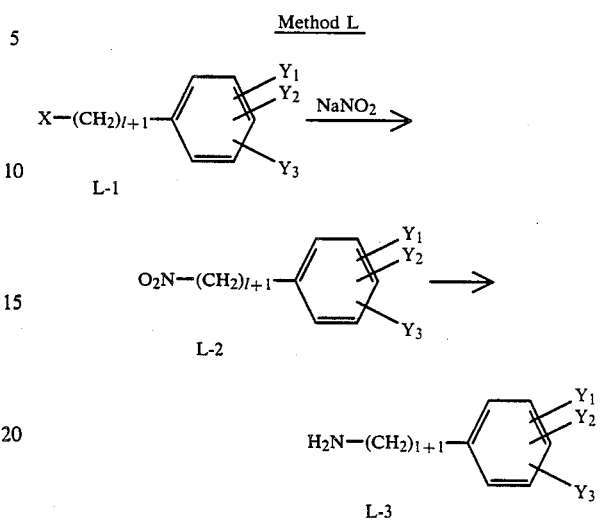

wherein X is as defined above with respect to Method A, and l is as defined above with respect to Method K.

Method L is a process wherein a compound of the formula L-1 and sodium nitrite were reacted to obtain a nitro compound of the formula L-2, and this compound was reacted with a reducing agent to obtain an amine compound of the formula L-3.

In addition to the compounds described in the Examples given hereinafter, specific examples of the compounds of the present invention will be given in Table 1. In the following compounds, "i" means iso, "n" means normal, "Me" means methyl, "Et" means ethyl, "Pr" means propyl, "Bu" means butyl, "Pen" means pentyl, "Hex" means hexyl, "Hep" means heptyl, "Oct" means octyl, and "-" means a single bond.

TABLE 1

| $R_1$ | $R_2$ | A | X | B | $Y_1$ | $Y_2$ | $Y_3$ |
|---|---|---|---|---|---|---|---|
| i-Pr | Cl | NH | — | O | 2-n-Pr | 4-CO$_2$Me | H |
| Et | Cl | NH | — | O | 2-n-Pr | 4-CO$_2$Me | H |
| Me | Cl | O | CH$_2$ | O | 2-n-Pr | 4-CO$_2$Me | H |
| i-Pr | Cl | NH | — | — | 2-OMe | H | H |
| Et | Cl | NH | — | — | 2-Me | H | H |
| Et | Cl | O | CH$_2$ | O | 2-Cl | 4-(N=N–NH–N=N tetrazole) | H |
| iPr | Cl | NH | CH$_2$ | O | 2-Cl | 4-(N=N–NH–N=N tetrazole) | H |
| i-Pr | Cl | O | CH$_2$ | O | 2-Cl | 4-CO$_2$H | H |
| Et | Cl | O | CH$_2$ | O | 4-OEt | H | H |

TABLE 1-continued

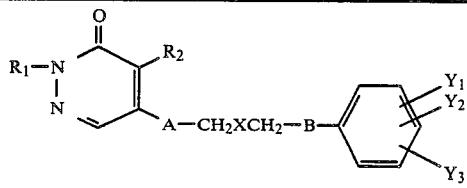

| R1 | R2 | A | X | B | Y1 | Y2 | Y3 |
|---|---|---|---|---|---|---|---|
| H | Cl | NH | $CH_2$ | O | 2-n-Hex | 4-$CO_2$Me | H |
| H | Br | NH | $CH_2$ | O | 2-n-Hex | 4-$CO_2$Me | H |
| H | Cl | NH | $CH_2$ | O | 2-n-Hep | 4-CN | H |
| H | Br | NH | $CH_2$ | O | 2-n-Hep | 4-CN | H |
| H | Cl | NH | $CH_2$ | O | 2-n-Hep | 4-$CO_2$H | H |
| H | Br | NH | $CH_2$ | O | 2-n-Hep | 4-$CO_2$H | H |
| H | Cl | NH | $CH_2$ | O | 2-n-Hep | 4-$CONH_2$ | H |
| H | Br | NH | $CH_2$ | O | 2-n-Hep | 4-$CONH_2$ | H |
| H | Cl | NH | $CH_2$ | O | 2-n-Oct | 4-$CO_2$H | H |
| H | Br | NH | $CH_2$ | O | 2-n-Oct | 4-$CO_2$H | H |
| H | Cl | NH | $CH_2$ | O | 2-n-Bu | 4-OMe | H |
| H | Br | NH | $CH_2$ | O | 2-n-Bu | 4-OMe | H |
| H | Cl | NH | $CH_2$ | O | 2-n-Pen | 4-OH | H |
| H | Br | NH | $CH_2$ | O | 2-n-Pen | 4-OH | H |
| H | Et | NH | $CH_2$ | O | 2-n-Bu | 4-$CO_2$Me | H |
| H | Et | NH | $CH_2$ | O | 2-n-Bu | 4-CN | H |
| H | Et | NH | $CH_2$ | O | 2-n-Pen | 4-CN | H |
| H | Et | NH | $CH_2$ | O | 2-n-Hex | 4-$CO_2$H | H |
| H | Et | NH | $CH_2$ | O | 2-n-Hex | 4-$CONH_2$ | H |
| i-Pr | Br | NH | CH(OMe) | O | 2-n-Pr | 4-CN | H |
| Et | Cl | NH | CH(OMe) | O | 2-n-Pr | 4-$CO_2$Me | H |
| Et | Br | NH | CH(OMe) | O | 2-n-Pr | 4-$CO_2$Me | H |
| Et | Cl | NH | CH(OMe) | O | 2-n-Bu | 4-CN | H |
| Et | Br | NH | CH(OMe) | O | 2-n-Bu | 4-CN | H |
| i-Pr | Cl | NH | CH(OMe) | O | 2-n-Bu | 4-$CO_2$H | H |
| i-Pr | Br | NH | CH(OMe) | O | 2-n-Bu | 4-$CO_2$H | H |
| Et | Cl | NH | CH(OMe) | O | 2-n-Pen | 4-$CO_2$H | H |
| Et | Br | NH | CH(OMe) | O | 2-n-Pen | 4-$CO_2$H | H |
| Et | Cl | NH | CH(OH) | O | 2-n-Bu | 4-$CO_2$Me | H |
| Et | Br | NH | CH(OH) | O | 2-n-Bu | 4-$CO_2$Me | H |
| i-Pr | Cl | NH | CH(OH) | O | 2-n-Bu | 4-$CO_2$Me | H |
| i-Pr | Br | NH | CH(OH) | O | 2-n-Bu | 4-$CO_2$Me | H |
| i-Pr | Cl | NH | CH(OH) | O | 2-n-Bu | 4-CN | H |
| i-Pr | Br | NH | CH(OH) | O | 2-n-Bu | 4-CN | H |
| H | Me | NH | $CH_2$ | O | 2-n-Bu | 4-$CO_2$Me | H |
| H | Me | NH | $CH_2$ | O | 2-n-Bu | 4-$CO_2$H | H |
| H | Me | NH | $CH_2$ | O | 2-n-Bu | 4-$CONH_2$ | H |
| H | Me | NH | $CH_2$ | O | 2-n-Pen | 4-$CO_2$Me | H |
| H | Me | NH | $CH_2$ | O | 2-n-Pen | 4-$CO_2$H | H |
| H | Me | NH | $CH_2$ | O | 2-n-Pen | 4-$CONH_2$ | H |
| H | Me | NH | $CH_2$ | O | 2-n-Hex | 4-$CO_2$H | H |
| i-Pr | Cl | NH | — | O | 2-n-Bu | 4-$CO_2$H | H |
| i-Pr | Br | NH | — | O | 2-n-Bu | 4-$CO_2$H | H |
| i-Pr | Br | NH | — | O | 2-n-Pen | 4-$CO_2$H | H |
| H | n-Pr | O | $CH_2$ | O | 2-n-Pr | 4-$CO_2$H | H |
| H | n-Pr | O | $CH_2$ | O | 2-n-Bu | 4-$CO_2$H | H |
| n-Pr | Br | NH | $CH_2$ | O | 2-n-Pr | 4-$CO_2$H | H |
| n-Pr | Br | NH | $CH_2$ | O | 2-n-Pr | 4-$CO_2$Me | H |
| n-Pr | Cl | NH | $CH_2$ | O | 2-n-Bu | 4-$CO_2$H | H |
| H | n-Pr | NH | $CH_2$ | O | 2-n-Bu | 4-$CO_2$Me | H |
| H | n-Pr | NH | $CH_2$ | O | 2-n-Bu | 4-$CO_2$H | H |
| H | n-Pr | NH | $CH_2$ | O | 2-n-Pen | 4-$CO_2$H | H |
| i-Pr | Br | NH | $(CH_2)_2$ | O | 2-n-Pr | 4-$CO_2$H | H |
| i-Pr | Cl | NH | $(CH_2)_2$ | O | 2-n-Pr | 4-$CO_2$H | H |
| i-Pr | Br | NH | $(CH_2)_3$ | O | 2-n-Pr | 4-$CO_2$H | H |
| i-Pr | Cl | NH | $(CH_2)_4$ | O | 2-n-Pr | 4-$CO_2$H | H |
| i-Pr | Br | NH | — | — | 3-O—n-Pr | 4-OMe | H |
| i-Pr | Cl | NH | — | — | 3-O—n-Pr | 4-OMe | H |
| i-Pr | Br | NH | — | — | 3-O—n-Bu | 4-OMe | H |
| H | n-Pr | NMe | $CH_2$ | O | 2-n-Pr | 4-$CO_2$H | H |
| H | Br | NMe | $CH_2$ | O | 2-n-Bu | 4-$CO_2$H | H |
| H | Cl | NH | — | — | 4-O—n-Bu | H | H |
| H | Br | NH | — | — | 4-O—n-Bu | H | H |
| Et | Cl | NH | — | — | 4-OEt | H | H |
| Et | Br | NH | — | — | 4-OEt | H | H |
| Et | Cl | NH | — | — | 4-O—n-Pr | H | H |
| Et | Br | NH | — | — | 4-O—n-Pr | H | H |
| i-Pr | Cl | NH | — | — | 4-OEt | H | H |
| i-Pr | Br | NH | — | — | 4-OEt | H | H |
| H | Cl | O | $CH_2$ | O | 2-n-Bu | 4-$CO_2$Me | H |
| H | Br | O | $CH_2$ | O | 2-n-Bu | 4-$CO_2$Me | H |

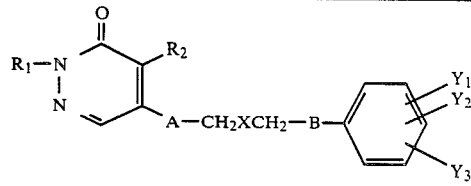

| R1 | R2 | A | X | B | Y1 | Y2 | Y3 |
|---|---|---|---|---|---|---|---|
| H | Cl | O | $CH_2$ | O | 2-n-Bu | 4-CN | H |
| H | Br | O | $CH_2$ | O | 2-n-Bu | 4-CN | H |
| H | Cl | O | $CH_2$ | O | 2-n-Pen | 4-$CO_2$H | H |
| H | Br | O | $CH_2$ | O | 2-n-Pen | 4-$CO_2$H | H |
| H | Cl | O | CH(OH) | O | 2-n-Bu | 4-$CO_2$H | H |
| H | Br | O | CH(OH) | O | 2-n-Bu | 4-$CO_2$H | H |
| H | Cl | O | CH(OH) | O | 2-n-Bu | 4-$CO_2$Me | H |
| H | Br | O | CH(OH) | O | 2-n-Bu | 4-$CO_2$Me | H |
| H | Cl | O | CH(OH) | O | 2-n-Pen | 4-$CO_2$H | H |
| H | Br | O | CH(OH) | O | 2-n-Pen | 4-$CO_2$H | H |
| H | Cl | O | CH(OH) | O | 2-n-Bu | 4-CN | H |
| H | Br | O | CH(OH) | O | 2-n-Bu | 4-CN | H |
| Et | Cl | NH | CH(OH) | O | 2-n-Pen | 4-$CO_2$Me | H |
| Et | Br | NH | CH(OH) | O | 2-n-Pen | 4-$CO_2$Me | H |
| Et | Cl | NH | CH(OH) | O | 2-n-Pen | 4-CN | H |
| Et | Br | NH | CH(OH) | O | 2-n-Pen | 4-CN | H |
| i-Pr | Cl | NH | CH(OH) | O | 2-n-Hex | 4-$CO_2$H | H |
| i-Pr | Br | NH | CH(OH) | O | 2-n-Hex | 4-$CO_2$H | H |
| Et | Cl | NH | — | S | 2-n-Bu | 4-$CO_2$H | H |
| Et | Br | NH | — | S | 2-n-Bu | 4-$CO_2$H | H |
| i-Pr | Cl | NH | — | S | 2-n-Bu | 4-$CO_2$H | H |
| i-Pr | Br | NH | — | S | 2-n-Bu | 4-$CO_2$H | H |
| i-Pr | Cl | NH | $CH_2$ | O | 2-(1-butenyl) | 4-$CO_2$H | H |
| i-Pr | Br | NH | $CH_2$ | O | 2-(1-butenyl) | 4-$CO_2$H | H |
| H | n-Pen | NH | $CH_2$ | O | 2-n-Pr | 4-$CO_2$H | H |

As the manner of administration of the compounds of the present invention, there may be mentioned a non-oral administration by injection (subcutaneous, intravenous, intramuscular or intraperitoneal injection), an ointment, a suppository or an aerosol, or an oral administration in the form of tablets, capsules, granules, pills, sirups, liquids, emulsions or suspensions.

The above pharmacological or veterinary composition contains a compound of the present invention in an amount of from about 0.1 to about 99.5% by weight, preferably from about 0.5 to about 95% by weight, based on the total weight of the composition. To the compound of the present invention or to the composition containing the compound of the present invention, other pharmacologically or veterinarily active compounds may be incorporated. Further, the composition of the present invention may contain a plurality of compounds of the present invention.

The clinical dose of the compound of the present invention varies depending upon the age, the body weight, the sensitivity or the symptom, etc. of the patient. However, the effective daily dose is usually from 0.003 to 1.5 g, preferably from 0.01 to 0.6 g, for an adult. However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as sirups, gum arabic, gelatin, sorbitol, tragacant gum, methyl cellulose or polyvinylpyrrolidone; a disintegrant such as starch, carboxymethyl cellulose or its calcium salt, crystal cellulose powder or polyethylene glycol; a gloss agent such as talc, magnesium or calcium stearate or colloidal silica; or a lubricant such as sodium laurate or glycerol. The injections, solutions, emulsions, suspensions, sirups or aerosols, may be prepared by using a solvent for the active ingredient such as water, ethyl alcohol, isopropyl alcohol, propylene glycole, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl, a cellulose derivative such as methyl cellulose, or a natural rubber such as tragacant gum or gum arabic; or a preservative such as a paraoxy benzoic acid ester, benzalkonium chloride or a salt of sorbic acid. Likewise, the suppositories may be prepared by using e.g. polyethylene glycol, lanolin or cocoa butter.

TEST EXAMPLES

A. Anti-allergic activities

A major constituent of SRS-A which is an important mediator for immediate allergy such as bronchoconstiriction in bronchial asthma, has already been found to be leukotriene $C_4$ (hereinafter referred to as $LTC_4$), leukotriene $D_4$ (hereinafter referred to as $LTD_4$) or the like. Accordingly, antagonistic activities against SRS-A can be evaluated by any one of the following test methods:

(1) a method of examining the antagonistic activities against SRS-A obtained from a sensitized guinea-pig, (2) a method of examining the antagonistic activities against $LTC_4$, and (3) a method of examining the antagonistic activities against $LTD_4$.

The present inventors examined the antagonistic activities against SRS-A by using the test methods (1) to (3).

Now, the test methods and the results will be described.

Test methods of anti-allergic activities and the results (i) $LTC_4$ and $LTD_4$ antagonisms in guinea-pig trachea Antagonisms for $LTC_4$ and $LTD_4$ were determined in isolated guinea-pig trachea prepared as spiral strip. Tracheal preparations were suspended under 1 g tension in 10 ml organ baths and they were incubated for 1 hr prior to use. Contractile responses to $LTC_4$ ($2 \times 10^{-8}$ g/ml) and $LTD_4$ ($2 \times 10^{-8}$ g/ml) were obtained after the maximal response to histamine ($10^{-4}$M). Test compounds dissolved in 100% dimethyl sulfoxide were added to the organ baths (final concentration of $10^{-5}$ g/ml or $10^{-6}$ g/ml) 5 min prior to $LTC_4$ and $LTD_4$ addition, and then contractile responses to $LTC_4$ and $LTD_4$ were compared with those of control which was obtained from a paired trachea in the absence of test compounds. $LTC_4$- and $LTD_4$-induced contractions were expressed as a percentage of the maximal response to histamine. The antagonism was determined as follows:

Antagonism (%) = (1.0 − % contraction in test/% contraction in control) × 100

$LTC_4$ antagonisms by test compounds ($10^{-5}$ g/ml) are shown in Table 2.

TABLE 2

| Test compound No. | Antagonism (%) |
|---|---|
| 4 | 99 |
| 7 | 95 |
| 20 | 73 |
| 23 | 27 |
| 25 | 53 |
| FPL-55712 | 100 |

$LTC_4$ antagonisms by test compounds ($10^{-5}$ g/ml) are shown in Table 3.

TABLE 3

| Test Compound No. | Antagonism (%) | Test Compound No. | Antagonism (%) |
|---|---|---|---|
| 1 | 49 | 60 | 98 |
| 2 | 15 | 61 | 73 |
| 3 | 28 | 62 | 57 |
| 4 | 85 | 63 | 54 |
| 5 | 33 | 64 | 87 |
| 6 | 96 | 65 | 98 |
| 7 | 82 | 66 | 69 |
| 8 | 32 | 67 | 99 |
| 9 | 14 | 68 | 33 |
| 10 | 46 | 69 | 99 |
| 11 | 13 | 70 | 65 |
| 12 | 35 | 71 | 88 |
| 13 | 53 | 72 | 85 |
| 14 | 40 | 73 | 48 |
| 15 | 40 | 74 | 73 |
| 16 | 31 | 75 | 16 |
| 17 | 45 | 76 | 57 |
| 18 | 20 | 77 | 17 |
| 19 | 60 | 78 | 32 |
| 20 | 80 | 79 | 58 |
| 23 | 31 | 80 | 98 |
| 24 | 40 | 81 | 80 |
| 25 | 24 | 82 | 100 |
| 26 | 15 | 83 | 46 |
| 27 | 65 | 84 | 85 |
| 28 | 61 | 85 | 78 |
| 29 | 18 | 86 | 59 |
| 30 | 40 | 87 | 60 |
| 31 | 19 | 88 | 97 |
| 32 | 29 | 89 | 52 |
| 33 | 15 | 90 | 83 |
| 34 | 61 | 91 | 14 |
| 35 | 72 | 92 | 100 |
| 37 | 40 | 93 | 79 |
| 41 | 100 | 94 | 98 |
| 42 | 95 | 95 | 59 |
| 43 | 63 | 96 | 77 |
| 44 | 90 | 97 | 62 |
| 45 | 27 | 98 | 89 |
| 47 | 99 | 99 | 51 |
| 48 | 36 | 100 | 66 |
| 49 | 57 | 101 | 92 |
| 50 | 35 | 102 | 93 |
| 51 | 82 | 103 | 93 |
| 52 | 23 | 104 | 57 |
| 53 | 59 | 105 | 89 |
| 54 | 64 | 106 | 93 |
| 55 | 72 | 107 | 85 |
| 56 | 62 | 108 | 94 |
| 57 | 83 | 109 | 99 |
| 58 | 88 | 110 | 77 |
| 59 | 82 | 111 | 87 |
| 112 | 100 | 160 | 70 |
| 113 | 100 | 161 | 71 |
| 114 | 89 | 162 | 81 |
| 115 | 94 | 163 | 74 |
| 116 | 90 | 164 | 71 |
| 117 | 98 | 165 | 33 |
| 118 | 91 | 166 | 25 |
| 119 | 100 | 167 | 30 |
| 140 | 41 | 168 | 21 |
| 141 | 54 | 169 | 50 |
| 142 | 69 | 170 | 17 |

TABLE 3-continued

| Test Compound No. | Antagonism (%) | Test Compound No. | Antagonism (%) |
|---|---|---|---|
| 143 | 26 | 171 | 66 |
| 144 | 84 | 172 | 79 |
| 145 | 85 | 173 | 35 |
| 146 | 14 | 174 | 78 |
| 147 | 66 | 175 | 55 |
| 148 | 17 | | |
| 149 | 81 | FPL-55712 | 97 |
| 150 | 16 | | |
| 151 | 47 | | |
| 152 | 60 | | |
| 153 | 64 | | |
| 154 | 20 | | |
| 155 | 55 | | |
| 156 | 56 | | |
| 157 | 62 | | |
| 158 | 93 | | |
| 159 | 44 | | |

(ii) LTD$_4$ antagonism in guinea-pig trachea

Antagonism for LTD$_4$ was determined in isolated guinea-pig trachea prepared as spiral strip. Tracheal preparations were suspended under 1 g tension in 10 ml organ baths containing 5 μmol of indomethacin and they were incuated for 1 hr prior to use. Contractile responses to LTD$_4$ ($2 \times 10^{-8}$ g/ml) were obtained after the maximal response to histamine ($10^{-4}$M). Test compounds dissolved in 100% dimethyl sulfoxide were added to the organ baths (final concentration of $10^{-6}$ g/ml) 30 min prior to LTD$_4$ addition, and then contractile responses to LTD$_4$ were compared with those of control which was obtained from a paired trachea in the absence of test compounds. LTD$_4$-induced contractions were expressed as a percentage of the maximal response to histamine. The antagonism was determined as follows:

Antagonism (%) = (1.0 − % contraction in test/% contraction in control) × 100

LTD$_4$ antagonisms by test compounds ($10^{-6}$ g/ml) are shown in Table 4. In Table 4, the values with an asterisk "*" were obtained by Test method (i), and others were obtained by Test method (ii).

TABLE 4

| Test compound No. | Antagonism (%) | Test compound No. | Antagonism (%) |
|---|---|---|---|
| FPL-55712 | 76*, 94 | 125 | 84 |
| 6 | 78* | 126 | 90 |
| 41 | 82 | 127 | 91* |
| 42 | 76 | 128 | 17* |
| 44 | 63 | 131 | 33* |
| 69 | 66* | 132 | 26* |
| 80 | 59* | 133 | 27* |
| 98 | 80 | 135 | 57 |
| 105 | 52 | 137 | 53 |
| 109 | 69 | 158 | 53* |
| 111 | 79 | 178 | 69 |
| 112 | 62* | 179 | 63 |
| 113 | 54 | 180 | 88 |

TABLE 4-continued

| Test compound No. | Antagonism (%) | Test compound No. | Antagonism (%) |
|---|---|---|---|
| 114 | 66* | 181 | 70 |
| 115 | 61 | 197 | 82 |
| 116 | 82* | 198 | 86 |
| 117 | 67* | 199 | 65 |
| 118 | 69* | 200 | 81 |
| 120 | 82* | 202 | 89 |
| 121 | 43* | 203 | 94 |
| 122 | 94 | 204 | 95 |
| 123 | 65* | 205 | 96 |
| 124 | 92 | 218 | 84 |

(iii) Effect on anaphylactic bronchoconstriction in passively sensitized guinea-pig Male guinea-pigs (350–450 g) were passively sensitized with intravenous (i.v.) injection of 0.125 ml rabbit anti-EA (egg albumin) serum (Cappel Laboratories) 1 day preceding the experiment. Antigen-induced anaphylactic bronchoconstrictions were measured by modified method of Konzett and Rossler (Arch. Exp. Path. Pharmak., 195, 71, 1940). Sensitized guinea-pigs were anaesthetized with intraperitoneal injection of urethane (1.5 g/kg). The right jugular vein was cannulated for the administration of the all agents and trachea was cannulated to record total pulmonary resistance. Guinea-pigs were artificially ventilated by a small animal respirator (Shinano, Model SN-480-7) set at a stroke volume of 5 ml and a rate of 50 breaths per min. The change in pulmonary resistance was measured with a pressure transducer (Nihon Kohden, Model TP-602T) connected to a T-tube on the tracheal cannula. The increase in air overflow volume was expressed as a percentage of the maximum bronchoconstriction obtained by clamping off the trachea. Following surgical preparation, the animals were pretreated with indomethacin (1.0 mg/kg, 10 min), pyrilamine (2 mg/kg, 6 min) and propranolol (0.1 mg/kg, 5 min) prior to the EA challenge (0.1 or 10 mg/kg). All test compounds, 2 mg/kg in 3% Tween 80 or 3% PEG-400, were administered 1 min before the EA challenge. Inhibition (%) of bronchoconstriction was determined as follows: Inhibition (%) = (1.0% − maximum bronchoconstriction in test/% maximum bronchoconstriction in control) × 100. The maximum bronchoconstriction was obtained within 20 min after the EA challenge. The number of test animals was 4 and the mean inhibition was compared with that of FPL-55712 (Fisons Limited) of the following formula:

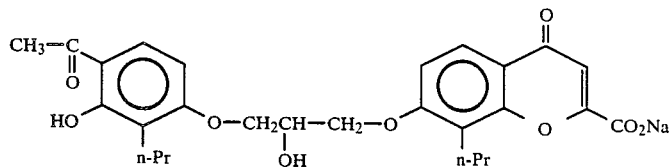

Effect of the test compounds (2 mg/kg, i.v.) are shown in Table 5-(1) and 5-(2).

TABLE 5-(1)

| Test compound No. | Inhibition (%) |
|---|---|
| 4 | 27 |
| 7 | 31 |
| 25 | 18 |
| 27 | 23 |

TABLE 5-(1)-continued

| Test compound No. | Inhibition (%) |
|---|---|
| 28 | 17 |
| 43 | 24 |
| 47 | 28 |
| 51 | 15 |
| 55 | 26 |
| 60 | 15 |
| FPL-55712 | 27 |

In the Table, the dose of EA was 10 mg/kg, and each compound was dissolved or suspended in 3% Tween 80.

TABLE 5-(2)

| Test compound No. | Solution or suspension for test compound | Inhibition (%) | Test compound No. | Solution suspension for test compound | Inhibition (%) |
|---|---|---|---|---|---|
| 6 | PEG-400 | 44 | 85 | Tween 80 | 23 |
| 41 | Tween 80 | 31 | 101 | PEG-400 | 51 |
| 42 | PEG-400 | 31 | 102 | PEG-400 | 73 |
| 64 | Tween 80 | 56 | 103 | PEG-400 | 69 |
| 65 | Tween 80 | 27 | 161 | Tween 80 | 20 |
| 67 | Tween 80 | 62 | 162 | Tween 80 | 49 |
| 69 | Tween 80 | 51 | 163 | Tween 80 | 32 |
| 71 | Tween 80 | 26 | 164 | Tween 80 | 40 |
| 74 | Tween 80 | 50 | FPL-55712 | Tween 80 | 60 |

The dose of EA was 0.1 mg/kg.

B. Acute toxicity test (i) Test method-(1)

The lethal ratio was determined in ddY strain male mice (4 weeks old) at 7 days after the oral administation of test compounds. The results are shown in Table 6.

TABLE 6

| Test compound No. | Dose (mg/kg) | Lethal ratio |
|---|---|---|
| 72 | 400 | 0/2 |
| 80 | 400 | 0/2 |
|    | 800 | 0/2 |
| 82 | 400 | 0/2 |
|    | 800 | 0/2 |
| 94 | 400 | 0/2 |
|    | 800 | 0/2 |
| 101 | 400 | 0/2 |
|     | 800 | 0/2 |

(ii) Test method-(2)

The lethal ratio was determined in ddY strain male mice (4 weeks old) at 7 days after the intraperitoneal injection of test compounds. The results are shown in Table 7.

TABLE 7

| Test compound No. | Dose (mg/kg) | Lethal ratio (Death number/Experimental number) |
|---|---|---|
| 1 | 200 | 0/2 |
|   | 400 | 0/1 |
| 4 | 200 | 0/2 |
|   | 400 | 0/1 |
| 7 | 200 | 0/2 |
|   | 400 | 0/1 |
| 10 | 200 | 0/2 |
|    | 400 | 0/1 |
| 13 | 200 | 0/2 |
|    | 400 | 0/1 |
| 14 | 200 | 0/2 |
|    | 400 | 0/1 |
| 27 | 100 | 0/2 |
|    | 200 | 0/2 |

TABLE 7-continued

| Test compound No. | Dose (mg/kg) | Lethal ratio (Death number/Experimental number) |
|---|---|---|
| 28 | 200 | 0/2 |
|    | 400 | 0/1 |
| 29 | 200 | 0/2 |
|    | 400 | 0/1 |
| 35 | 200 | 0/2 |
|    | 400 | 0/1 |
| 42 | 200 | 0/2 |
|    | 400 | 0/1 |
| 44 | 200 | 0/1 |
|    | 400 | 0/1 |
| 45 | 200 | 0/2 |
|    | 400 | 0/1 |
| 41 | 200 | 0/2 |
| 47 | 200 | 0/2 |
|    | 400 | 0/2 |
| 142 | 200 | 0/2 |
|     | 400 | 0/1 |
| 145 | 200 | 0/2 |
|     | 400 | 0/1 |

From these results, it is evident that the compounds of the present invention produce prominent effects on the angtagonism for SRS-A and its major constituents $LTC_4$ and $LTD_4$ in vitro and in vivo. Therefore, the compounds of the present invention are proved to be useful for prophylactic and therapeutic drugs in SRS-A-induced various allergic diseases, for example bronchial asthma, allergic rhinitics and urticaria.

Now, the presen invention will be described in detail with reference to Examples. However, it should be understood that the present invention is by no means restricted by these specific Examples. In Examples or in Reference Examples, the symbols "NMR" and "MS" indicate "nuclear magnetic resonance spectrum" and "mass spectrometry". In the NMR data, only the characteristic absorptions are given. Likewise, in the MS data, only the principal peaks or typical fragment peaks are given.

In this specification, "Me" means a methyl group, "Et" an ethyl group, "Pr" a propyl group, "Ac" a acetyl group, "Bu" a butyl group, and "Pen" a pentyl group. Likewise, a "n" indicates normal, "i" indicates iso, "sec" indicates secondary and "t" indicates tertiary.

REFERENCE EXAMPLE 1

Among the phenols used in the Examples, those not available as commercial products were prepared in accordance with the following methods 1-(i) to 1-(viii).

1-(i) 2-Ethyl-4-methoxycarbonylphenol

A mixture comprising 24.4 g of 2-ethylphenol, 40 g of carbon tetrachloride, 120 ml of a 50% sodium hydroxide aqueous solution and 1.0 g of copper powder was refluxed under stirring for 8 hours. After cooling, the brown reaction mixture was acidified with concentrated hydrochloric acid and extracted with ethyl acetate. The extract was treated with activated charcoal (5 g) and silica gel (30 g), and the filtrate was extracted with a saturated sodium hydrogen carbonate aqueous solution. The extract was acidified by gradually adding an aqueous hydrochloric acid solution to the extract under cooling with ice, and then extracted with ethyl acetate. The extract was washed sequentially with water and a saturated sodium chloride aqueous solution, and dried over sodium sulfate. Then, the solvent was distilled off to obtain 12.38 g of 2-ethyl-4-carboxyphenol as a reddish purple solid substance.

3.50 g of this product was dissolved in 60 ml of a 10% hydrogenchloride methanol solution, and the solution was stirred at room temperature for 2 days. The solvent was distilled off, and the residual oily substance thereby obtained was extracted with ethyl acetate. The extract was washed sequentially with an aqueous sodium hydrogen carbonate solution, water and a saturated sodium chloride aqueous solution, and dried over sodium sulfate. Then, the solvent was distilled off to obtain a dark reddish purple oily substance. This substance was dissolved in chloroform, and treated by active carbon (5 g) and silica gel (20 g). Then, the solvent of the filtrate was distilled off to obtain 2.70 g of the above identified compound as a light reddish purple solid substance.

NMR(CDCl$_3$)$\delta$: 7.84(1H, d), 7.79(1H, dd), 6.83 (1H, d), 6.6–5.8 (1H, boards, disappeared upon the addition of D$_2$O), 3.87(3H, s), 2.68(2H, q), 1.23(3H, t).

In the same manner as above, 2-i-propyl-4-methoxycarbonylphenol, 2-ethoxy-4-methoxycarbonylphenol and 2-sec-butyl-4-methoxycarbonylphenol were prepared from 2-i-propylphenol, 2-ethoxyphenol and 2-sec-butylphenol, respectively.

1-(ii) 2-Allyl-4-cyanophenol

A mixture comprising 29.75 g of 4-cyanophenol, 33.27 g of allyl bromide, 41.46 g of potassium carbonate and 350 ml of acetone, was refluxed under stirring for 4 hours. Acetone was distilled, and water was added to the residue. The mixture was extracted with benzene. The benzene layer was washed sequentially with a 5% sodium hydroxide aqueous solution and water, and dried over sodium sulfate. Then, the solvent was distilled off to obtain a pale yellow oily substance. The residual substance was crystallized from n-hexane-ethyl ether to obtain 38.16 g of 4-allyloxy benzonitrile as colorless crystals having a melting point of from 40.5° to 41° C.

38.16 g of this allyloxy compound was stirred at a temperature of from 195° to 200° C. for 15 hours. After cooling, the dark orange oily reaction product was extracted with a 5% sodium hydroxide aqueous solution. The extract was washed with benzene, and acidified with concentrated hydrochloric acid to a pH of about 2, and then extracted with ethyl ether. The ethyl ether extract was washed sequentially with water and a saturated sodium chloride aqueous solution. Then, the solvent was distilled off to obtain a dark orange substance. The residue was dissolved in 200 ml of heated benzene and treated with silica gal (50 g). The solvent of the filtrate was distilled off, and a pale yellow oily substance thereby obtained was crystallized from ethyl ether-n-hexane to obtain 24.90 g of the above identified compound as colorless crystals having a melting point of from 83° to 83.5° C.

NMR(CDCl$_3$)$\delta$: 7.5–7.2(2H, m), 6.80(1H,d), 6.9–6.3(1H, broad s, disappeared upon the addition of D$_2$O), 6.3–5.6(1H, m), 5.3–4.8(2H, m), 3.35(2H, d).

In the same as above, 2-allyl-4-methoxyphenol (oily substance), 2-allyl-4-methoxycarbonylphenol (crystals, melting point: 85°–88° C.) and 2-allyl-4-ethoxycarbonylphenol were prepared from 4-methoxyphenol, p-hydroxybenzoic acid methyl ester and p-hydroxybenzoic acid ethyl ester, respectively.

1-(iii) 2-n-Propyl-4-cyanophenol

A mixture of 8.15 g of 2-allyl-4-cyanophenol prepared in Reference Example 1-(ii), 1.5 g of 5% palladium-carbon and 100 ml of methanol, was stirred in a hydrogen stream for 2.5 hours. The catalyst was removed by filtration, and the solvent was distilled off from the filtrate to obtain 7.30 g of the above identified compound as a colorless oily substance.

NMR(CDCl$_3$)$\delta$: 7.4–7.2(2H, m), 6.76(1H, d), 6.36(1H, broad, s), 2.58(2H, t), 1.95–1.25(2H, m), 0.95(3H, t).

In the same manner as above, 2-n-propyl-4-methoxyphenol (oily substance), 2-n-propyl-4-methoxycarbonylphenol (crystals) and 2-n-propyl-4-ethoxycarbonylphenol were prepared from 2-allyl-4-methoxyphenol, 2-allyl-4-methoxycarbonylphenol and 2-allyl-4-ethoxycarbonylphenol prepared in Reference Example 1-(ii), respectively.

1-(iv) 2-Ethyl-4-formylphenol 45.5 g of titanium tetrachloride was dropwise added, under stirring with ice, to a solution obtained by dissolving 14.64 g of 2-ethylphenol in 200 ml of dichloromethane. After the completion of the dropwise addition, 22.76 g of $\alpha,\alpha$-dichloromethyl methyl ether was dropwise added thereto. The ice bath was removed, and the reaction solution was stirred at room temperature for 2 hours. Then, the reaction solution was poured into a 10% hydrochloric acid aqueous solution, and the mixture was stirred for 2 hours. The reaction mixture was extracted with chloroform. The chloroform layer was washed with water, and then extracted with a 10% sodium hydoxide aqueous solution. The alkali extract layer was washed twice with chloroform, and then acidified to a pH of about 2 by gradually adding concentrated hydrochloric acid. Then, the mixture was extracted with ethyl acetate. The extract was washed sequentially with water and a saturated sodium chloride aqueous solution, and dried over sodium sulfate. Then, the solvent was distilled off to obtain a dark reddish purple oily substance. This product was purified by silica gel column chromatography by using benzene-ethyl acetate (16 : 1, v/v) as the developer, whereby 6.90 g of the above identified compound was obtained as a pale red oily substance.

NMR(CDCl$_3$)$\delta$: 9.74(1H, s), 7.65–7.49(2H, m), 7.57 (1H, s, disappeared upon the addition of D$_2$O), 6.88(1H, d), 2.69(2H, q), 1.25(3H, t).

1-(v) 2-n-Butyryl-4-bromophenol 25.0 g of n-butyryl chloride was dropwise added to a mixture comprising 38.06 g of 4-bromophenol, 19.75 g of pyridine and 500 ml of benzene under stirring and cooling with ice. After the completion of the dropwise addition, the reaction mixture was stirred at room temperature for 1 hour. Water was added to the reaction mixture, and the benzene layer was separated. The benzene layer was washed sequentially with water, 2% dilute hydrochloric acid, water and a aqueous sodium hydrogen carbonate solution, and dried over sodium sulfate. Then, the solvent was distilled off to obtain 53.5 g of 4-bromo-n-butyryl phenolate as a pale yellow oily substance.

A mixture of 53.5 g of the above ester and 38.1 g of aluminum chloride was heated under stirring, whereupon a vigorous exothermic reaction started. The oil bath was removed, and the stirring was continued until the foaming simmered down, and then the reaction system was stirred at 160° C. for 1 hour. After cooling, the formed dark brown solid substance was decomposed by 10% dilute hydrochloric acid and extracted with benzene. The benzene layer was washed twice with water, and dried over sodium sulfate. Then, the solvent was distilled off to obtain a brown oily substance. This substance was dissolved in 1 liter of a n-hexane-benzene mixture (10:1, v/v), and treated with 100 g of silica gel. Then, the solvent was distilled off from the filtrate to obtain a pale yellow oily substance. This substance was crystallized from n-hexane to obtain 30.29 g of the above identified compound as colorless crystals having a melting point of from 50.5° to 51° C.

NMR(CDCl$_3$)$\delta$: 12.30(1H, s, disappeared upon the addition of D$_2$O), 7.78(1H, d), 7.43 (1H, dd), 6.81(1h, d), 2.43(2H, t), 2.1–1.5(2H, m), 1.02(3H, t).

In the same manner as above, 2-n-valeryl-4-bromophenol (oily substance) was prepared.

1-(vi) 2-n-Butyl-4-methoxycarbonylphenol 14.84 g of ethyl chloroformate was dropwise added to a mixture comprising 27.69 g of 2-n-butyryl-4-bromophenol prepared in Reference Example 1-(v), 13.94 g of triethylamine and 200 ml of tetrahydrofuran over a period of 30 minutes under stirring and cooling with ice. After the completion of the dropwise addition, the reaction mixture was stirred at 0° C. for 30 minutes, and the formed triethylammonium chloride crystals were separated by filtration and washed with 100 ml of tetrahydrofuran. The filtrate and the washing solution were put together, and the solution thereby obtained was dropwise added to a mixture comprising 17.25 g of sodium borohydride and 300 ml of water under stirring and cooling with ice to maintain the internal temperature within a range of from 5° to 15° C. After the completion of the dropwise addition, the reaction mixture was stirred at room temperature for 1.5 hours. After the completion of the reaction, the reaction mixture was diluted with 200 ml of water and acidified by gradually adding concentrated hydrochloric acid. Then, the mixture was extracted with ethyl ether. The extract was washed sequentially with water and a saturated sodium chloride aqueous solution, and then dried over sodium sulfate. Then, the solvent was distilled off to obtain 31.12 g of 2-n-butyl-4-bromophenol as a pale yellow oily substance.

A mixture comprising 31.12 g of the above phenol, 18.81 g of benzyl bromide, 18.24 g of potassium carbonate and 300 ml of acetone, was stirred at room temperature for 2 days. Acetone was distilled off, and water was added to the residue. The mixture was extracted with benzene. The benzene layer was washed with a saturated sodium chloride aqueous solution, and dried over sodium sulfate. Then, the solvent was distilled off to obtain a pale yellow oily substance. This substance was subjected to silica gel column chromatography by using benzene-n-hexane (1:9, v/v) as the developer, whereby 30.07 g of (2-n-butyl-4-bromophenyl) benzyl ether was obtained as a colorless oily substance.

A solution obtained by dissolving 20.30 g of the bromobenzene derivative thus obtained and 13.85 g of ethyl bromide in 20 ml of dried ethyl ether, was dropwise added to a mixture comprising 5.41 of magnesium turnings and 100 ml of dried ethyl ether, under stirring. During the dropwise addition, heat generation occurred and the refluxing started. After the completion of the dropwise addition, reaction mixture was refluxed under stirring for 30 minutes on an oil bath. After cooling, excess magnesium was removed by decantation and washed with dried ethyl ether (25 ml×2). The Grignard reagent thus prepared, was dropwise added to a mixture comprising 50 g of pulverized solid of dry ice and 300 ml of dried tetrahydrofuran, under stirring. During the dropwise addition, 100 g of dry ice was further added. After the completion of the dropwise addition, the reaction mixture was stirred for further 2 hours. The reaction mixture was acidified by gradually adding a cooled 10% hydrochloric acid aqueous solution, and extracted with ethyl acetate. The extract was washed sequentially with water and a saturated sodium chloride aqueous solution, and dried over sodium sulfate. Then, the solvent was distilled off to obtain a pale yellow solid substance. This substance was washed with ethyl ether-n-hexane (1:1, v/v) to obtain 3.01 g of 3-n-butyl-4-benzyloxy benzoic acid as colorless solid.

4.19 g of the benzoic acid derivative thus obtained, was dissolved in a mixture of 50 ml of ethyl acetate and 100 ml of methanol under heating. Then, diazomethane gas was introduced into this solution until the solution turned pale yellow. The reaction solution was left to stand overnight, and then the solvent was distilled off to obtain 4.38 g of methyl 3-n-butyl-4-benzyloxy benzoate as a colorless oily substance.

A mixture comprising 4.38 g of the benzoate thus obtained, 500 mg of 5% palladium-carbon and 60 ml of methanol, was stirred in a hydrogen stream for 3 hours. The catalyst was separated by filtration, and the solvent was distilled off from the filtrate to obtain a pale yellow solid, which was crystallized from ethyl ether-n-hexane to obtain 2.69 g of the above identified compound as colorless crystals having a melting point of from 78° to 81° C.

NMR(CDCl$_3$)$\delta$: 7.8–7.6(2H, m), 6.76(1H, d), 6.22(1H, s, disappeared upon the addition of D$_2$O), 3.85(3H, s), 2.62(1H, collapsed t), 2.1–1.0(4H, m), 0.91(3H, collapsed t).

In the same manner as above, 2-n-pentyl-4-methoxycarbonylphenol (crystals, melting point: 82.5°–83.5° C.) was prepare from 2-n-valeryl-4-bromophenol obtained in Reference Example 1-(v).

1-(vii) 2-n-Propyl-4-cyanothiophenol 3.28 g of 2-n-propyl-4-cyanophenol prepared in Reference Example 1-(iii) was dissolved in 40 ml of N,N-dimethylformamide. Then, 1.07 g of sodium hydride was added under stirring and cooling with ice, and the mixture was stirred for 30 minutes. Then, 2.65 g of dimethylthiocarbamoyl chloride was gradually added, and the mixture was stirred at 0° C. for 1.5 hours. 50 ml of ice water was poured into the reaction mixture, and the mixture was extracted with ethyl acetate. The extract was washed with a saturated sodium chloride aqueous solution, and dried over sodium sulfate. Then, the solvent was distilled off to obtain a pale yellow solid substance. The solid substance was purified by silica gel column chromatography by using benzene as the developer, whereby 4.14 g of 2-n-propyl-4-cyano-dimethylthiocarbamoyl phenolate was obtained as a pale yellow oily substance.

4.00 g of the carbamate thus obtained, was stirred at 205° C. for 13 hours. After cooling, the formed dark brown solid substance was exracted with ethyl acetate, and the solvent was distilled off from the extract. The dark brown solid substance thus obtained was treated with ethyl ether under cooling with ice to obtain 2.90 g of 2-n-propyl-4-cyano-dimethylcarbamoyl thiophenolate as a pale brown powder.

A mixture comprising 2.86 g of the thiophenolate thus obtained, 30 ml of dried methanol and 3.0 ml of a 28% sodium methoxide methanol solution, was stirred at room temperature for 15 hours. Then, 1.5 ml of a 28% sodium methoxide methanol solution was added, and the mixture was stirred for further 5 hours. The reaction mixture was acidified to a pH of about 2 by gradually adding concentrated hydrochloric acid thereto, and then the solvent was distilled off. Water was poured into the dark brown oily residue thus obtained, and the mixture was extracted with benzene. The benzene layer was washed sequentially with water and a saturated sodium chloride aqueous solution, and dried over sodium sulfate. Then, the solvent was distilled off to obtain a dark brown oily substance. The oily substance was purified by silica gel column chromatograph by using benzene-n-hexane (2:1, v/v) as the developer, whereby 1.13 g of the above identified compound was obtained as a colorless oily substance.

NMR(CDCl$_3$)$\delta$: 7.4–7.2(3H, m), 3.51(1H, s, disappeared upon the addition of D$_2$O), 2.61(2H, t), 2.0–1.3(2H, m), 0.99(3H, t).

REFERENCE EXAMPLE 1-(viii)

2-Ethyl-4-methoxyphenol: This compound was prepared from 2,5-dimethoxyacetophenone in accordance with the method disclosed in a literature [J. Chem. Soc., 1922(1939) and J. Chem. Soc., (C), vol 24, 2274(1966)].

2-Chloro-4-methoxycarbonylphenol, 2-chloro-4-ethoxycarbonylphenol, and 2-methoxy-4-ethoxycarbonylphenol: These compounds were prepared from commercially available 2-chloro-4-carboxyphenol and 3-methoxy-4-hydroxybenzoic acid in accordance with a method similar to the esterification method as disclosed in Reference Example 1-(i).

Ethyl 7-hydroxy-8-n-propyl-4-oxo-4H-l-benzopyran-2-carboxylate, and 2-hydroxy-3-n-propyl-4-hydroxyacetophenone: These compounds were prepared in accordance with a method disclosed in a literature [J. Med. Chem., vol 20, 371(1977)].

Methyl 4-hydroxy-$\gamma$-oxobenzene butanoate: This compound was prepared in accordance with a method disclosed in Example 1 of Japanese Unexamined Patent Publication No. 139342/1984.

REFERENCE EXAMPLE 2

4-Ethyl-5-chloro-2-t-butyl-3(2H)pyridazinone

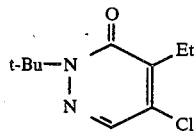

Into a four-necked flask of 1 liter, 43 g of ethylmagnesium bromide (3 mol/liter of an ether solution) and 200 ml of dehydrated toluene were charged. While thoroughly stirring the mixture at room temperature, 22.1 g (0.1 mol) of 2-t-butyl-4,5-dichloro-3(2H)pyridazinone was added in three portions. The reaction temperature was raised to a level of about 60° C., and the stirring was continued for about 30 minutes. The disappearance of the starting material dichloropyridazinone was confirmed by thin layer chromatography (developer: hexane-acetone=20:1, v/v), whereupon the reaction was terminated. After the addition of about 300 ml of chilled water, the mixture was stirred vigorously, and transferred to a separating funnel, and then the aqueous layer was removed. The organic layer was washed with about 200 ml of water, and dried over anhydrous sodium sulfate, and then the solvent was distilled off. The pale brown oily substance thereby obtained was purified by silica gel column chromatography (developer: benzene) to obtain pale yellow crystals. 14.5 g (yield: 67.6%).

mp: 61.5°–62.5° C.

NMR(CDCl$_3$)$\delta$: 7.62 (1H, s), 2.72 (2H, q), 1.61 (9H, s), 1.14 (3H, t).

In the same manner as above, the following compounds were prepared from the corresponding 2-alkyl-4,5-dichloro-3(2H)pyridazinones and alkyl magnesium halides: 4-Methyl-5-chloro-2-t-butyl-3(2H) pyridazinone [oily substance, boiling point: 60°–62° C. (0.22 mmHg)], 4-n-propyl-5-chloro-2-t-butyl-3(2H) pyridazinone (oily substance), 4-n-butyl-5-chloro-2-t-butyl-3(2H)pyridazinone (only substance) and 4-n-pentyl-5-chloro-2-t-butyl-3(2H)pyridazinone (oily substance).

REFERENCE EXAMPLE 3

4-Chloro-5-(3-chloropropyloxy)-2-t-butyl-3(2H) pyridazinone

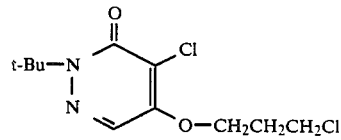

A mixture comprising 5.0 g of 4-chloro-5-hydroxy-2-t-butyl-3(2H)pyridazinone, 4.2 g of 1-bromo-3-chloropropane, 3.7 g of anhydrous potassium carbonate and 30 ml of dimethylformamide, was stirred at a temperature of from 70° to 80° C. for 3 hours. The reaction mixture was transferred to separating funnel, and 100 ml of water and 50 ml of benzene were added thereto. The mixture was shaked vigorously, and the benzene layer was washed with water and dried over anhydrous sodium sulfate. Then, the solvent was distilled off, and the oily substance thereby obtained was dissolved in hexane-ethyl ether (3:1, v/v), and precipitated crystals were collected by filtration and dried to obtain 5.7 g of the above identified compound having a melting point of from 51° to 52° C.

NMR(CDCl$_3$)$\delta$: 7.79(1H, s), 4.39(2H, t), 3.77(2H, t), 2.28(2H, m), 1.62(9H, s).

In the same manner as above, the following compounds were prepared from the corresponding 4-chloro-5-hydroxy2-alkyl-3(2H)pyridazinones:

4-chloro-5-(3-chloropropyloxy)-2-i-propyl-3(2H)pyridazinone (crystals, melting point: 88°–90° C.), 4-chloro-5-(3-chloropropyloxy)-2-ethyl-3(2H)pyridazinone (crystals, melting point: 73° C.).

Further, by using 1-bromo-2-chloroethane instead of 1-bromo-3-chloropropane, 4-chloro-5-(2-chloroethyloxy)-2-i-propyl-3(2H)pyridazinone (crystals, melting point: 100°–103° C.) was prepared from 4-chloro-5-hydroxy-2-i-propyl-3(2H)pyridazinone.

REFERENCE EXAMPLE 4

4-Chloro-5-(3-hydroxypropylamino)-2-t-butyl-3(2H)pyridazinone

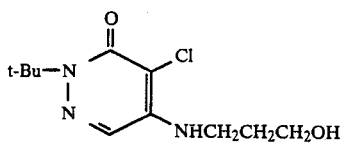

A mixture comprising 4.42 g of 4,5-dichloro-2-t-butyl-3(2H)pyridazinone, 4.50 g of 3-amino-1-propanol, 4.15 g of potassium carbonate, 25 ml of 1,4-dioxane and 80 ml of water, was refluxed under stirring for 18 hours. 1,4-Dioxane was distilled off under reduced pressure, and the residue thereby obtained was extracted with ethyl acetate. The extract was washed sequentially with dilute hydrochloric acid, water and a saturated sodium chloride aqueous solution, and dried over sodium sulfate. Then, the solvent was distilled off to obtain a pale yellow viscous oily substance. The oily substance was purified by silica gel column chromatography, whereby 3.54 g of the above identified compound was obtained from the chloroform-methanol (20:1, v/v) eluate as a pale yellowish orange viscous oily substance.

NMR(CDCl$_3$)δ: 7.52(1H, s), 5.25(1H, broad s), 3.79(2H, t), 3.45(2H, m), 1.88(2H, m), 1.60(9H, s).

MS(m/e): 259(M+), 203, 158(100%).

In the same manner as above, the following compounds were prepared from the corresponding 4,5-dichloro- and 4,5-dibromo-2-alkylpyridazinones:

4-Bromo-5-(3-hydroxypropylamino)-2-t-butyl-3(2H)pyridazinone (viscous oily substance), 4-chloro-5-(3-hydroxypropylamino)-2-i-propyl-3(2H)pyridazinone (viscous oily substance), 4-bromo-5-(3-hydroxypropylamino)-2-i-propyl-3(2H)pyridazinone (viscous oily substance), 4-chloro-5-(3-hydroxypropylamino)-2-ethyl-3(2H) pyridazinone (crystals, melting point: 86°–87° C.) and 4-bromo-5-(3-hydroxypropylamino)-2-ethyl-3(2H) pyridazinone (crystals, melting point: 83° C.).

Further, by using 2-amino-ethanol instead of 3-amino-1-propanol, 4-bromo-5-(2-hydroxyethylamino)-3(2H) pyridazinone (crystals, melting point: 121°–123° C.) was prepared from 4,5-dibromo-2-i-propyl-3(2H)pyridazinone.

REFERENCE EXAMPLE 5

4-Chloro-5-(2-oxiranylmethoxy)-2-i-propyl-3(2H) pyridazinone

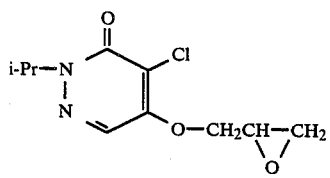

1.3 g of potassium hydroxide was dissolved in a solvent mixture of 6 ml of ethanol and 0.12 ml of water. To this solution, 4.0 g of 2-i-propyl-4-chloro-5-hydroxy-3(2H)pyridazinone was added. Then, a solution obtained by dissolving 5.9 g of epichlorohydrin in 3.4 ml of ethanol, was added thereto, and the mixture was refluxed for about 3.5 hours. After the completion of the reaction, the solvent was distilled off, and water and ethyl ether were added to the residue in an amount of 30 ml each. The mixture was vigorously shaken. The organic layer was washed once with water, and dried over anhydrous sodium sulfate. The solvent was distilled, and the residue thereby obtained, was extracted three times with 30 ml of n-hexane-ethyl ether (1:1, v/v). The extract was concentrated to obtain 2.3 g of the above identified compound as colorless crystals having a melting point of from 92° to 95° C.

MS (m/e): 244(M+), 202, 57(100%).

In the same manner as above, 4-chloro-5(2-oxiranylmethoxy)-2-ethyl-3(2H)pyridazinone (crystals) was prepared from 4-chloro-5-hydroxy-2-ethyl-3(2H) pyridazinone.

REFERENCE EXAMPLE 6

4-Chloro-5-(2,3-dihydroxypropylamino)-2-i-propyl-3(2H) pyridazinone

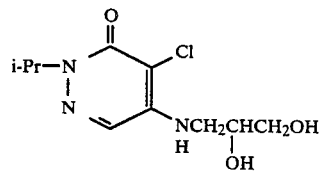

A mixture comprising 5.18 g of 4,5-dichloro-2-i-propyl-3(2H)pyridazinone, 7.97 g of 2,3-dihydroxypropylamine, 8 ml of 1,4-dioxane and 80 ml of water, was stirred at a temperature of from 75° to 80° C. for 17 hours. Most 1,4-dioxane was distilled off under reduced pressure, and the reaction mixture was acidified to a pH of about 2 by adding dilute hydrochloric acid, and sodium chloride was added to the saturation. Then, the mixture was extracted with tetrahydrofuran (200 ml×2). The extract was washed with a saturated sodium chloride aqueous solution, and dried over sodium sulfate. Then, the solvent was distilled off to obtain a colorless solid substance. The solid substance was crystallized from ethyl acetate-ethyl ether to obtain 5.30 g of the above identified compound as colorless crystals having a melting point of from 137° to 139° C.

NMR(CDCl$_3$+DMSO-d$_6$)δ: 7.74(1H, s), 5.75–4.80(2H, m), 4.62(1H, d, disappeared upon the addition of D$_2$O), 4.4–4.0 (1H, broad t, disappeared upon the addition of D$_2$O), 4.0–3.2(5H, m), 1.29(6H, d).

MS (m/e): 261(M+), 219, 200, 158(100%).

In the same manner as above, 4-chloro-5(2,3-dihydroxypropylamino)-2-ethyl-3(2H)pyridazinone (crystals, melting point: 120°–124° C.) was prepared from 4,5-dichloro-2-ethyl-3(2H)pyridazinone.

REFERENCE EXAMPLE 7

2-t-Butyl-4-n-propyl-5-(3-hydroxypropylamino)-3(2H) pyridazinone

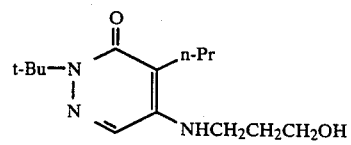

A mixture comprising 14.0 g of 2-t-butyl-4-n-propyl-5-chloro-3(2H)pyridazinone, 44 g of 3-hydroxypropylamine and 14.8 g of anhydrous potassium carbonate, was stirred at a temperature of from 145° to 155° C. for 12.5 hours. The reaction solution was returned to room temperature, and about 200 ml of cold water was added. The mixture was stirred. The precipitated white crystals were collected by filtration, and dried to obtain 12.1 g of the above identified compound having a melting point of from 167° to 169° C.

NMR(CDCl$_3$)δ: 7.49(1H, s), 4.91(1H, broad s), 4.13 (1H, t), 3.73(2H, t), 3.33(2H, m), 2.41(2H, t), 2.15–1.20(4H, m), 1.59 (9H, s), 0.94(3H, t).

In the same manner as above, 2-t-butyl-4-n-butyl-5-(3-hydroxypropylamino)-3(2H)pyridazinone (crystals, melting point: 106°–108° C.) and 2-t-butyl-4-n-pentyl-5-(3-hydroxypropylamino)-3(2H)pyridazinone (oily substance) were prepared from the corresponding 2-t-butyl-4-alkyl-5-chloro-3(2H)pyridazinones prepared in Reference Example 2.

REFERENCE EXAMPLE 8

3-(2-Ethoxycarbonyl-8-n-propyl-4-oxo-4H-1-benzopyran-7-yloxy)propylbromide

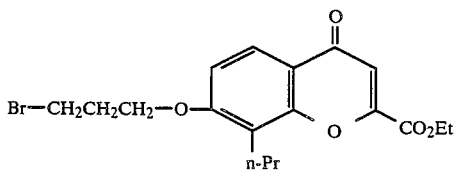

A mixture comprising 5.52 g of ethyl 7-hydroxy-8-n-propyl-4-oxo-4H-1-benzopyran-2-carboxylate [J. Med. Chem., 20, 371 (1977)], 2.76 g of potassium carbonate, 12.12 g of 1,3-dibromopropane and 30 ml of dimethylformamide was stirred at a temperature of from 60° to 70° C. for 4 hours. The reaction mixture was added to 60 ml of ethyl acetate and 70 ml of water, and the mixture was vigorously shaken. The organic layer was washed with water, and dried over anhydrous sodium sulfate. The solvent was distilled off, and crude crystals thereby obtained was recrystallized from benzene-ethyl acetate (2:1, v/v) to obtain 5.4 g of the above identified compound.

NMR(CDCl$_3$)δ: 8.02(1H, d, J=9.0 Hz), 7.01(1H, d, J=9.0 Hz), 4.42(2H, q), 4.24(2H, t), 3.12(2H, t), 2.90(2H, t) 2.48(2H, t), 1.90–1.50(2H, m), 1.42(3H, t), 0.96(3H, t).

In the same manner as above, 3-(3-methoxyphenoxy) propylbromide [oily substance, boiling point: 102°–105° C. (1.0 mmHg)], and 3-(2-chloro-4-ethoxycarbonylphenoxy) propylbromide (oily substance) were prepared from 3-methoxyphenol and 2-chloro-4-ethoxycarbonylphenol, respectively.

Further, by using 1,4-dibromobutane instead of 1,3-dibromopropane, 4-(2-bromophenoxy)butylbromide (oily substance) was prepared from 2-bromophenol.

EXAMPLE 1

4-Chloro-5-[2-(4-methoxyphenyl)ethylamino]-2-ethyl-3(2H)pyridazinone (Compound No. 20)

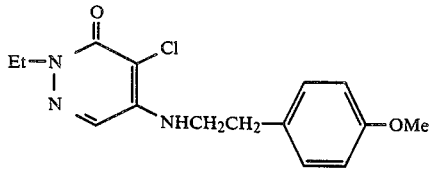

A mixture comprising 0.5 g of 4,5-dichloro-2-ethyl-3(2H)pyridazinone, 1.18 g of 4-methoxyphenylethylamine, 0.36 g of potassium carbonate, 18 ml of water and 6 ml of 1,4-dioxane, was refluxed under stirring for 8 hours. Then, 1,4-dioxane was distilled off under reduced pressure, and the residue thereby obtained was extracted with ethyl acetate. The extract was washed sequentially with dilute hydrochloric acid and water, and dried over sodium sulfate. Then, solvent was distilled off. The residue was purified by silica gel column chromatography by using benzene-ethyl acetate (1:1, v/v) as the developer, whereby 400 mg of the above identified compound was obtained as colorless crystals having a melting point of from 135° to 135.5° C.

NMR(CDCl$_3$)δ: 7.54(1H, s), 7.15, 6.86(each 2H, ABq), 4.78(1H, broad s), 4.18(2H, q), 3.80 (3H, s), 3.55(2H, q), 2.90(2H, t), 1.35(3H, t).

MS (m/e): 307(M$^+$), 186, 121(100%).

EXAMPLE 2

4-Chloro-5-[3-(2-chloro-4-ethoxycarbonylphenoxy)propoxy]-2-ethyl-3(2H)pyridazinone (Compound No. 30)

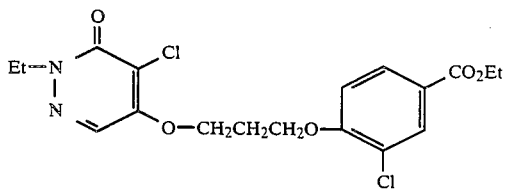

A mixture comprising 1.36 g of 3-(2-chloro-4-ethoxycarbonylphenoxy)propylbromide prepared from 2-chloro-4-ethoxycarbonylphenol and 1,3-dibromopropane in Reference Example 8, 0.74 g of 2-ethyl-4-chloro-5-hydroxy-3(2H) pyridazinone, 0.64 g of anhydrous potassium carbonate and 5 ml of N,N-dimethylformamide, was stirred at a temperature of from 70° to 80° C. for about 4 hours. To the reaction mixture, 50 ml of water was added, and the mixture was vigorously stirred, and then transferred to a separating funnel. Then, the mixture was extracted with 50 ml of benzene, the extract was washed once with a 2% hydrochloric acid aqueous solution and once with water, and then dried over anhydrous magnesium sulfate.

The solvent was distilled off, and the crystals thereby obtained were recrystallized from hexane-ethyl acetate to obtain 1.14 g of the above identified compound as colorless crystals having a melting point of from 101° to 103° C.

IR($\nu_{max}^{KBr}$)cm$^{-1}$: 1719, 1639, 1598, 1310, 1265.

NMR(CDCl$_3$)δ: 8.04(1H, d), 7.92(1H, dd), 6.96(1H, d), 7.86(1H, s), 4.60–4.06(8H, m), 2.40(2H, t), 1.38(3H, t), 1.35(3H, t).

MS (m/e): 414(M$^+$; 100%), 342, 187.

EXAMPLE 3

4-Chloro-5-[3-(2-n-propyl-3-hydroxy-4-acetylphenoxy)propoxy]-2-t-butyl-3(2H)pyridazinone (Compound No. 37)

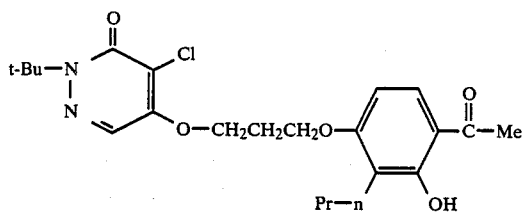

A mixture comprising 1.0 g of 4-chloro-5-(3-chloropropyloxy)-2-t-butyl-3(2H)pyridazinone obtained in Reference Example 3, 0.7 g of 2,4-dihydroxy-3-n-propylacetophenone, 1.0 g of anhydrous potassium carbonate, 0.6 g of potassium iodide and 5 ml of dimethylformamide, was stirred at a temperature of from 70° to 80° C. for 3 hours. To the reaction mixture, 20 ml of water and 20 ml of benzene were added, and the mixture was vigorously shaked. The benzene layer was washed with water and dried over anhydrous sodium sulfate. The solvent was distilled off and the oily substance thereby obtained was separated and purified by silica gel column chromatography (developer: hexane-ethyl acetate=2:1, v/v) to obtain 0.92 g of the above identified compound as a pale yellow oily substance.

NMR(CDCl$_3$)δ: 8.79(1H, s), 7.63(1H, d), 6.48(1H, d), 4.45(2H, t), 4.26(2H, t), 264(2H, t), 2.35(2H, t), 2.54(3H, s), 1.65(9H, s).

MS (m/e): 401(M+-Cl), 345(100%), 205.

EXAMPLE 4

4-Chloro-5-[3-(4-methylphenylsulfonyloxy)propylamino]-2-t-butyl-3(2H)pyridazinone (Compound No. 15)

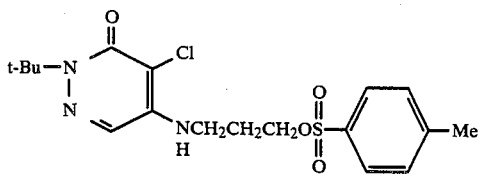

2.55 g of p-toluenesulfonyl chloride was added to a mixture comprising 3.16 g of 4-chloro-5-(3-hydroxypropylamino)-2-t-butyl-3(2H) pyridazinone prepared in Reference Example 4, 1.44 g of pyridine and 50 ml of dichloromethane under stirring and cooling with ice, and the mixture was stirred at the same temperature for 2 hours. Then, 2.0 g of pyridine and 2.5 g of p-toluenesulfonyl chloride were added to the reaction mixture in this order. The mixture was stirred for further 2 hours under cooling with ice, and left to stand overnight in an ice chamber. The solvent was distilled off, and the pale yellow oily substance thereby obtained was extracted with benzene. The extract was washed sequentially with dilute hydrochloric acid, water (twice) and a saturated sodium chloride aqueous solution, and dried over sodium sulfate. Then, solvent was distilled off to obtain a pale yellow oily substance. The oily substance was purified by silica gel column chromatography by using benzene-ethyl acetate (1:1, v/v) as the developer, to obtain 4.67 g of the above identified compound as a pale yellow viscous oily substance.

NMR(CDCl$_3$)δ: 7.72, 7.26(each 2H, AB q), 7.37(1H, s), 4.60(1H, broad s), 4.10(2H, t), 3.38(2H, m), 2.41(3H, s), 1.96(2H, m), 1.60(9H, s).

MS (m/e): 413(M+), 357(100%), 322, 158, 150.

EXAMPLE 5

4-Chloro-5-[3-(2-n-propyl-4-cyanophenoxy)propylamino]-2-t-butyl-3(2H)pyridazinone (Compound No. 1)

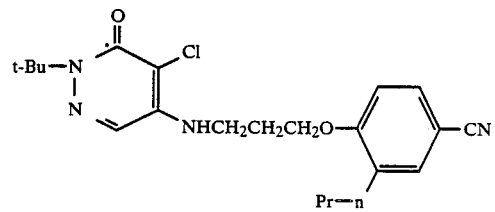

A mixture comprising 1.24 g of Compound No. 15 prepared in Example 4, 0.53 g of 2-n-propyl-4-cyanophenol, 150 mg of sodium iodide, 1.04 g of potassium carbonate and 30 ml of 2-butanone, was refluxed under stirring for 5 hours. The solvent was distilled off, and water was added to the residue thereby obtained. The mixture was extracted with chloroform. The extract was washed sequentially with a 5% sodium hydroxide aqueous solution and a saturated sodium chloride aqueous solution, and dried over sodium sulfate. Then, the solvent was distilled off to obtain a pale yellowish orange viscous oily substance. The residual oily substance was crystallized from ethyl ether-benzene-hexane to obtain 0.83 g of the above identified compound as colorless crystals having a melting point of from 96° to 97° C.

IR($\nu_{max}^{KBr}$)cm$^{-1}$: 3345, 2225, 1630(shoulder), 1605–1615.

NMR(CDCl$_3$)δ: 7.53(1H, s), 7.42(1H, dd), 7.36(1H, d), 6.82(1H, d), 4.80(1H, broad s), 4.12(2H, t), 3.57(2H, m), 2.62(2H, t), 2.38–1.45 (4H, m), 1.61(9H, s), 0.95(3H, t).

MS (m/e): 402(M+), 346, 311(100%), 159.

EXAMPLE 6

4-Chloro-5-{3-[2-n-propyl-4-(1H-tetrazol-5-ylphenoxy)]propylamino}-2-t-butyl-3(2H)pyridazinone (Compound No. 2)

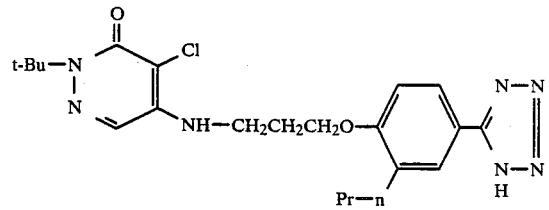

A mixture comprising 483 mg of Compound No. 1 prepared in Example 5, 390 mg of sodium azide, 385 mg of ammonium chloride and 5 ml of dimethylformamide, was stirred at 120° C. for 5 hours. The solvent was distilled off, and dilute hydrochloric acid was added to the residue thereby obtained. The mixture was extracted with ethyl acetate. The extract was washed sequentially with water and a saturated sodium chloride aqueous solution, and dried over sodium sulfate. The solvent was distilled off to obtain a pale yellow viscous oily substance. The oily substance was subjected to silica gel column chromatography, and the colorless solid substance obtained by eluting with chloroform-methanol (20:1, v/v) was crystallized from methanol-ethyl ether to obtain 263 mg of the above identified compound as colorless crystals having a melting point of from 189° to 190° C.

IR($\nu_{max}^{KBr}$)cm$^{-1}$: 3300, 1615, 1590.

NMR(CDCl$_3$+DMSO-d$_6$)δ: 7.95–7.70(2H, m), 7.61(1H, s), 6.92(1H, d), 4.12(2H, t), 3.80(2H, m), 2.68(2H, t), 2.4–2.0, 1.9–1.4(each 2H, m), 0.98(3H, t).

MS (m/e): 445(M+), 410, 354, 159, 143(100%).

EXAMPLE 7

4-Chloro-5-[3-(2-n-propyl-4-methoxycarbonylphenoxy)propylamino]-3(2H)pyridazinone (Compound No. 4)

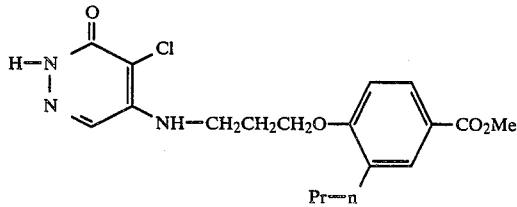

A mixture comprising 2.015 g of Compound No. 1 prepared in Example 5, 7.5 ml of sulfuric acid and 30 ml of methanol, was refluxed under stirring for 9.5 hours. Methanol was distilled off, and sodium hydrogen carbonate and water were gradually added to the pale brown residue thereby obtained, under cooling with ice, for neutralization. Then, the mixture was extracted with ethyl acetate. The extract was washed sequentially with water and a saturated sodium chloride aqueous solution, and dried over sodium sulfate. The solvent was distilled off to obtain a pale yellow oily substance. The residue was subjected to silica gel column chromatography, and the colorless viscous oily substance obtained by eluting with chloroform-methanol (3:1, v/v), was crystallized from chloroform-hexane to obtain 666 mg of colorless crystals having a melting point of from 164° to 166° C.

IR($\nu_{max}^{KBr}$)cm$^{-1}$: 3260, 1705, 1665, 1595.

NMR(CDCl$_3$)δ: 7.78(1H, dd), 7.76(1H, d), 7.59(1H, s), 6.76(1H, d), 4.99(1H, broad s), 4.12(2H, t), 3.84(3H, s), 3.59(2H, m), 2.63(2H, t), 2:45–1.40(4H, m), 0.95(3H, t).

MS (m/e): 379(M+; 100%), 190.

EXAMPLE 8

4-Chloro-5-[3-(2-n-propyl-4-methoxycarbonylphenoxy)propylamino]-2-ethyl-3(2H)pyridazinone (Compound No. 6)

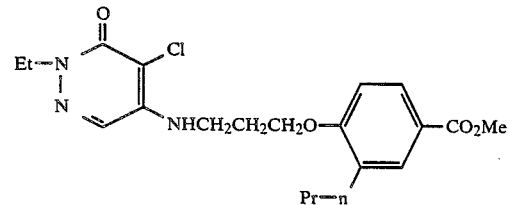

A mixture comprising 456 mg of Compound No. 4 prepared in Example 7, 207 mg of potassium carbonate, 0.5 ml of ethyl iodide and 5 ml of N,N-dimethylformamide, was stirred at 60° C. for 2 hours. The solvent was distilled off, and water was added to the pale brown oily substance thereby obtained. The mixture was extracted with ethyl acetate. The extract was washed with water, and dried over sodium sulfate. Then, the solvent was distilled off to obtain a pale yellow oily substance. The oily substance was subjected to silica gel column chromatography, and 480 mg of the above identified compound was obtained as a pale yellow semi-solid substance from the eluate with chloroform-methanol (30:1, v/v).

NMR(CDCl$_3$)δ: 7.83(1H, dd), 7.77(1H, d), 7.55(1H, s), 6.78(1H, d), 4.80(broad s), 4.40–3.90 (4H, m), 3.84(3H, s) 3.80–3.45(2H, m), 2.63(2H, t), 2.40–2.00, 1.90–1.45(each 2H, m), 1.32(3H, t), 0.96(3H, t).

MS(m/e): 407(M+), 372, 340, 187(100%).

EXAMPLE 9

4-Chloro-5-[3-(2-n-propyl-4-carboxyphenoxy)propylamino]-2-ethyl-3(2H)pyridazinone (Compound No. 7)

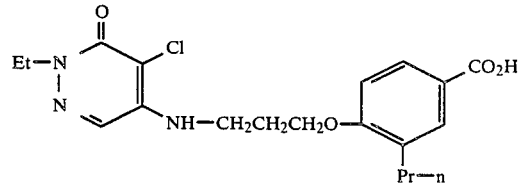

A mixture comprising 370 mg of Compound No. 6 prepared in Example 8, 10 ml of methanol and 1.0 ml of a 2N sodium hydroxide aqueous solution, was refluxed for 1.5 hours. Then, 0.5 ml of a 2N sodium hydroxide aqueous solution was further added thereto, and the refluxing was continued for 30 minutes. After cooling, the reaction mixture was acidified to a pH of about 7.0 by adding dilute hydrochloric acid thereto, and then the solvent was distilled off. Dilute hydrochloric acid was poured into the residue thereby obtained, and the mixture was extracted with ethyl acetate. The extract was washed with water and a saturated sodium chloride aqueous solution, and dried over sodium sulfate. Then, the solvent was distilled off to obtain a pale yellow solid substance. The solid substance was recrystallized twice from methanol-ether to obtain 160 mg of the above identified compound as colorless crystals having a melting point of from 164° to 165° C.

NMR(CDCl$_3$)δ: 8.0–7.7(2H, m), 7.52(1H, s), 6.75(1H, d), 4.90(1H, broad s), 4.4–3.9(4H, m), 3.8–3.3(2H, m), 2.63(2H, t), 2.3–1.5 (4H, m), 1.32(3H, t), 0.97(3H, t).

MS(m/e): 393(M+), 358, 187(100%).

EXAMPLE 10

4-Chloro-5-[3-(2-n-propyl-4-carbamoylphenoxy)-propylamino]-2-i-propyl-3(2H)pyridazinone (Compound No. 42)

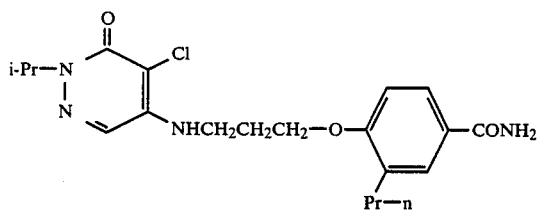

A mixture comprising 130 mg of Compound No. 41 i.e. 4 -chloro-5-[3-(2-n-propyl-4-carboxyphenoxy)-propylamino]-2-i-propyl-3(2H)pyridazinone, 62 mg of N,N'-carbonyldiimidazole and 20 ml of N,N-dimethylformamide, was stirred at room temperature for 1 hour, and then ammonia gas was bubbled into the mixture for 10 minutes under cooling with ice. The system was closed and left to stand at room temperature for 2 hours. Then, the solvent was distilled off under reduced pressure. The residue was extracted with chloroform, and the chloroform layer was washed sequentially with an aqueous sodium hydroxide solution and a dilute hydrochloric acid aqueous solution, and dried over sodium sulfate. Then, chloroform was distilled off. The residue was treated with ethyl ether to obtain 20 mg of the above identified compound as a white powder.

NMR(CDCl$_3$)δ: 7.89, 6.78(each 1H, ABq), 7.69(2H, s), 6.46(2H, broad s), 5.50–5.00(2H, m), 4.21(2H, t), 3.80–3.35(2H, m), 2.63 (2H, t), 1.85–1.15(2H, m), 1.30(6H, d), 0.93(3H, t).

IR($\nu_{max}^{KBr}$)cm$^{-1}$: 3350, 2950, 1610.

MS (m/e): 406(M$^+$), 312, 201(100%).

EXAMPLE 11

4-Chloro-5-[3-(2-n-propyl-4-cyanophenoxy)-2-hydroxypropoxy]-2-i-propyl-3(2H)pyridazinone (Compound No. 171)

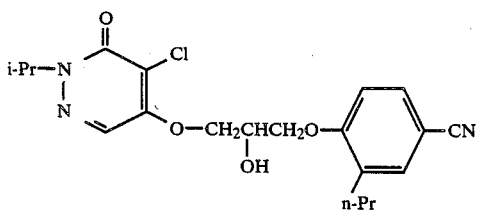

A mixture comprising 2.0 g of 4-chloro-5-(2-oxiranylmethoxy)-2-i-propyl-3(2H)pyridazinone prepared in Reference Example 5, 1.5 g of 2-n-propyl-4-cyanophenol, 1.35 g of potassium carbonate and 80 ml of diethyl ketone, was refluxed under stirring for 8 hours. Then, diethyl ketone was distilled off under reduced pressure, and the residue thereby obtained was extracted with ethyl acetate. The extract was washed with water and dried over sodium sulfate. Then, the solvent was distilled off. The residue was purified by silica gel column chromatography by using benzene-ethyl acetate (1:1, v/v) as the developer. The colorless crystals thereby obtained was recrystallized from ethyl ether to obtain 1.3 g of the above identified compound as colorless crystals having a melting point of from 118.5° to 121° C.

NMR(CDCl$_3$)δ: 7.92(1H, d), 7.46(1H, dd), 7.40(1H, s), 6.90(1H, d), 5.58–4.95(1H, m), 4.62–4.06(5H, m), 3.72–3.46(1H, m), 2.59 (2H, t), 2.00–1.26(2H, m), 1.42(6H, d), 0.92(3H, t).

MS (m/e): 405(M$^+$), 328, 189(100%), 147.

EXAMPLE 12

4-Chloro-5-[3-(4-methylphenylsulfonyloxy)-2-hydroxypropylamino]-2-i-propyl-3(2H)pyridazinone (Compound No. 143)

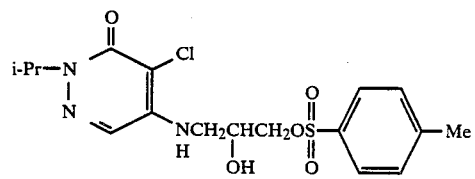

1.60 g of p-toluenesulfonyl chloride was added to a mixture comprising 2.09 g of 4-chloro-5-(2,3-dihydroxypropylamino)-2-i-propyl-3(2H)pyridazinone prepared in Reference Example 6, 12 ml of pyridine and 20 ml of dichloromethane, under cooling with ice. The mixture was stirred for 6 hours, and then left to stand for 2 days in an ice chamber. The reaction mixture was acidified to a pH of about 2 by adding cooled dilute hydrochloric acid, and the mixture was extracted with ethyl acetate. The extract was washed sequentially with water, a saturated sodium hydrogen carbonate aqueous solution and a saturated sodium chloride aqueous solution, and dried over sodium sulfate. Then, the solvent was distilled off to obtain a colorless oily substance. The oily substance was purified by silica gel column chromatography, and 2.45 g of the above identified compound was obtained as a colorless viscous oily substance from the eluate with choroform-methanol (25:1, v/v).

NMR(CDCl$_3$)δ: 7.72, 7.27(each 2H, ABq), 7.60(1H, s), 5.5–4.9(2H, m), 4.44(1H, broad s), 4.2–3.8(3H, m), 3.7–3.1(2H, m), 2.42 (3H, s), 1.29(6H, d).

MS (m/e): 415(M$^+$), 373, 200, 158(100%).

EXAMPLE 13

4-Chloro-5-[3-(2-n-propyl-4-cyanothiophenoxy)-2-hydroxypropylamino]-2-i-propyl-3(2H)pyridazinone (Compound No. 153)

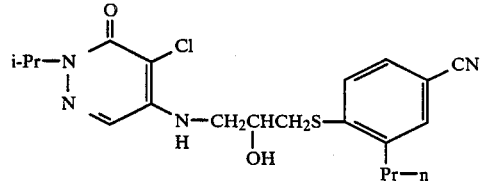

A mixture comprising 1.62 g of Compound No. 143 i.e. the tosyloxy product prepared in Example 12, 690 mg of 2-n-propyl-4-cyanothiophenol prepared in Reference Example 1-(vii), 585 mg of sodium iodide, 1.35 g of potassium carbonate and 40 ml of diethyl ketone, was refluxed under stirring for 18 hours. The solvent was distilled off, and water was added to the residue thereby obtained. The mixture was extracted with chloroform. The extract was washed sequentially with a 5% sodium hydroxide aqueous solution, water and a saturated sodium chloride aqueous solution, and dried over sodium sulfate. The solvent was distilled off t obtain a pale yellow oily substance. The oily substance was crystallized from a mixture of ethyl acetate-ethyl ether-benzene to obtain 1.12 g of the above identified compound as colorless crystals having a melting point of from 151.5° to 152.5° C.

NMR(CDCl$_3$+DMSO-d$_6$+D$_2$O):
7.67(1H, s), 7.34(3H, s), 5.5–4.9(1H, m), 4.3–3.1(5H, m), 2.69(2H, t), 1.9–1.2(2H, m), 1.28(6H, d), 0.98(3H, t).

MS (m/e): 420(M+), 343, 200, 177, 148(100%).

EXAMPLE 14

4-Chloro-5-[3-(2-n-propyl-4-carboxythiophenoxy)-2-hydroxypropylamino]-2-i-propyl-3(2H)pyridazinone (Compound No. 154)

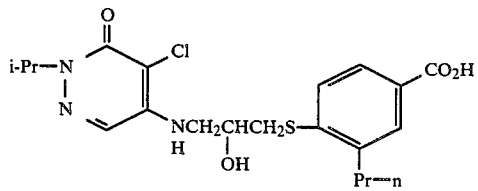

A mixture comprising 1.00 g of Compound No. 153 prepared in Example 13, 10 ml of 10N sodium hydroxide and 10 ml of methanol, was refluxed under stirring for 5.5 hours. Most methanol was distilled off, and the residue was acidified to a pH of about 2 by gradually adding concentrated hydrochloric acid under cooling with ice. The precipitated solid substance was collected by filtration. The solid substance was recrystallized from methanol-ethyl ether to obtain 950 mg of the above identified compound as colorless crystals having a melting point of from 174° to 174.5° C.

NMR(CDCl$_3$+DMSO-d$_6$+D$_2$O): 7.9–7.6(3H, m), 7.27(1H, d), 5.5–4.8(1H, m), 4.2–3.0(5H, m), 2.70(2H, t), 1.9–1.2(2H, m), 1.28(6H, d), 0.97(3H, t).

MS (m/e): 439(M+), 404, 362, 200(100%), 196, 167.
IR($\nu_{max}^{KBr}$)cm$^{-1}$: 3340, 3270, 1680, 1625(shoulder), 1600.

EXAMPLE 15

4-Chloro-5-[3-(2-n-propyl-4-methoxycarbonylthiophenoxy)-2-hydroxypropylamino]-2-i-propyl-3(2H)pyridazinone (Compound No. 155)

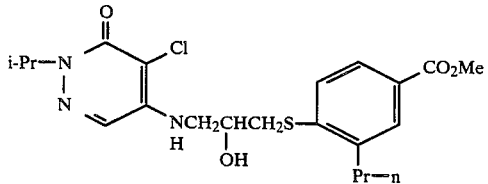

730 mg of Compound No. 154 prepared in Example 14 was dissolved in a mixture of 10 ml of methanol and 10 ml of ethyl acetate, and diazomethane gas was introduced thereto until the solution turned pale yellow. The reaction solution was left to stand overnight, and the solvent was distilled off. The residual solid substance thereby obtained, was subjected to silica gel column chromatography. The colorless crystals obtained from the eluate with benzene-ethyl acetate (1:1, v/v) were recrystallized from ethyl ether, n-hexane to obtain 420 mg of the above identified compound as colorless crystals having a melting point of from 155° to 156° C.

NMR(CDCl$_3$)δ: 7.9–7.7(2H, m), 7.68(1H, s), 7.33(1H, d), 5.4–4.8(2H, m), 4.2–3.0(6H, m), 3.88(3H, s), 2.76(2H, t), 1.9–1.3(2H, m), 1.30(6H, d), 1.00(3H, t).

MS (m/e): 453(M+), 418, 376, 210, 200(100%), 181.
IR($\nu_{max}^{KBr}$)cm$^{-1}$: 3340, 3280, 1710, 1630(shoulder), 1605.

EXAMPLE 16

4-Choloro-5-[3-(2-n-propyl-4-methoxycarbonyl-phenoxy)propyl-N-methylamino]-2-i-propyl-3(2H)pyridazinone (Compound No. 73)

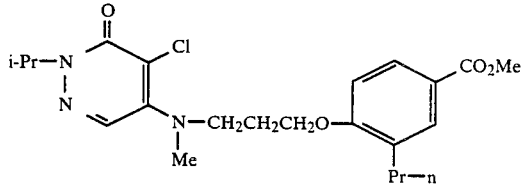

350 mg of 4-choloro-5-[3-(2-n-propyl-4-methoxycarbonylphenoxy)propylamino]-2-i-propyl-3(2H)pyridazinone (Compound No. 44) was dissolved in 20 ml of dried tetrahydrofuran, and 43 mg of sodium hydride (55% mineral oil suspension) and then 0.2 ml of methyl iodide were added under cooling with ice. The mixture was stirred for 15 minutes. Ice water was poured into the reaction mixture, and dilute hydrochloric acid was added to acidify the mixture to a pH of about 2. Then, the mixture was extracted with ethyl acetate. The extract was washed sequentially with water and a saturated sodium chloride aqueous solution, and dried over sodium sulfate. Then, solvent was distilled off to obtain 365 mg of the above identified compound as a pale yellowish orange viscous oily substance.

NMR(CDCl$_3$)δ: 7.9–7.7(2H, m), 7.63(1H, s), 6.75(1H, d), 5.28(1H, 7 heptaplet), 4.03(2H, t), 3.81(3H, s), 3.64(2H, t), 3.08(3H, s), 2.60(2H, t), 2.5–1.2(4H, m), 1.27(6H, d), 0.92(3H, t).

MS (m/e): 435(M+), 400, 214, 206(100%).

EXAMPLE 17

4-Chloro-5-[3-(2-n-propyl-4-cyanophenoxy)-2-methoxypropoxy]-2-i-propyl-3(2H)pyridazinone (Compound No. 172)

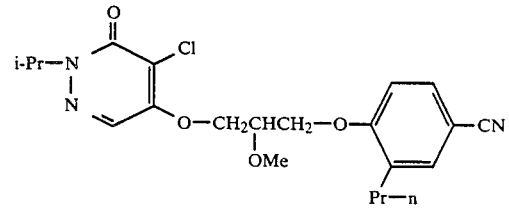

0.036 g of sodium hydride (55% mineral oil suspension) was added to a mixture comprising 300 mg of 4-chloro-5-[3-(2-n-propyl-4-cyanophenoxy)-2-hydroxypropoxy]-2-i-propyl-3(2H)pyridazinone (Compound No. 171) prepared in Example 11, 0.13 g of methyl iodide and 15 ml of tetrahydrofuran, under cooling with ice, and the mixture was stirred at room temperature for 2 hours. Then, 0.13 g of methyl iodide and 0.036 g of sodium hydride were further added thereto, and the mixture was stirred for 2 hours. Ice pieces were gradually added to the reaction solution under cooling with ice to decompose excess sodium hydride. Then, the reaction mixture was acidified with dilute hydrochloric acid, and tetrahydrofuran was distilled off under reduced pressure. The residue was extracted with ethyl acetate, and the extract was washed with water and dried over sodium sulfate. The solvent was distilled off, and the oily substance thereby obtained was isolated and purified by silica gel column chromatography (developer: benzene-ethyl acetate=2:1, v/v) to obtain 0.17 g of the above identified compound as a yellow oily substance.

NMR(CDCl$_3$)δ: 7.85(1H, d), 7.44(1H, dd), 7.37(1H, s), 6.87(1H, d), 5.54–5.51(1H, m), 4.43(2H, d), 4.21(2H, d), 4.34–3.84(1H, m), 3.55 (3H, s), 2.69(2H, t), 2.04–1.14(2H, m), 1.34(6H, d), 0.93(3H, t).

MS (m/e): 419(M+), 384, 189(100%).

EXAMPLE 18

4-Chloro-5-[3-(2-n-propyl-4-cyanophenoxy)-2-methoxypropyl-N-methylamino]-2-i-propyl-3(2H)pyridazinone (Compound No. 157)

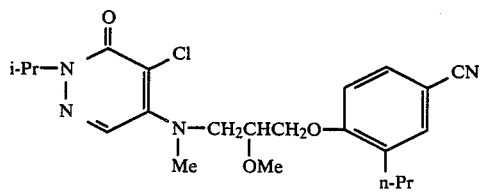

122 mg of 4-chloro-5-[3-(2-n-propyl-4-cyanophenoxy)-2-hydroxypropylamino]-2-i-propyl-3(2H)pyridazinone (Compound No. 145) was dissolved in 5 ml of dried tetrahydrofuran, and 30 mg of sodium hydride (55% mineral oil suspension) and then 0.2 ml of methyl iodide were added under stirring and cooling with ice. The mixture was stirred at 0° C. for 15 minutes. Ice water was poured into the reaction solution, and the mixture was extracted with ethyl acetate. The extract was washed with water and a saturated sodium chloride aqueous solution, and dried over sodium sulfate. Then, the solvent was distilled off to obtain a pale yellow oily substance. The oily substance was isolated and purified by silica gel column chromatography, and 69 mg of the above identified compound was obtained as a pale yellow viscous oily substance from the eluate with benzene-ethyl acetate (3:2, v/v).

NMR(CDCl$_3$)δ: 7.70(1H, s), 7.5–7.3(2H, m), 6.79(1H, d), 5.70(1H, 7 heptaplet), 4.1–3.2(5H, m), 3.43(3H, s), 3.18(3H, s), 2.58(2H, t), 1.9–1.3(2H, m), 1.30(6H, d), 0.94 (3H, t).

MS (m/e): 432(M+), 214(100%).

EXAMPLE 19

4-Chloro-5-[3-(2-n-propyl-4-cyanophenoxy)-2-methoxypropylamino]-2-i-propyl-3(2H)pyridazinone (Compound No. 158)

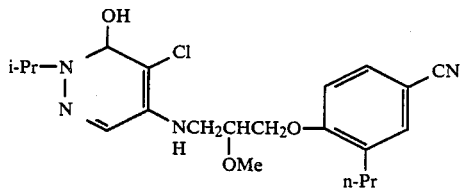

In the separation operation of the crude product by silica gel column chromatography in Example 18, the fraction eluated with a benzene-ethyl acetate (1:1, v/v) mixture following Compound No. 157 was obtained, and the solvent was distilled off from the fraction to obtain 35 mg of the above identified compound as a pale yellow viscous oily substance.

NMR(CDCl$_3$)δ: 7.65(1H, s), 7.6–7.3(2H, m), 6.84(1H, d), 5.5–4.8(2H, m), 4.2–3.3(5H, m), 3.50(3H, s), 2.60(2H, t), 2.0–1.3(2H, m), 1.30(6H, d), 0.96(3H, t).

MS (m/e): 418(M+), 383, 341, 200(100%), 161, 158, 132.

EXAMPLE 20

4-Chloro-5-{3-[4-(β-methoxycarbonyl-α-methylpropionyl)phenoxy]-2-methoxypropyl-N-methylamino}-2-i-propyl-3(2H)pyridazinone (Compound No. 167)

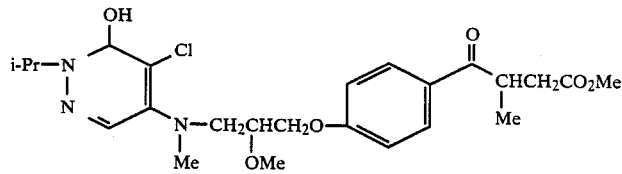

600 mg of 4-chloro-5-{3-[4-(β-methoxycarbonylpropyonyl)phenoxy]-2-hydroxypropylamino}-2-i-propyl-3(2H) pyridazinone (Compound No. 166) was dissolved in 10 ml of dried tetrahydrofuran, and 0.12 g of sodium hydride (55% mineral oil suspension) and then 0.47 g of methyl iodide were added under stirring and cooling with ice. The mixture was stirred for 1 hour on ice bath. Ice water was added to the reaction solution, and then dilute hydrochloric acid was added to bring the pH to about 7. Then, tetrahydrofuran was distilled off. Water was poured into the residue, and the mixture was extracted with ethyl acetate. The extract was washed sequentially with water and a saturated sodium chloride aqueous solution, and dried over sodium sulfate. Then, the solvent was distilled off to obtain a yellow oily substance. The oily substance was subjected to silica gel column chromatography, and 100 mg of the above identified compound was obtained as a pale yellow viscous oily substance from the eluate with benzene-ethyl acetate (1:1, v/v).

NMR(CDCl$_3$)δ: 7.92, 6.91(each 2H, ABq), 7.73(1H, s), 5.19(1H, 7 heptaplet), 4.2–2.4(8H, m), 3.60, 3.45, 3.18(each 3H, s), 1.28(6H, d), 1.20(3H, d).

MS (m/e): 494(M+1; 100%), 460.

EXAMPLE 21

4-Chloro-5-[3-(2-n-propyl-4-methoxycarbonylphenoxy)-2-oxopropylamino]-2-i-propyl-3(2H)pyridazinone (Compound No. 161)

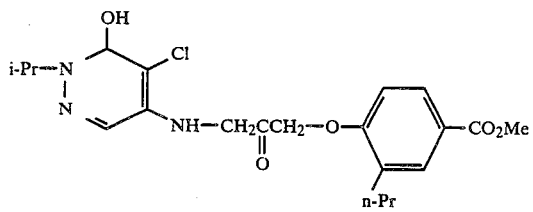

A mixture of 1.11 g of dimethylsulfoxide and 20 ml of tetrahydrofuran was cooled with dry ice-acetone, and a mixture of 2.24 g of trifluoroacetic anhydride and 3.67 ml of tetrahydrofuran, was gradually dropwise added thereto. The mixture was stirred for 20 minutes, and then a solution obtained by dissolving 0.93 g of 4-chloro-5-[3-(2-n-propyl-4-methoxycarbonylphenoxy)-2-hydroxypropylamino]-2-i-propyl-3(2H)pyridazinone (Compound No. 44) in 8 ml of tetrahydrofuran, was dropwise added thereto. The mixture was stirred for 30 minutes. Then, 1.26 g of triethylamine was dropwise added. Then, the mixture was stirred for 30 minutes under cooling with ice and then for 1 hour at room temperature. Sodium hydrogen carbonate was added thereto, and tetrahydrofuran was distilled off under reduced pressure. The residue was extracted with chloroform, and the extract was washed with water, and dried over sodium sulfate. Then, the solvent was distilled off, and the residue thereby obtained was purified by silica gel column chromatography by using benzene-ethyl acetate (1:1, v/v) as the developer. The solvent was distilled off, and the colorless crystals thereby obtained were further recrystallized from ethyl acetate-ethyl ether to obtain 0.52 g of the above identified compound as colorless crystals having a melting point of 133° C.

NMR(CDCl$_3$)δ: 8.09–7.74(2H, m), 7.43(1H, s), 6.72(1H, d), 5.71–4.99(2H, m), 4.77(2H, s), 4.53, 4.46(total 2H, each s), 3.85(3H, s), 2.72(2H, t), 2.09–1.49(2H, m), 1.30(6H, d), 1.01(3H, t).

MS (m/e): 435(M+), 392, 200, 165(100%).

EXAMPLE 22

5-[3-(2-n-propyl-4-ethoxycarbonylphenoxy)-propylamino]-2-i-propyl-3(2H)pyridazinone (Compound No. 63)

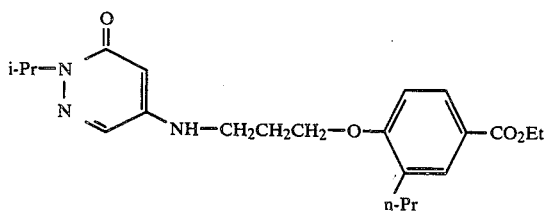

A mixture comprising 0.82 g of 4-chloro-5-[3-(2-n-propyl-4-ethoxycarbonylphenoxy)propylamino]-2-i-propyl-3(2H)pyridazinone (Compound No. 64), 50 ml of ethanol, 1.5 ml of triethylamine and 150 mg of 5% palladium-carbon was subjected to hydrogenation under stirring at a temperature of from 40° to 50° C. for 3 hours. The reaction mixture was filtered, and the filtrate was concentrated. The crude crystals thereby obtained were recrystallized from ethyl ether to obtain 0.58 g of the above identified compound as colorless crystals having a melting point of from 111° to 116° C.

NMR(CDCl$_3$)δ: 7.89–7.72(2H, m), 7.50(1H, d, J=3.0Hz), 6.75(1H, d), 5.97(1H, broad s), 5.63(1H, d, J=3.0Hz), 5.18(1H, m), 4.50–4.00(4H, m), 3.25(2H, t), 2.59(2H, t), 2.14(2H, t), 1.85–1.05(2H, m), 1.28(6H, d), 0.93(3H, t).

MS (m/e): 401(M+), 343, 194, 180, 167(100%), 152, 125.

EXAMPLE 23

4-Chloro-5-{3-[2-ethyl-4-(2-carboxyethenyl)phenoxy]-propylamino}-2-ethyl-3(2H)pyridazinone (Compound No. 93)

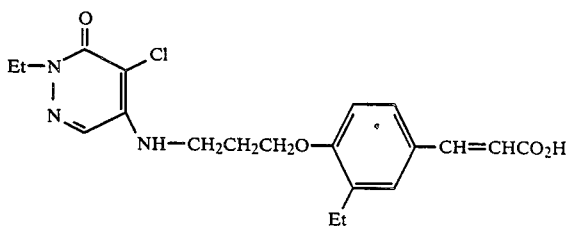

A mixture comprising 1.34 g of 4-chloro-5-[3-(2-ethyl-4-formylphenoxy)propylamino]-2-ethyl-3(2H) pyridazinone (Compound No. 92), 0.73 g of malonic acid, one drop of piperidine and 12 ml of pyridine, were heated under stirring at 100° C. for 3 hours. After cooling, the reaction solution was acidified with hydrochloric acid, and extracted with ethyl acetate. The extract was washed twice with water, and dried over sodium sulfate. Then, the solvent was distilled off, and the residue thereby obtained was crystallized from ethyl acetate-ethyl ether to obtain 1.2 g of the above identified compound as pale yellow crystals having a melting point of from 145° to 147° C.

NMR(CDCl$_3$)δ: 7.73(1H, s), 7.59(1H, d), 7.55–7.15(2H, m), 6.86(1H, d), 6.26(1H, d), 5.92(1H, broad s), 4.37–3.87(4H, m), 3.60(2H, q), 2.69(2H, q), 2.45–1.95(2H, m), 1.31(3H, t), 1.22(3H, t).

MS (m/e): 405(M+), 370, 187(100%).

EXAMPLE 24

4-Chloro-5-[3-(2-n-butyl-4-carbamoylphenoxy)-propylamino]-2-i-propyl-3-(2H)pyridazinone (Compound No. 114)

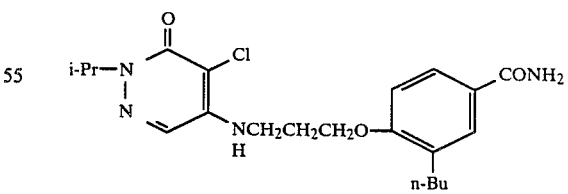

A mixture comprising 168 mg of 4-chloro-5-[3-(2-n-butyl-4-carboxyphenoxy)propylamino]-2-i-propyl-3(2H) pyridazinone (Compound No. 112), 119 mg of thionyl chloride and 10 ml of dried tetrahydrofuran, was refluxed under stirring for 1 hour. The reaction mixture was subjected to distillation under reduced pressure. To the residue, 20 ml of dried benzene was added. The mixture was again subjected to distillation under reduced pressure to remove excess thionyl chloride by azeotropic distillation. The residual oily substance thereby obtained, was dissolved in 10 ml of dried tetrahydrofuran, and ammonia gas was introduced thereinto for 5 minutes under cooling with ice. Then, the reaction solution was further stirred for 15 minutes. The reaction mixture was subjected to distillation under reduced pressure, and water was poured into the residue thereby obtained. The mixture was extracted with chloroform. The extract was washed sequentially with a 5% sodium hydroxide aqueous solution and a saturated sodium chloride aqueous solution, and dried over sodium sulfate. Then, the solvent was distilled off, and a pale yellow oily substance thereby obtained was crystallized from methanol-ethyl ether to obtain 143 mg of the above identified compound as colorless crystals having a melting point of 172° to 174° C.

NMR(CDCl$_3$+DMSO-d$_6$)δ: 7.8–7.5(3H, m), 6.79(1H, d), 7.0–6.1(2H, broad s), 5.5–4.9(2H, m), 4.11(2H, t), 3.8–3.3 (2H, m), 2.64(2H, t), 2.5–1.0(6H, m), 0.92(3H, collapsed t).

MS(m/e): 420(M+), 385, 368, 228, 214, 201(100%).

EXAMPLE 25

4-Bromo-5-[3-(2-n-butyl-4-cyanophenoxy)-propylamino]-2-ethyl-3(2H)pyridazinone (Compound No. 181)

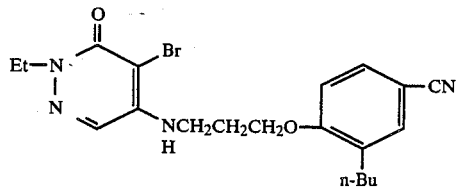

A mixture comprising 316 mg of 4-bromo-5-[3-(2-n-butyl-4-carbamoylphenoxy)propylamino]-2-ethyl-3(2H) pyridazinone (Compound No. 180), 174 mg of p-toluenesulfonyl chloride, 110 mg of pyridine and 5 ml of N,N-dimethylformamide, was stirred at 95° C. for 1.5 hours. The reaction mixture was subjected to distillation under reduced pressure. Water was poured into the residual oily substance, and the mixture was extracted with ethyl acetate. The extract was washed sequentially with 5% dilute hydrochloric acid, water and a saturated sodium hydrogen carbonate aqueous solution, and dried over sodium sulfate. Then, the solvent was distilled off to obtain a pale yellow oily substance. The oily substance was crystallized from ethyl ether to obtain 248 mg of the above identified compound as colorless crystals having a melting point of from 107.5° to 108.5° C.

NMR(CDCl$_3$)δ: 7.7–7.3(3H, m), 6.82(1H, d), 5.2–4.7(1H, m), 4.4–3.9(4H, m), 3.8–3.4(2H, m), 2.65(2H, broad t), 2.5–1.1(6H, m), 1.32(3H, t), 0.93(3H, collapsed t).

MS (m/e): 432(M+), 353(100%), 327, 258, 244, 231, 187.

EXAMPLE 26

Sodium salt of Compound No. 41 (Compound No. 67)

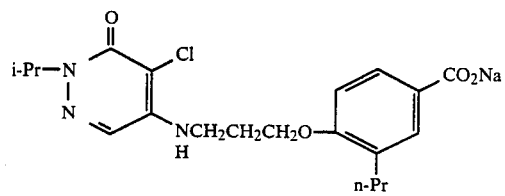

125 mg of 4-chloro-5-[3-(2-n-propyl-4-carboxy phenoxy)propylamino]-2-i-propyl-3(2H)pyridazinone (Compound No. 41) was dissolved in a mixture of 0.5 ml of a 2N sodium hydroxide aqueous solution and 2 ml of water, and subjected to adsorption column chromatography employing 30 cc of Amberlite XAD-8. The sample was adsorbed and washed with purified water until the washing solution became neutral, and then eluted with methanol. The solvent was distilled off under reduced pressure from the eluate, and the residue was treated with 30 ml of purified water, and then filtered. The aqueous solution thereby obtained was freeze-dried to obtain 72 mg of the above identified compound as a colorless powder.

MS(FD; m/e): 430(M+1).
IR($\nu_{max}^{KBr}$cm$^{-1}$): 3320, 1615.

EXAMPLE 27

4-Chloro-5-[3-(2-n-propyl-4-hydroxyphenoxy)-propylamino]-2-ethyl-3(2H)pyridazinone (Compound No. 108)

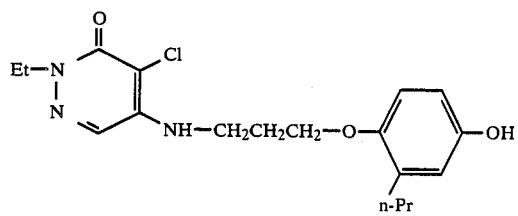

A solution obtained by dissolving 0.35 g of 4-chloro-5-[3-(2-n-propyl-4-methoxyphenoxy)propylamino]-2-ethyl-3(2H)pyridazinone (Compound No. 82) in 10 ml of methylene chloride, was dropwise added to a mixture comprising 0.36 g of aluminum chloride, 0.44 g of di-n-propylsulfide and 15 ml of methylene chloride, under stirring and cooling with ice. After the completion of the dropwise addition, the mixture was stirred at 0° C. for 2 hours, and then left to stand overnight in a refrigerator. Ice pieces were gradually added to the mixture to decompose excess aluminum chloride, and the mixture was extracted with chloroform. The extract was washed with water and dried over sodium sulfate. Then, the solvent was distilled off, and the residue thereby obtained, was crystallized from ethyl ether-n-hexane to obtain 0.26 g of the above identified compound as colorless crystals having a melting point of from 112° to 112.5° C.

NMR(CDCl$_3$)δ: 7.62(1H, s), 6.82–6.42(3H, m), 5.07(1H, broad s), 4.26(2H, q), 3.95(2H, q), 3.54(2H, q), 2.52(2H, t), 2.35–1.13(4H, m), 1.32(3H, t), 0.91(3H, t).

MS (m/e): 365(M+), 330, 214(100%), 186.

The compounds prepared in accordance with the above Examples are shown in Table 8. The process number indicated in the second column from the right hand side is the process number used for the preparation. Likewise, the Example No. in the right hand side end column is the Example No. in accordance with which the particular compound was prepared.

With respect to NMR(CDCl$_3$)δ, only characteristic absorptions were indicated. Likewise, as to MS, only the main peak and the maximum peak were indicated.

TABLE 8

Structure:

$R_1-N-N=$ ... with core pyridazinone-like ring bearing $R_2$, and $-A-CH_2XCH_2-B-$ phenyl($Y_1, Y_2, Y_3$)

| Compound No. | $R_1$ | $R_2$ | A | X | B | $Y_1$ | $Y_2$ | $Y_3$ | mp (°C.) | NMR (CDCl$_3$)δ | Process No. | Example No. |
|---|---|---|---|---|---|---|---|---|---|---|---|---|
| 1 | t-Bu | Cl | NH | CH$_2$ | O | 2-n-Pr | 4-CN | H | 96–97 | see Example 5 | 4 | 5 |
| 2 | t-Bu | Cl | NH | CH$_2$ | O | 2-n-Pr | 4-(N-N=/=N-N-H triazole) | H | 189–190 | see Example 6 | 6 | 6 |
| 3 | t-Bu | Cl | NH | CH$_2$ | O | 2-n-Pr | 4-CO$_2$Me | H | 107.5–108.5 | 7.49(1H, s), 4.74(1H, broad s), 4.09 (2H, t), 3.83(3H, s), 2.63(2H, t), 1.59(9H, s), 0.96(3H, t) | 4 | 5 |
| 4 | H | Cl | NH | CH$_2$ | O | 2-n-Pr | 4-CO$_2$Me | H | 164–166 | see Example 7 | 7 | 7 |
| 5 | t-Bu | Cl | NH | CH$_2$ | O | 2-n-Pr | 4-CO$_2$H | H | 199–199.5 | 7.51(1H, s), 4.71(1H, broad s), 4.62 (2H, t), 2.65(2H, t), 1.61(9H, s), 0.97(3H, t) | 9 | 9 |
| 6 | Et | Cl | NH | CH$_2$ | O | 2-n-Pr | 4-CO$_2$Me | H | Semi-solid substance | see Example 8 | 8 | 8 |
| 7 | Et | Cl | NH | CH$_2$ | O | 2-n-Pr | 4-CO$_2$H | H | 164–165 | see Example 9 | 9 | 9 |
| 8 | t-Bu | Cl | NH | CH$_2$ | O | 2-Cl | 4-CO$_2$Et | H | 122–123 | 7.61(1H, s), 4.82(1H, broad s), 4.22 (2H, q), 1.61(9H, s), 1.31(3H, t) | 4 | 5 |
| 9 | t-Bu | Cl | NH | CH$_2$ | O | 2-Cl | 4-CO$_2$H | H | 96 | 7.67(1H, s), 4.85(1H, broad s), 4.22 (2H, t), 1.61(9H, s) | 9 | 9 |
| 10 | Et | Cl | NH | CH$_2$ | O | 2-Cl | 4-CO$_2$Et | H | 93–95 | 7.68(1H, s), 4.95(1H, broad s), 1.38 (3H, t), 1.38(3H, t), 1.31(3H, t) | 9 | 9 |
| 11 | Et | Cl | NH | CH$_2$ | O | 2-Cl | 4-CO$_2$H | H | 180 | 7.75(1H, s), 6.20(1H, broad s), 1.28(3H, t) | 9 | 9 |
| 12 | Me | Cl | NH | CH$_2$ | O | 2-n-Pr | 4-CO$_2$H | H | 207–209 | (CDCl$_3$+DMSO-d$_6$): 7.58(1H, s), 5.58 (1H, broad s), 3.66(3H, s), 0.94(3H, t), 1.61(9H, s) | 9 | 9 |
| 13 | Et | Cl | NH | CH$_2$ | O | 2-Cl | 4-CO$_2$Me | H | 123–124 | 7.70(1H, s), 5.03(1H, broad s), 3.89(3H, s), 1.39(3H, t) | 4 | 5 |
| 14 | t-Bu | Cl | NH | CH$_2$ | S | 3-OMe | H | H | Viscous oily substance | 7.48(1H, s), 4.64(1H, broad s), 3.65(3H, s), 3.00(2H, t) | 4 | 5 |
| 15 | t-Bu | Cl | NH | CH$_2$ | OSO$_2$ | 4-Me | H | H | Viscous oily substance | see Example 4 | 5 | 4 |
| 16 | t-Bu | Cl | NH | — | — | — | 3,4-(OMe)$_2$ | H | 123.5–124.5 | 7.50(1H, s), 4.87(1H, broad s), 3.82 (6H, s), 2.86(2H, t), 1.62(9H, s) | 1 | 1 |
| 17 | Et | Cl | NH | CH$_2$ | OCO | 4-Cl | H | H | 125–126 | 7.88, 7.32(each 2H, ABq), 7.49(1H, s), 4.91(1H, broad s), 4.42(2H, t), 4.13 (2H, q), 3.47, 2.11(each 2H, m) | 5 | 5 |

TABLE 8-continued

![structure: pyridazinone with R1-N-N, R2, O, connected to phenyl via A-CH2XCH2-B with Y1, Y2, Y3 substituents]

| Compound No. | R1 | R2 | A | X | B | Y1 | Y2 | Y3 | mp (°C.) | NMR (CDCl3)δ | Process No. | Example No. |
|---|---|---|---|---|---|---|---|---|---|---|---|---|
| 18 | Et | Cl | NH | — | — | | 3,4-(OMe)2 | H | 111 | 7.55(1H, s), 4.90(1H, broad s), 4.17 (2H, q), 3.85(6H, s), 2.89(2H, t), 1.32(3H, t) | 1 | 1 |
| 19 | t-Bu | Cl | NH | — | — | 4-OMe | H | H | 77-78 | 7.51(1H, s), 4.87(1H, broad s), 3.77 ((3H, s), 2.86(2H, t), 1.61(9H, s) | 1 | 1 |
| 20 | Et | Cl | NH | — | — | 4-OMe | H | H | 135-135.5 | see Example 1 | 1 | 1 |
| 21 | t-Bu | Cl | NH | O | O | H | H | H | 123-125 | 7.84(1H, s), 4.55(2H, t), 4.38(2H, t), 1.65(9H, s) | 3 | 3 |
| 22 | t-Bu | Cl | O | CH2 | O | 4-Me | H | H | 97 | 7.79(1H, s), 4.40(2H, t), 4.13(2H, t), 2.27(2H, t), 1.63(9H, s) | 3 | 3 |
| 23 | t-Bu | Cl | O | CH2 | O | 2-n-Pr | 3,4- ○=⟨CO2Et⟩-O- | | Viscous oily substance | 8.01(1H, d, J=9.0Hz), 7.72(1H, s), 7.05(1H, d, J=9.0Hz), 6.90(1H, s), 4.65-4.20(6H, m), 2.88(2H, t), 2.40 (2H, t), 1.61(9H, t), 1.42(3H, t), 0.94(3H, t) | 2 | 2 |
| 24 | t-Bu | Cl | O | CH2 | O | 2-n-Pr | 3,4- ○=⟨CO2H⟩-O- | | 85-90 | 8.04(1H, d, J=9.0Hz), 7.82(1H, s), 7.28(1H, d, J=9.0Hz), 4.70-4.10(4H, m), 2.85(2H, t), 2.41(2H, t), 1.65(9H, s), 0.94(3H, t) | 9 | 9 |
| 25 | Et | Cl | O | CH2 | O | 2-n-Pr | 3,4- ○=⟨CO2Et⟩-O- | | 109-114 | 8.04(1H, d, J=9.0Hz), 7.80(1H, s), 7.05(1H, d, J=9.0Hz), 7.02(1H, s), 4.65-4.05(8H, m), 2.90(2H, t), 2.42(2H, t), 1.43(3H, t), 1.37(3H, t), 0.96(3H, t) | 2 | 2 |
| 26 | t-Bu | Et | O | CH2 | O | 2-n-Pr | 3,4- ○=⟨CO2Et⟩-O- | | 164-167 | 8.01(1H, d, J=9.0Hz), 7.70(1H, s), 7.01(1H, d, J=9.0Hz), 6.90(1H, s), 4.60-4.20(6H, m), 1.61(9H, s), 1.42(3H, t), 1.06(6H, t) | 2 | 2 |
| 27 | t-Bu | Cl | O | CH2 | O | 3-OMe | H | H | 58-59 | 7.74(1H, s), 4.38(2H, t), 4.12(2H, t), | 2 | 2 |

TABLE 8-continued

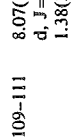

| Compound No. | $R_1$ | $R_2$ | A | X | B | $Y_1$ | $Y_2$ | $Y_3$ | mp (°C.) | NMR (CDCl$_3$)δ | Process No. | Example No. |
|---|---|---|---|---|---|---|---|---|---|---|---|---|
| 28 | Et | Cl | O | CH$_2$ | O | 3-OMe | H | H | 70-75 | 3.76(3H, s), 2.24(2H, t), 1.58(9H, s) 7.73(1H, s), 4.37(2H, t), 4.11(2H, t), 2.23 (2H, t), 3.75(3H, s), 2.41(2H, q), 1.37(3H, t) | 2 | 2 |
| 29 | Et | Cl | O | CH$_2$ | O | 2-n-Pr | ![structure] 3,4 | | 109-111 | 8.07(1H, d, J=9.0Hz), 8.87(1H, s), 7.08(1H, d, J=9.0Hz), 4.60-4.15(6H, m), 2.94(2H, t), 1.38(3H, t), 0.94(3H, t) | 9 | 9 |
| 30 | Et | Cl | O | CH$_2$ | O | 2-Cl | 4-CO$_2$Et | H | 101-103 | see Example 2 | 2 | 2 |
| 31 | Et | Cl | O | CH$_2$ | O | 2-Cl | 4-CO$_2$H | H | 182-184 | 7.80(1H, s), 4.51(2H, t), 4.20(2H, t), 1.37(3H, t) | 9 | 9 |
| 32 | t-Bu | Cl | O | CH$_2$ | O | 2-Cl | 4-CO$_2$Et | H | 69-71 | 7.85(1H, s), 4.41(2H, t), 4.53(2H, q), 4.32 (2H, t), 2.40(2H, t), 1.63(9H, s), 1.49(3H, t) | 2 | 2 |
| 33 | t-Bu | Cl | O | CH$_2$ | O | 2-Cl | 4-CO$_2$H | H | 141-144 | 9.70(1H, broad s), 7.79(1H, s), 4.38(2H, t) 4.28(2H, t), 2.38(2H, t), 1.61(9H, s) | 9 | 9 |
| 34 | t-Bu | Br | O | CH$_2$ | O | 3-OMe | H | H | 63.5-64.5 | 7.64(1H, s), 4.40(2H, t), 4.13(2H, t), 3.76 (3H, s), 2.29(2H, t), 1.64(9H, s) | 2 | 2 |
| 35 | i-Pr | Cl | O | CH$_2$ | O | 3-OMe | H | H | 81 | 7.82(1H, s), 5.30(1H, q), 4.40(2H, t), 4.12 (2H, t), 3.77(3H, s), 2.30(2H, t), 1.34(6H, d) | 2 | 2 |
| 36 | Et | Cl | O | (CH$_2$)$_2$ | O | 2-Br | H | H | Viscous oily substance | 7.78(1H, s), 4.50-3.97(4H, m), 3.76(2H, t) 1.93(4H, m), 1.37(3H, t) | 2 | 2 |
| 37 | t-Bu | Cl | O | CH$_2$ | O | 2-n-Pr | 3-OH | 4-Ac | Viscous oily substance | see Example 3 | 3 | 3 |
| 38 | t-Bu | Cl | O | — | — | H | H | H | 121 | 7.69(1H, s), 7.30(5H, s), 4.40(2H, s), 3.12(2H, t), 1.61(9H, s) | 1 | 1 |
| 39 | t-Bu | Et | O | — | — | 4-Cl | H | H | 130-131 | 7.69(1H, s), 7.30(4H, s), 4.41(2H, s), 3.11(2H, t), 1.62(9H, s) | 1 | 1 |
| 40 | t-Bu | Cl | O | CH$_2$ | — | H | H | H | Viscous oily substance | 7.70(1H, s), 4.20(2H, t), 2.88(2H, t), 2.18(2H, t), 1.66(9H, s) | 1 | 1 |
| 41 | i-Pr | Cl | NH | CH$_2$ | O | 2-n-Pr | 4-CO$_2$H | H | 197-198 | 7.66(1H, s), 4.23(2H, t), 1.39(6H, d), 0.95(3H, t) | 9 | 9 |
| 42 | i-Pr | Cl | NH | CH$_2$ | O | 2-n-Pr | 4-CONH$_2$ | H | 134-135 | see Example 10 | 10 | 10 |
| 43 | Me | Cl | NH | CH$_2$ | O | 2-n-Pr | 4-CO$_2$Me | H | 99-99.5 | 7.52(1H, s), 4.96(1H, broad s), 4.11 (2H, t), 3.83(3H, s), 3.69(3H, s), 2.64(2H, t), 0.95(3H, t) | 8 | 8 |
| 44 | i-Pr | Cl | NH | CH$_2$ | O | 2-n-Pr | 4-CO$_2$Me | H | 120.5 | 7.73(1H, s), 3.86(3H, s), 1.35(6H, d), 0.95(3H, t) | 8 | 8 |
| 45 | i-Pr | Cl | O | — | O | 3-OMe | H | H | Viscous oily | 7.58(1H, s), 5.25(1H, q), 3.80(3H, s), | 3 | 3 |

TABLE 8-continued

| Compound No. | R₁ | R₂ | A | X | B | Y₁ | Y₂ | Y₃ | mp (°C.) | NMR (CDCl₃)δ | Process No. | Example No. |
|---|---|---|---|---|---|---|---|---|---|---|---|---|
| 46 | t-Bu | Cl | O | CH₂ | O | 2-Cl | 4-CO₂Na | H | substance | 3.73(4H, s), 1.33(6H, d) | 9 | 26 |
| 47 | Et | Cl | NH | CH₂ | O | 2-n-Pr | 4-CN | H | 155–176 | 374(M⁺), 187(100%) | 4 | 5 |
| 48 | Et | Cl | NH | CH₂ | O | 2-n-Pr | 4-(N-N=N-NH) | H | 113–114 | 417(M⁺), 298(100%) | 6 | 6 |
|   |    |    |    |     |   |        | 207–208 |   |           |                  |   |   |
| 49 | Et | Cl | NH | CH₂ | O | 2-OMe | 4-CO₂Et | H | 134 | 409(M⁺), 186(100%) | 4 | 5 |
| 50 | Et | Cl | NH | CH₂ | O | 2-OMe | H | H | 84 | 337(M⁺), 186(100%) | 4 | 5 |
| 51 | Et | Cl | NH | CH₂ | O | 2-OEt | H | H | 100 | 352([M+H]⁺), 336(100%) | 4 | 5 |
| 52 | Et | Cl | NH | CH₂ | O | 2-OMe | 4-CO₂H | H | 143 | 381(M⁺), 186(100%) | 9 | 9 |
| 53 | Et | Cl | NH | CH₂ | O | 4-OEt | H | H | 95 | 351(M⁺), 214(100%) | 4 | 5 |
| 54 | Et | Cl | NH | CH₂ | O | 4-Me | H | H | 96–97 | 321(M⁺), 214(100%) | 4 | 5 |
| 55 | i-Pr | Cl | NH | — | O | 4-OMe | H | H | 98–99 | 321(M⁺), 122(100%) | 1 | 1 |
| 56 | Et | Cl | NH | CH₂ | O | 2-Me | H | H | 86–86.5 | 337(M⁺), 214(100%) | 4 | 5 |
| 57 | Et | Cl | NH | CH₂ | O | 2-Me | H | H | 84–88 | 321(M⁺), 286(100%) | 4 | 5 |
| 58 | i-Pr | Cl | NH | CH₂ | O | 4-OMe | H | H | Viscous oily substance | 351(M⁺), 186(100%) | 4 | 5 |
| 59 | i-Pr | Cl | NH | CH₂ | O | 2-OMe | H | H | 94 | 351(M⁺), 274(100%) | 4 | 5 |
| 60 | i-Pr | Cl | NH | CH₂ | O | 2-n-Pr | 4-CN | H | 121–123 | 388(M⁺), 311(100%) | 4 | 5 |
| 61 | i-Pr | Cl | NH | CH₂ | S | 2-n-Pr | 4-CN | H | 98–98.5 | 404(M⁺), 327(100%) | 4 | 5 |
| 62 | i-Pr | Cl | NH | CH₂ | S | 2-n-Pr | 4-CO₂H | H | 177.5–178 | 423(M⁺), 201(100%) | 9 | 9 |
| 63 | i-Pr | Cl | NH | CH₂ | O | 2-n-Pr | 4-CO₂Et | H | 115–116 | see Example 22 | 15 | 22 |
| 64 | i-Pr | Cl | NH | CH₂ | O | 2-n-Pr | 4-CN | H | 110–112 | 435(M⁺), 201(100%) | 4 | 5 |
| 65 | Et | Cl | O | CH₂ | O | 2-n-Pr | 4-CO₂Et | H | 90–91.5 | 375(M⁺), 175(100%) | 3 | 3 |
| 66 | i-Pr | Cl | NH | — | — | 2-n-Pr | 4-CN | H | 157–158 | 307(M⁺), 200(100%) | 1 | 1 |
| 67 | i-Pr | Cl | NH | CH₂ | O | 4-OH | 4-CO₂Na | H | Powder | see Example 26 | 9 | 26 |
| 68 | i-Pr | Cl | NH | CH₂ | S | 2-n-Pr | 4-(N-N=N-NH) | H | 189–191 | 447(M⁺), 143(100%) | 6 | 6 |
|   |     |    |    |     |   |         |         |   | 106 |             |   |   |
| 69 | i-Pr | Cl | NH | CH₂ | O | 2-Allyl | 4-CN | H | 185–188 | 387([M+H]⁺), 309(100%) | 4 | 5 |
| 70 | i-Pr | Cl | NH | CH₂ | O | 2-Allyl | 4-CO₂H | H |  | 405(M⁺, 100%) | 9 | 9 |

TABLE 8-continued $$R_1-N\underset{N}{\overset{O}{\bigvee}}\overset{R_2}{\underset{}{\bigvee}}A-CH_2XCH_2-B-\underset{Y_3}{\overset{Y_1}{\bigvee}}\overset{Y_2}{\underset{}{\bigvee}}$$

| Compound No. | R₁ | R₂ | A | X | B | Y₁ | Y₂ | Y₃ | mp (°C.) | NMR (CDCl₃)δ | Process No. | Example No. |
|---|---|---|---|---|---|---|---|---|---|---|---|---|
| 71 | i-Pr | Cl | NH | CH₂ | O | 2-OEt | H | H | 75 | 365(M⁺), 350(100%) | 4 | 5 |
| 72 | i-Pr | Cl | NH | CH₂ | O | 2-Me | H | H | 105-110 | 336([M+H]⁺), 258(100%) | 4 | 5 |
| 73 | i-Pr | Cl | NMe | CH₂ | O | 2-n-Pr | 4-CO₂Me | H | Viscous oily substance | see Example 16 | 12 | 16 |
| 74 | i-Pr | Cl | NMe | CH₂ | O | 2-n-Pr | 4-CO₂H | H | 158-159 | 421(M⁺), 206(100%) | 9 | 9 |
| 75 | i-Pr | Cl | NH | CH₂ | O | 4-C(=O)-(CH₂)₂CO₂H | H | H | 103-106 | 421(M⁺), 186(100%) | 9 | 9 |
| 76 | i-Pr | Cl | NH | CH₂ | O | 4-C(=O)-(CH₂)₂CO₂Me | H | H | Viscous oily substance | 435(M⁺), 361(100%) | 4 | 5 |
| 77 | i-Pr | Cl | NMe | CH₂ | O | 4-C(=O)-(CH₂)₂CO₂Me | H | H | Viscous oily substance | 449(M⁺), 206(100%) | 12 | 16 |
| 78 | i-Pr | Cl | NMe | CH₂ | O | 4-C(=O)-(CH₂)₂CO₂H | H | H | 113-115 | 435(M⁺), 417(100%) | 9 | 9 |
| 79 | i-Pr | Cl | O | CH₂ | O | 2-i-Pr | 4-CO₂Me | H | Viscous oily substance | 422(M⁺), 193(100%) | 4 | 5 |
| 80 | Et | Cl | NH | CH₂ | O | 2-Allyl | 4-CN | H | 128 | 372(M⁺), 337(100%) | 4 | 5 |
| 81 | Et | Cl | NH | CH₂ | O | 2-Allyl | 4-CO₂Me | H | Viscous oily substance | 405(M⁺), 370(100%) | 4 | 5 |
| 82 | Et | Cl | NH | CH₂ | O | 2-n-Pr | 4-OMe | H | 65-66 | 379(M⁺), 214(100%) | 4 | 5 |
| 83 | Et | Cl | O | CH₂ | O | 2-n-Pr | 4-CO₂H | H | 123-129 | 394(M⁺), 359(100%) | 9 | 9 |
| 84 | Et | Cl | O | CH₂ | O | 2-n-Pr | 4-CO₂Me | H | Viscous oily substance | 408(M⁺), 341(100%) | 3 | 3 |
| 85 | i-Pr | Cl | O | CH₂ | O | 2-n-Pr | 4-CO₂H | H | 62-63 | 422(M⁺), 387(100%) | 3 | 3 |
| 86 | i-Pr | Cl | O | CH₂ | O | 2-n-Pr | 4-CN | H | 171-172 | 408(M⁺), 373(100%) | 9 | 9 |
| 87 | i-Pr | Cl | O | CH₂ | O | 2-n-Pr | 4-CO₂Me | H | 88.5-89 | 389(M⁺), 354(100%) | 3 | 3 |
| 88 | i-Pr | Cl | NH | CH₂ | O | 2-i-Pr | 4-CN | H | 99-101 | 421(M⁺), 159(100%) | 4 | 5 |
| 89 | i-Pr | Cl | NH | CH₂ | O | 2-i-Pr | 4-CO₂H | H | 219-221 | 407(M⁺), 159(100%) | 9 | 9 |
| 90 | i-Pr | Cl | NH | CH₂ | O | 2-OEt | 4-CO₂Me | H | Viscous oily substance | 423(M⁺) | 4 | 5 |
| 91 | i-Pr | Cl | NH | CH₂ | O | 2-OEt | 4-CO₂H | H | 167-171 | 409(M⁺) | 9 | 9 |
| 92 | Et | Cl | NH | CH₂ | O | 2-Et | 4-CHO | H | Viscous oily substance | 363(M⁺), 187(100%) | 4 | 5 |

TABLE 8-continued $$\underset{R_1-N}{\overset{O}{\underset{N}{\bigvee}}}\underset{R_2}{\overset{}{\bigvee}}A-CH_2XCH_2-B\underset{}{\overset{Y_1}{\underset{Y_3}{\bigvee}}}Y_2$$

| Compound No. | $R_1$ | $R_2$ | A | X | B | $Y_1$ | $Y_2$ | $Y_3$ | mp (°C) | NMR (CDCl$_3$)δ | Process No. | Example No. |
|---|---|---|---|---|---|---|---|---|---|---|---|---|
| 93 | Et | Cl | NH | CH$_2$ | O | 2-Et | 4-CH=CHCO$_2$H | H | 145-147 | see Example 23 | 16 | 23 |
| 94 | i-Pr | Cl | NH | CH$_2$ | O | 2-Et | 4-CHO | H | 122-126 | 377(M$^+$), 342(100%) | 4 | 5 |
| 95 | i-Pr | Cl | NH | CH$_2$ | O | 2-Et | 4-CH=CHCO$_2$H | H | 150-151 | 419(M$^+$), 384(100%) | 16 | 23 |
| 96 | Et | Cl | NH | CH$_2$ | O | 2-Et | 4-CH=CHCO$_2$Me | H | Viscous oily substance | 393(M$^+$), 187(100%) | 4 | 5 |
| 97 | i-Pr | Cl | NH | CH$_2$ | O | 2-Et | 4-CO$_2$H | H | 178-180 | 393(M$^+$), 358(100%) | 9 | 9 |
| 98 | i-Pr | Cl | NH | CH$_2$ | O | 2-Et | 4-CN | H | 146-147.5 | 374(M$^+$), 297(100%) | 19 | 25 |
| 99 | Et | Cl | NH | CH$_2$ | O | 2-OMe | 4-Me | H | 111-113 | 351(M$^+$), 214(100%) | 4 | 5 |
| 100 | i-Pr | Cl | NH | CH$_2$ | O | 2-OMe | 4-Me | H | 125-126 | 365(M$^+$), 228(100%) | 4 | 5 |
| 101 | i-Pr. | Cl | NH | CH$_2$ | O | 2-Et | 4-CO$_2$Me | H | 107 | 407(M$^+$), 372(100%) | 4 | 5 |
| 102 | Et | Cl | NH | CH$_2$ | O | 2-Et | 4-CONH$_2$ | H | 156-157 | 392(M$^+$), 357(100%) | 10 | 10 |
| 103 | Et | Cl | NH | CH$_2$ | O | 2-i-Pr | 4-CONH$_2$ | H | 65-70 | 407(M$^+$), 187(100%) | 4 | 5 |
| 104 | i-Pr | Cl | NH | CH$_2$ | O | 2-i-Pr | 4-CO$_2$H | H | 157-158 | 393(M$^+$), 187(100%) | 9 | 9 |
| 105 | Et | Cl | NH | CH$_2$ | O | 2-n-Pr | 4-OMe | H | 94-97 | 393(M$^+$), 228(100%) | 4 | 5 |
| 106 | Et | Cl | NH | CH$_2$ | O | 2-Et | 4-OMe | H | Viscous oily substance | 365(M$^+$), 214(100%) | 4 | 5 |
| 107 | i-Pr | Cl | NH | CH$_2$ | O | 2-Et | 4-OMe | H | 112-113 | 379(M$^+$), 344(100%) | 4 | 5 |
| 108 | Et | Cl | NH | CH$_2$ | O | 2-n-Pr | 4-OH | H | 112-112.5 | see Example 27 | 17 | 27 |
| 109 | i-Pr | Cl | NH | CH$_2$ | O | 2-n-Pr | 4-OH | H | 127-128 | 379(M$^+$), 228(100%) | 17 | 27 |
| 110 | Et | Cl | NH | CH$_2$ | O | 2-n-Bu | 4-CO$_2$Me | H | 106-110 | 435(M$^+$), 400(100%) | 4 | 5 |
| 111 | Et | Cl | NH | CH$_2$ | O | 2-n-Bu | 4-CO$_2$H | H | 70-72 | 421(M$^+$), 187(100%) | 4 | 5 |
| 112 | i-Pr | Cl | NH | CH$_2$ | O | 2-n-Bu | 4-CO$_2$H | H | 198-199 | 421(M$^+$), 386(100%) | 9 | 9 |
| 113 | Et | Cl | NH | CH$_2$ | O | 2-n-Bu | 4-CONH$_2$ | H | 196-199 | 407(M$^+$), 187(100%) | 9 | 9 |
| 114 | i-Pr | Cl | NH | CH$_2$ | O | 2-n-Bu | 4-CONH$_2$ | H | 172-174 | see Example 24 | 10 | 24 |
| 115 | Et | Cl | NH | CH$_2$ | O | 2-n-Pr | 4-CN | H | 178-179 | 406(M$^+$), 187(100%) | 10 | 24 |
| 116 | Et | Br | NH | CH$_2$ | O | 2-Allyl | 4-CONH$_2$ | H | 113-115 | 418(M$^+$), 339(100%) | 4 | 5 |
| 117 | Et | Br | NH | CH$_2$ | O | 2-n-Pr | 4-CN | H | 124-126 | 418(M$^+$), 337(100%) | 4 | 5 |
| 118 | Et | Br | NH | CH$_2$ | O | 2-Allyl | 4-CO$_2$Me | H | 90-92 | 451(M$^+$), 372(100%) | 9 | 9 |
| 119 | Et | Br | NH | CH$_2$ | O | 2-n-Pr | 4-CO$_2$Me | H | 204-205 | 437(M$^+$), 358(100%) | 4 | 5 |
| 120 | Et | Br | NH | CH$_2$ | O | 2-n-Pr | 4-CN | H | 106-107 | 432(M$^+$), 311(100%) | 9 | 9 |
| 121 | i-Pr | Br | NH | CH$_2$ | O | 2-n-Pr | 4-CONH$_2$ | H | 180 | 436(M$^+$), 311(100%) | 4 | 5 |
| 122 | Et | Br | NH | CH$_2$ | O | 2-n-Pr | 4-CN | H | 129-130 | 450(M$^+$), 309(100%) | 10 | 24 |
| 123 | i-Pr | Br | NH | CH$_2$ | O | 2-Allyl | 4-CN | H | 127-128.5 | 432(M$^+$), 311(100%) | 10 | 24 |
| 124 | i-Pr | Br | NH | CH$_2$ | O | 2-n-Pr | 4-CO$_2$Me | H | 114.5-115 | 467(M$^+$), 386(100%) | 4 | 5 |
| 125 | i-Pr | Br | NH | CH$_2$ | O | 2-n-Bu | 4-CO$_2$H | H | 195-196 | 451(M$^+$), 372(100%) | 9 | 9 |
| 126 | i-Pr | Br | NH | CH$_2$ | O | 2-n-Bu | 4-CO$_2$Me | H | 105-108 | 479(M$^+$), 400(100%) | 4 | 5 |
| 127 | i-Pr | Br | NH | CH$_2$ | O | 2-n-Bu | 4-CO$_2$H | H | 192-194 | 465(M$^+$), 386(100%) | 9 | 9 |
| 128 | t-Bu | Cl | NH | CH$_2$ | O | 2-n-Pr | 4-CO$_2$H | H | Viscous oily substance | 410(M$^+$), 354(100%) | 4 | 5 |
| 129 | t-Bu | n-Pr | NH | CH$_2$ | O | 2-Cl | 4-CO$_2$Et | H | Viscous oily substance | 449(M$^+$), 358(100%) | 4 | 5 |
| 130 | H | n-Pr | NH | CH$_2$ | O | 2-Cl | 4-CO$_2$Et | H | 179-181 | 393(M$^+$), 180(100%) | 7 | 7 |

TABLE 8-continued structure: R1-NH-N=... with carbonyl, R2 group, A-CH2XCH2-B-phenyl(Y1,Y2,Y3)

| Compound No. | R1 | R2 | A | X | B | Y1 | Y2 | Y3 | mp (°C.) | NMR (CDCl3)δ | Process No. | Example No. |
|---|---|---|---|---|---|---|---|---|---|---|---|---|
| 131 | H | n-Pr | NH | CH2 | O | 2-n-Pr | 4-CO2Me | H | 185–187 | 387(M+), 180(100%) | 7 | 7 |
| 132 | H | n-Pr | NH | CH2 | O | 2-n-Pr | 4-CO2H | H | 186–188 | 373(M+), 180(100%) | 9 | 9 |
| 133 | Et | n-Pr | NH | CH2 | O | 2-n-Pr | 4-CO2Me | H | Viscous oily substance | 415(M+), 156(100%) | 8 | 8 |
| 134 | H | n-Pr | NH | CH2 | O | 2-Cl | 4-CO2H | H | 150–153 | 365(M+) | 9 | 9 |
| 135 | Et | Br | NH | CH2 | O | 2-n-Pr | 4-OMe | H | 75–79 | 423(M+), 344(100%) | 4 | 5 |
| 136 | i-Pr | Br | NH | CH2 | O | 2-n-Pr | 4-OMe | H | 96–98 | 439(M+), 358(100%) | 4 | 5 |
| 137 | Et | Br | NH | CH2 | O | 2-Et | 4-OMe | H | Semi-solid | 409(M+), 330(100%) | 4 | 5 |
| 138 | H | n-Bu | NH | CH2 | O | 2-n-Pr | 4-CO2Me | H | 140–142 | 401(M+), 152(100%) | 7 | 7 |
| 139 | H | n-Bu | NH | CH2 | O | 2-n-Pr | 4-CO2H | H | Semi-solid | 387(M+), 152(100%) | 9 | 9 |
| 140 | i-Pr | Cl | O | CH(OH) | O | 3-OMe | H | H | Viscous oily substance | 368(M+), 124(100%) | 11 | 11 |
| 141 | i-Pr | Cl | O | CH(OH) | O | 2-OEt | H | H | Viscous oily substance | 382(M+), 138(100%) | 11 | 11 |
| 142 | i-Pr | Cl | O | CH(OH) | O | 2-i-Pr | H | H | Viscous oily substance | 380(M+), 136(100%) | 11 | 11 |
| 143 | i-Pr | Cl | NH | CH(OH) | OSO2 | 4-Me | H | H | Viscous oily substance | see Example 12 | 5 | 12 |
| 144 | i-Pr | Cl | NH | CH(OH) | O | 2-n-Pr | H | H | 128–129 | 379(M+), 344(100%) | 4 | 13 |
| 145 | i-Pr | Cl | NH | CH(OH) | O | 2-n-Pr | 4-CN | H | 150.5–151 | 404(M+), 327(100%) | 4 | 13 |
| 146 | i-Pr | Cl | NH | CH(OH) | O | 2-n-Pr | 4-CO2H | H | 204.5–205.5 | 423(M+), 388(100%) | 9 | 9 |
| 147 | i-Pr | Cl | NH | CH(OH) | O | 2-n-Pr | 4-CO2Me | H | 129.5–130 | 437(M+; FD mass) | 4 | 13 |
| 148 | i-Pr | Cl | NH | CH(OH) | O | 2-n-Pr | 4-CONH2 | H | Powder | 423(M+), 200(100%) | 10 | 10 |
| 149 | Et | Cl | NH | CO | O | 2-n-Pr | 4-CN | H | 124–124.5 | 402(M+), 132(100%) | 14 | 21 |
| 150 | i-Pr | Cl | NH | CH(OH) | OSO2 | 4-Me | H | H | Powder | 401(M+), 186(100%) | 5 | 12 |
| 151 | i-Pr | Cl | NH | CH(OH) | O | 2-Cl | H | H | Viscous oily substance | 371(M+), 158(100%) | 4 | 13 |
| 152 | Et | Cl | NH | CH(OH) | O | 2-n-Pr | 4-OMe | H | Viscous oily substance | 395(M+), 166(100%) | 4 | 13 |
| 153 | i-Pr | Cl | NH | CH(OH) | S | 2-n-Pr | 4-CN | H | 151.5–152.5 | see Example 13 | 4 | 13 |
| 154 | i-Pr | Cl | NH | CH(OH) | S | 2-n-Pr | 4-CO2H | H | 174–174.5 | see Example 14 | 9 | 14 |
| 155 | i-Pr | Cl | NH | CH(OH) | S | 2-n-Pr | 4-CO2Me | H | 155–156 | see Example 15 | 18 | 15 |
| 156 | i-Pr | Cl | NH | CO | O | 2-n-Pr | 4-CO2Me | H | 102–105 | 451(M+), 210(100%) | 14 | 21 |
| 157 | i-Pr | Cl | NMe | CH(OMe) | O | 2-n-Pr | 4-CN | H | Viscous oily substance | see Example 18 | 12 | 18 |
| 158 | Et | Cl | NH | CH(OMe) | O | 2-n-Pr | 4-CN | H | Viscous oily substance | see Example 19 | 13 | 19 |
| 159 | Et | Cl | NH | CH(OH) | O | 2-Cl | H | H | 136–142 | 357(M+), 186(100%) | 4 | 13 |
| 160 | i-Pr | Cl | NH | CH(OH) | O | 2-n-Pr | 4-OMe | H | 112–114 | 409(M+), 166(100%) | 4 | 13 |
| 161 | i-Pr | Cl | NH | CO | O | 2-n-Pr | 4-CO2Me | H | 133 | see Example 21 | 14 | 21 |

TABLE 8-continued

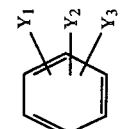
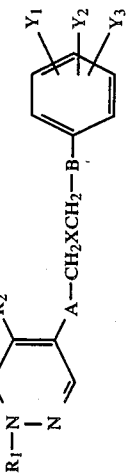

| Compound No. | R₁ | R₂ | A | X | B | Y₁ | Y₂ | Y₃ | mp (°C.) | NMR (CDCl₃)δ | Process No. | Example No. |
|---|---|---|---|---|---|---|---|---|---|---|---|---|
| 162 | i-Pr | Cl | NH | CH(OMe) | O | 2-n-Pr | 4-CO₂Me | H | Viscous oily substance | 451(M⁺), 200(100%) | 13 | 19 |
| 163 | i-Pr | Cl | NH | CH(OMe) | O | 2-n-Pr | 4-CO₂H | H | 173-174.5 | 437(M⁺), 200(100%) | 9 | 9 |
| 164 | i-Pr | Cl | NMe | CH(OMe) | O | 2-n-Pr | 4-CO₂Me | H | Viscous oily substance | 465(M⁺), 214(100%) | 12 | 18 |
| 165 | i-Pr | Cl | NMe | CH(OMe) | O | 2-n-Pr | 4-CO₂H | H | 165-168 | 451(M⁺), 214(100%) | 9 | 9 |
| 166 | i-Pr | Cl | NH | CH(OH) | O | 4-C(=O)—(CH₂)₂CO₂Me | H | H | Viscous oily substance | 451(M⁺), 121(100%) | 4 | 13 |
| 167 | i-Pr | Cl | NMe | CH(OMe) | O | 4-C(=O)—CH(Me)—CH₂CO₂Me | H | H | Viscous oily substance | see Example 20 | 12 | 20 |
| 168 | i-Pr | Cl | NMe | CH(OMe) | O | 4-C(=O)—CH(Me)—CH₂CO₂H | H | H | Viscous oily substance | 480(M⁺), 100%) | 9 | 9 |
| 169 | i-Pr | H | O | CH(OH) | O | 2-i-Pr | H | H | Viscous oily substance | 346(M⁺), 155(100%) | 15 | 22 |
| 170 | i-Pr | Cl | O | CH(OH) | NH | 3-OMe | 4-OMe | H | Viscous oily substance | 397(M⁺), 165(100%) | 4 | 4 |
| 171 | i-Pr | Cl | O | CH(OMe) | O | 2-n-Pr | 4-CN | H | 118.5-121 | see Example 11 | 11 | 11 |
| 172 | i-Pr | Cl | O | CH(OMe) | O | 2-n-Pr | 4-CN | H | Viscous oily substance | see Example 17 | 13 | 17 |
| 173 | i-Pr | Cl | O | CO | O | 2-n-Pr | 4-CO₂Me | H | 89-90 | 403(M⁺), 186(100%) | 14 | 21 |
| 174 | i-Pr | Cl | O | CH(OH) | O | 2-n-Pr | 4-CO₂Me | H | Viscous oily substance | 438(M⁺), 189(100%) | 11 | 11 |
| 175 | i-Pr | Cl | O | CH(OMe) | O | 2-n-Pr | 4-CO₂Me | H | Viscous oily substance | 452(M⁺), 189(100%) | 13 | 17 |
| 176 | H | n-Pen | NH | CH₂ | O | 2-n-Pr | 4-CO₂Me | H | Viscous oily substance | 411(M⁺) | 7 | 7 |
| 177 | i-Pr | Br | NH | CH₂ | O | Sec-Bu | 4-CO₂Me | H | 91-93 | 479(M⁺), 400(100%) | 4 | 5 |
| 178 | Et | Br | NH | CH₂ | O | 2-n-Bu | 4-CO₂Me | H | 97-100 | 465(M⁺), 386(100%) | 4 | 5 |
| 179 | Et | Br | NH | CH₂ | O | 2-n-Bu | 4-CO₂H | H | 200-201 | 451(M⁺), 372(100%) | 9 | 9 |
| 180 | Et | Br | NH | CH₂ | O | 2-n-Bu | 4-CONH₂ | H | 174-177 | 450(M⁺), 354(100%) | 10 | 24 |
| 181 | t-Bu | Br | NH | CH₂ | O | 2-n-Bu | 4-CN | H | 107.5-108.5 | see Example 25 | 19 | 25 |
| 182 | H | Br | NH | CH₂ | O | 2-n-Bu | 4-CO₂Me | H | 90 | 493(M⁺), 358(100%) | 4 | 5 |
| 183 | H | Br | NH | CH₂ | O | 2-n-Bu | 4-CO₂Me | H | 158-160 | 437(M⁺), 358(100%) | 7 | 7 |
| 184 | H | Br | NH | CH₂ | O | 2-n-Bu | 4-CO₂H | H | 109-110 | 423(M⁺), 326(100%) | 9 | 9 |

TABLE 8-continued

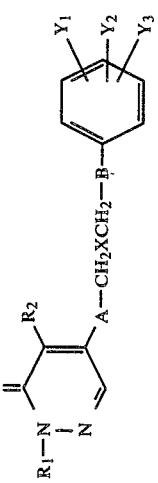

| Compound No. | R₁ | R₂ | A | X | B | Y₁ | Y₂ | Y₃ | mp (°C.) | NMR (CDCl₃)δ | Process No. | Example No. |
|---|---|---|---|---|---|---|---|---|---|---|---|---|
| 185 | t-Bu | Br | NH | CH₂ | OSO₂ | 4-Me | H | H | Viscous oily substance | 457(M⁺), 401(100%) | 5 | 4 |
| 186 | Et | Br | NH | CH₂ | OSO₂ | 4-Me | H | H | 115–117 | 429(100%, M⁺) | 5 | 4 |
| 187 | Et | Cl | NH | CH₂ | OSO₂ | 4-Me | H | H | 113–118 | 385(100%, M⁺) | 5 | 4 |
| 188 | i-Pr | Br | NH | CH₂ | OSO₂ | 4-Me | H | H | 99–100 | 443(M⁺), 401(100%) | 5 | 4 |
| 189 | i-Pr | Cl | NH | CH₂ | OSO₂ | 4-Me | H | H | 107–111 | 399(M⁺), 357(100%) | 5 | 4 |
| 190 | t-Bu | n-Bu | NH | CH₂ | O | 2-n-Pr | 4-CN | H | | 423(M⁺), 367(100%) | 4 | 5 |
| 191 | t-Bu | n-Pr | NH | CH₂ | OSO₂ | 4-Me | H | H | | 421(M⁺), 365(100%) | 5 | 4 |
| 192 | t-Bu | n-Bu | NH | CH₂ | OSO₂ | 4-Me | H | H | | 435(M⁺), 379(100%) | 5 | 4 |
| 193 | t-Bu | n-Pen | NH | CH₂ | OSO₂ | 4-Me | H | H | | 449(M⁺), 393(100%) | 5 | 4 |
| 194 | i-Pr | Br | NH | — | OSO₂ | 4-Me | H | H | 123–125 | 431(M⁺), 202(100%) | 4 | 5 |
| 195 | t-Bu | Br | NH | CH₂ | O | 2-C(=O)-n-Pr | 4-Br | H | Viscous oily substance | 528(M⁺), 150(100%) | 4 | 5 |
| 196 | H | Br | NH | CH₂ | O | 2-C(=O)-n-Pr | 4-Br | H | 63–65 | 471(M⁺), 150(100%) | 7 | 7 |
| 197 | Et | Br | NH | CH₂ | O | 2-n-Pr | 4-OH | H | 122–122.5 | 409(M⁺), 330(100%) | 17 | 27 |
| 198 | i-Pr | Br | NH | CH₂ | O | 2-n-Pr | 4-OH | H | 111–111.5 | 423(M⁺), 272(100%) | 17 | 27 |
| 199 | Et | Br | NH | CH₂ | O | 2-Et | 4-CHO | H | 106–107.5 | 407(M⁺), 328(100%) | 4 | 5 |
| 200 | i-Pr | Br | NH | CH₂ | O | 2-Et | 4-CHO | H | 115–116 | 421(M⁺), 300(100%) | 4 | 5 |
| 201 | Et | Cl | NH | CH₂ | O | 2-n-Pen | 4-CHO | H | 100–104 | 435(M⁺), 400(100%) | 4 | 5 |
| 202 | Et | Cl | NH | CH₂ | O | 2-n-Pen | 4-CO₂Me | H | 224.5–225.5 | 421(M⁺), 386(100%) | 9 | 9 |
| 203 | Et | Cl | NH | CH₂ | O | 2-n-Pen | 4-CONH₂ | H | 157.5–158.5 | 420(M⁺), 187(100%) | 10 | 24 |
| 204 | Et | Br | NH | CH₂ | O | 2-n-Pen | 4-CO₂Me | H | 93–95 | 479(M⁺), 400(100%) | 4 | 5 |
| 205 | Et | Br | NH | CH₂ | O | 2-n-Pen | 4-CO₂H | H | 211–211.5 | 465(M⁺), 386(100%) | 9 | 9 |
| 206 | Et | Br | NH | CH₂ | O | 2-n-Pen | 4-CONH₂ | H | 169–170 | 464(M⁺), 368(100%) | 10 | 24 |
| 207 | t-Bu | Br | NH | CH₂ | O | 2-n-Pen | 4-CO₂Me | H | 91–92 | 463(M⁺), 372(100%) | 4 | 5 |
| 208 | H | Cl | NH | CH₂ | O | 2-n-Pen | 4-CO₂Me | H | 157.5–158 | 407(M⁺), 372(100%) | 7 | 7 |
| 209 | H | Cl | NH | CH₂ | O | 2-n-Pen | 4-CO₂H | H | 161–163 | 393(M⁺), 158(100%) | 9 | 9 |
| 210 | t-Bu | Br | NH | CH₂ | O | 2-n-Pen | 4-CO₂Me | H | 80–80.5 | 507(M⁺), 372(100%) | 4 | 5 |
| 211 | H | Br | NH | CH₂ | O | 2-n-Pen | 4-CO₂Me | H | 153–154 | 451(M⁺), 372(100%) | 7 | 7 |
| 212 | H | Br | NH | CH₂ | O | 2-n-Pen | 4-CO₂H | H | 188–190 | 437(M⁺), 340(100%) | 9 | 9 |
| 213 | H | Br | NH | CH₂ | O | 2-n-Pen | 4-CONH₂ | H | 236–237.5 | 418(M⁺+H₂O), 339(100%) | 10 | 10 |

TABLE 8-continued
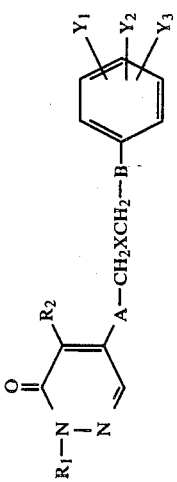
| Compound No. | R₁ | R₂ | A | X | B | Y₁ | Y₂ | Y₃ | mp (°C.) | NMR (CDCl₃)δ | Process No. | Example No. |
|---|---|---|---|---|---|---|---|---|---|---|---|---|
| 214 | t-Bu | n-Pen | NH | CH₂ | O | 2-n-Pr | 4-CN | H | Viscous oily substance | 437(M⁺), 381(100%) | 4 | 5 |
| 215 | i-Pr | Br | NH | — | O | 2-n-Pr | 4-CN | H | 127-129 | 420(M⁺), 297(100%) | 4 | 5 |
| 216 | i-Pr | Br | NH | CH₂ | O | 2-sec-Bu | 4-CO₂H | H | 204.5-205.5 | 465(M⁺), 386(100%) | 9 | 9 |
| 217 | Et | Br | NH | CH₂ | O | 2-sec-Bu | 4-CO₂Me | H | 61-63 | 465(M⁺), 386(100%) | 4 | 5 |
| 218 | Et | Br | NH | CH₂ | O | 2-sec-Bu | 4-CO₂H | H | 83-84 | 451(M⁺), 372(100%) | 9 | 9 |

Now, Formulation Examples of the compounds of the formula I will be given.

| FORMULATION EXAMPLES 1 and 2 (Tablets) | |
|---|---|
| Compound No. 6 (Formulation Example 1) or Compound No. 127 (Formulation Example 2) | 10 g |
| Lactose | 20 g |
| Starch | 4 g |
| Starch for paste | 1 g |
| Magnesium stearate | 100 mg |
| Carboxymethyl cellulose calcium | 7 g |
| Total | 42.1 g |

The above components were mixed in a usual manner, and formulated into sugar-coated tablets each containing 50 mg of an active ingredient.

| FORMULATION EXAMPLES 3 and 4 (Capsules) | |
|---|---|
| Compound No. 41 (Formulation Example 3) or Compound No. 122 (Formulation Example 4) | 10 g |
| Lactose | 20 g |
| Crystal cellulose powder | 10 g |
| Magnesium stearate | 1 g |
| Total | 41 g |

The above components were mixed in a usual manner, and filled into a gelatin capsule to obtain capsules each containing 50 mg of an active ingredient.

| FORMULATION EXAMPLES 5 and 6 (Soft capsules) | |
|---|---|
| Compound No. 7 (Formulation Example 5) or Compound No. 112 (Formulation Example 6) | 10 g |
| Corn oil | 35 g |
| Total | 45 g |

The above components were mixed in a usual manner to obtain soft capsules.

| FORMULATION EXAMPLES 7 and 8 (Ointment) | |
|---|---|
| Compound No. 98 (Formulation Example 7) Compound No. 117 (Formulation Example 8) | 1.0 g |
| Olive oil | 20 g |
| White vaseline | 79 g |
| Total | 100 g |

The above components were mixed in a usual manner to obtain 1% ointment.

| FORMULATION EXAMPLES 9 and 10 (Aerosol suspension) | |
|---|---|
| (A) Compound No. 6 (Formulation Example 9) or Compound No. 126 (Formulation Example 10) | 0.25 (%) |
| Isopropyl myristate | 0.10 |
| Ethanol | 26.40 |
| (B) A 60–40% mixture of 1,2-dichlorotetrafluoroethane and 1-chloropentafluoroethane | 73.25 |

The above composition (A) was mixed. The solution mixture thereby obtained was charged in a container equipped with a valve, and the propellant (B) was injected from a valve nozzle to a gauge pressure of from about 2.46 to 2.81 kg/cm² to obtain an aerosol suspension.

We claim:

1. A 3(2H)pyridazinone of the formula:

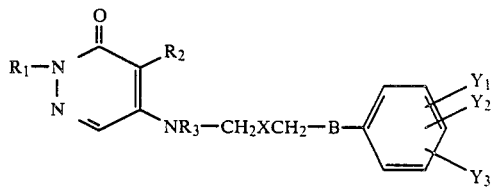

wherein $R_1$ is hydrogen or $C_1$-$C_5$ alkyl; $R_2$ is hydrogen, $C_1$-$C_8$ alkyl, chlorine or bromine; $R_3$ is hydrogen or $C_1$-$C_4$ alkyl; X is —$(CH_2)_n$—, wherein n is an integer of 1 to 4, —$CH(OH_4)$—, wherein $R_4$ is hydrogen or $C_1$-$C_4$ alkyl, —CO— or a single bond; when X is —$(CH_2)_n$—, wherein n is as defined above or a singel bond, B is —O—, —S—, —NH—, —$OSO_2$—, or —OCO— or a single bond; when X is —$CH(OR_4)$—, wherein $R_4$ is as defined above, B is —O—, —S—, —NH— or —$OSO_2$—; and when X is —CO—, is —O— or —S—; and each or $Y_1$, $Y_2$ and $Y_3$, which may be the same or different, is hydrogen, $C_1$-$C_8$ alkyl, $C_2$-$C_8$ alkenyl, halogen, —$OR_5$, wherein $R_5$ is hydrogen or $C_1$-$C_4$ alkyl, —$CO_2R_6$, wherein $R_6$ is hydrogen or $C_1$-$C_4$ alkyl, —$CH$=$CHCO_2R_7$, wherein $R_7$ is hydrogen or $C_1$-$C_4$ alkyl,

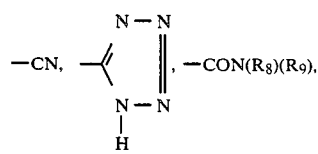

wherein each of $R_8$ an $R_9$, which may be the same or different, is hydrogen or $C_1$-$C_4$ alkyl, —$COR_{10}$, wherein $R_{10}$ is hydrogen, $C_1$-$C_5$ alkyl or

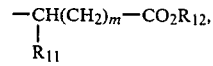

with m being an integer of 0 to 3, $R_{11}$ being hydrogen or $C_1$-$C_3$ alkyl, and $R_{12}$ being hydrogen or $C_1$-$C_4$ alkyl, or any two, of $Y_1$, $Y_2$ and $Y_3$ together forming

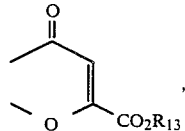

wherein $R_{13}$ is hydrogen or $C_1$-$C_4$ alkyl, provided that when $R_3$ is hydrogen and both X and B are single bonds, $Y_1$, $Y_2$ and $Y_3$ are not simultaneously hydrogen, and a pharmaceutically acceptable salt thereof.

2. The pyridazinone according to claim 1, wherein $R_2$ is $C_1$-$C_8$ alkyl, chlorine or bromine; when X is —$(CH_2)_n$—, wherein n is an integer of 1 to 4 or a single bond, B is —O—, —S—, —OCO— or a single bond; and when X is —$CH(OR_4)$, wherein $R_4$ is hydrogen or $C_1$-$C_4$ alkyl, or —CO—, B is —O— or —S—; $Y_1$ is hydrogen; and each of $Y_2$ and $Y_3$, which may be the same or different, is hydrogen, $C_1$-$C_8$ alkyl, $C_3$-$C_8$ alkenyl, halogen, —$OR_5$, wherein $R_5$ is hydrogen or $C_1$-$C_4$ alkyl, —$CO_2R_6$, wherein $R_6$ is hydrogen or $C_1$-$C_4$ alkyl, —$CH$=$CHCO_2R_7$, wherein $R_7$ is hydrogen or $C_1$-$C_4$ alkyl,

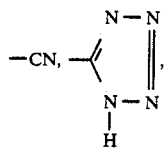

—CON(R$_8$)(R$_9$), wherein each of R$_8$ and R$_9$, which may be the same or different, is hydrogen or C$_1$-C$_4$ alkyl, —COR$_{10}$, wherein R$_{10}$ is hydrogen, C$_1$-C$_5$ alkyl or

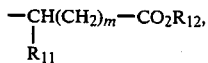

wherein m is an integer of 1 to 3, R$_{11}$ is hydrogen or C$_1$-C$_3$ alkyl, and R$_{12}$ is hydrogen or C$_1$-C$_4$ alkyl.

3. The pyridazinone according to claim 1, wherein R$_1$ is hydrogen or C$_1$-C$_4$ alkyl; R$_2$ is C$_1$-C$_6$ alkyl, chlorine or bromine; R$_3$ is hydrogen or methyl; X is —(CH$_2$)$_n$—, wherein n is an integer of 1 to 3, —CH(OR$_4$)—, wherein R$_4$ is hydrogen or C$_1$-C$_4$ alkyl or —CO—; when X is —(CH$_2$)$_n$, wherein n is as defined above, —CH(OR$_4$)—, wherein R$_4$ is as defined above or —CO—, B is —O— or —S—; Y$_1$ is hydrogen; and each of Y$_2$ and Y$_3$, which may be the same or different, is hydrogen, C$_1$-C$_8$ alkyl, C$_3$-C$_5$ alkenyl, halogen, —OR$_5$, wherein R$_5$ is hydrogen or C$_1$-C$_4$ alkyl, —CO$_2$R$_6$, wherein R$_6$ is hydrogen or C$_1$-C$_4$ alkyl,

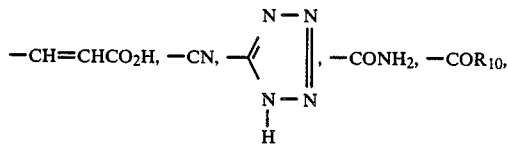

wherein R$_{10}$ is hydrogen, C$_1$-C$_5$ alkyl or

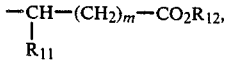

wherein R$_{11}$ is hydrogen or methyl, m is 0 to 1, and R$_{12}$ is hydrogen or methyl.

4. The pyridazinone according to claim 1, wherein R$_1$ is hydrogen or C$_1$-C$_4$ alkyl; R$_2$ is C$_1$-C$_6$ alkyl, chlorine or bromine; R$_3$ is hydrogen; X is —CH$_2$—, —CH(OR$_4$)—, wherein R$_4$ is hydrogen or methyl or —CO—; B is —O—; Y$_1$ is hydrogen; and each of Y$_2$ and Y$_3$ which may be the same or different, is C$_1$-C$_6$ alkyl, C$_3$-C$_5$ alkenyl, halogen, —OR$_5$, wherein R$_5$ is hydrogen, methyl or ethyl, —CO$_2$R$_6$, wherein R$_6$ is hydrogen, methyl or ethyl,

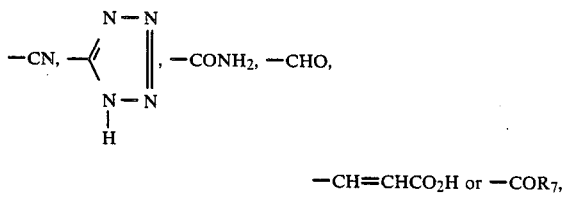

wherein R$_7$ is hydrogen or C$_1$-C$_5$ alkyl.

5. The pyridazinone according to claim 1, wherein R$_1$ is hydrogen, ethyl or i-propyl; R$_2$ is C$_1$-C$_4$ straight chain alkyl, chlorine or bromine; R$_3$ is hydrogen; X is —CH$_2$—, —CH(OR$_4$)—, wherein R$_4$ is hydrogen or methyl; B is —O—, Y$_1$ is hydrogen; and each of Y$_2$ and Y$_3$, which may be the same or different, is C$_2$-C$_5$ alkyl, alkyl, —OR$_5$, wherein R$_5$ is hydrogen or methyl, —CO$_2$R$_6$, wherein R$_6$ is hydrogen or methyl, —CN, —CONH$_2$ or —CHO.

6. The pyridazinone according to claim 1, which is 4-chloro-5-[3-(2-n-propyl-4-ethoxycarbonylphenoxy)-propylamino-2-i-propyl-3(2H) pyridazinone, 4-n-propyl-5-[3-(2-n-propyl-4-methoxycarbonylphenoxy)-propylamino]-2-ethyl-3(2H)pyridazinone, 4-chloro-5-[3-(2-ethyl-4-formylphenoxy)propylamino]-2-i-propyl-3(2H)pyridazinone, 4-chloro-5-[3-(2-ethyl-4-cyanophenoxy)propylamino-2-i-propyl-3(2H)pyridazinone, 4-chloro-5-[3-(2-ethyl-4-methoxycarbonylphenoxy)propylamino]-2-i-propyl-3(2H)pyridazinone, 4-chloro-5-[3-(2-n-propyl-4-methoxyphenoxy)propylamino]-2-i-propyl-3(2H)pyridazinone, 4-chloro-5-[3-(2-ethyl-4-methoxyphenoxy)propylamino]-2-ethyl-3(2H)pyridazinone, 4-chloro-5-[3-(2-ethyl-4-methoxyphenoxy)propylamino]-2-i-propyl-3(2H)pyridazinone, 4-chloro-5-[3-(2-n-propyl-4-hydroxyphenoxy)propylamino]-2-ethyl-3(2H)pyridazinone, 4-chloro-5-[3-(2-n-propyl-4-hydroxyphenoxy)propylamino]-2-i-propyl-3(2H)pyridazinone, 4-bromo-5-[3-(2-n-propyl-4-methoxyphenoxy)propylamino]-2-ethyl-3(2H)pyridazinone, 4-bromo-5-[3-(2-ethyl-4-methoxyphenoxy)propylamino]-2-ethyl-3(2H)pyridazinone, methoxy-carbonylphenoxy)propyl-2-ethyl-3(2H)pyridazinone, 4-chloro-5-[3-(2-n-propyl-4-cyanopyhenoxy)propoxy]-2-ethyl-3(2H)pyridazinone, 4-n-butyl-5-[3-(2-n-propyl-4-methoxycarbonylphenoxy)propylamino]-3(2H)pyridazinone, 4-chloro-5-[2-methoxy-3-(2-n-propyl-4-cyanophenoxy)proyylamino]-2-i-propyl-3(2H)pyridazinone, or 4-chloro-5-[2-hydroxy-3-(2-n-propyl-4-cynophenoxy)propylamino]-2-i-propyl-3(2H)pyridazinone.

7. The pyridazinone according to claim 1, which is 4-chloro-5-[3-(2-n-propyl-4-methoxycarbonylphenoxy)propylamino]-2-ethyl-3-(2H)pyridazinone.

8. The pyridazinone according to claim 1, which is 4-chloro-5-[3-(2-n-propyl-4-methoxycarbonylphenoxy)propylamino]-2-i-propyl-3(2H)pyridazinone.

9. The pyridazinone according to claim 1, which is 4-chloro-5-[3-(2-n-propyl-4-carboxyphenoxy)-propylamino]-2-i-propyl-3-(2H)pyridazinone.

10. The pyridazinone according to claim 1, which is 4-chloro-5-[3-(2-n propyl-4-carbamoylphenoxy)-propylamino]-2-i-propyl-3-(2H)pyridazinone.

11. The pyrdazinone according to claim 1, which is 4-chloro-5-[3-(2-allyl-4-cyanophenoxy)propylamino]-2-i-propyl-3(2H)pyridazinone.

12. The pyridazinone according to claim 1, which is 4-chloro-5-[3-(2-allyl-4-cyanophenoxy)propylamino]-2-ethyl-3(2H)pyridazinone.

13. The pyridazinone according to claim 1, which is 4-chloro-5-[3-(2-n-butyl-4-methoxycarbonylphenoxy)-propylamino]-2-ethyl-3(2H)pyridazinone.

14. The pyridazinone according to claim 1, which is 4-chloro-5-[3-(2-n-butyl-4-carboxyphenoxy)-propylamino]-2-i-propyl-3(2H)pyridazinone.

15. The pyridazinone according to claim 1, which is 4-chloro-5-[3-(2-n-butyl-4-carboxyphenoxy)-propylamino]-2-ethyl-3-(2H)pyridazinone.

16. The pyridazinone according to claim 1, which is 4-chloro-5-[3-2-n-butyl-4-carbamoylphenoxy)-propylamino]-2-i-propyl-3(2H)pyridazinone.

17. The pyridazinone according to claim 1, which is 4-chloro-5-[3-2-n-butyl-4-carbamoylphenoxy)-propylamino]-2ethyl-3(2H)pyridazinone.

18. The pyridazinone according to claim 1, which is 4-bromo-5-[3-(2-n-propyl-4-cyanophenoxy)-propylamino]-2-ethyl-3(2H)pyridazinone.

19. The pyridazinone according to claim 1, which is 4-bromo-5-[3-(2-allyl-4-cyanophenoxy)propylamino]-2--2-ethyl--3(2H)pyridazinone.

20. The pyridazinone according to claim 1, which is 4-bromo-5-[3-(2-n-propyl-4-methoxycarbonylphenoxy)propylamino]-2-ethyl-3(2H)pyridazinone.

21. The pyridazinone according to claim 1, which is 4-bromo-5-[3-(2-n-propyl-4-carbamoylphenoxy)-propylamino]-2-i-propyl-3(2H)pyidazinone.

22. The pyridazinone according to claim 1, which is 4-bromo-5-[3-(2-allyl-4-cyanophenoxy)propylamino]-2-i-propyl-3(2H)pyridazinone.

23. The pyridazinone according to claim 1, which is 4-bromo-5-[3-(2-n-propyl-4-methoxycarbonylphenoxy)propylamino]-2-i-propyl-3(2H)pyridazinone.

24. The pyridazinone according to claim 1, which is 4-bromo-5-[3-(2-n-propyl-4-carboxyphenoxy)-propylamino]-2-i-propyl-3(2H)pyridazinone.

25. The pyridazinone according to claim 1, which is 4-bromo-5-[3-(2-n-butyl-4-methoxycarbonylphenoxy)-propylamino]-2-i-propyl-3(2H)pyridazinone.

26. The pyridazinone according to claim 1, which is 4-bromo-5-[3-(2-n-butyl-4-carboxyphenoxy)-propylamino]-2-i-propyl-3-(2H)pyridazinone.

27. An anti-allergic agent, comprising:
   a pharmaceutically effective amount of a 3(2H)pyridazinone of formula 1 in claim 1 or a pharmaceutically acceptable salt thereof in combination with a pharmaceutically acceptable carrier.

28. A method of reducing the incidence or severity of allergy induced in a subject by SRS-A, which comprises:
   administering to said subject an amount of the 3 (2H)pyridazinone as defined in claim 1 which is effective in reducing the incidence or severity of said allergy or a pharmaceutically acceptable salt thereof to a subject suffering from said allergy.

29. The method of claim 28, wherein the 3(2H)pyridazinone compound is of formula (I) wherein $R_1$ is hydrogen, ethyl or i-propyl; $R_2$ is $C_1$–$C_4$ straight chain alkyl, chlorine or bromine; $R_3$ is hydrogen; X is —$CH_2$—, —$CH(OR_4)$—, wherein $R_4$ is hydrogen or methyl; B is —O—; $Y_1$ is hydrogen; and each of $Y_2$ and $Y_3$, which may be the same or different, is $C_2$–$C_5$ alkyl, allyl, —$OR_5$, wherein $R_5$ is hydrogen or methyl, —$COR_6$, wherein $R_6$ is hydrogen or methyl, —CN, —$CONH_2$ or —CHO.

* * * * *

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

Column 1, line 18: delete "a";

line 56: "(reference d)" should read -- (reference (d)) --.

Column 2, line 12: "0'" should read -- 0 --;

line 14: "(OR)" should read -- $(OR_4)$ --;

line 15: "(CH)" should read -- $(CH_2)$ --;

line 20: "$SO_2 13$" should read -- $SO_2-$ --;

line 20: "13 S" should read -- -S --;

line 22: "$C_2 14 C_8$" should read -- $C_2 - C_8$ --.

Column 3, line 8: "$C_1^\alpha C_8$" should read -- $C_1 - C_8$ --;

line 10: "hydrogenor" should read -- hydrogen or --;

line 56: after "formula", insert -- : --.

Column 5, line 14: "methoxycarobnylethylcarbonyl" should read -- methoxycarbonylethylcarbonyl --.

Column 6, line 25: "reation" should read -- reaction --;

line 54: "X" should read -- $X_1$ --.

UNITED STATES PATENT AND TRADEMARK OFFICE
CERTIFICATE OF CORRECTION

PATENT NO. : 4,783,462
DATED : NOVEMBER 8, 1988
INVENTOR(S) : Motoo MUTSUKADO et al It is certified that error appears in the above-identified patent and that said Letters Patent is hereby corrected as shown below:

Column 7, line 53: "X" should read -- $X_1$ --;

line 65: begin new paragraph at "The".

Column 8, line 22: change "(VO)" to -- (VI) --.

Column 9, line 9: change "methansul" to -- methanesul --.

Column 10, line 15: change "wherein R" to -- wherein $R_4$ --;

line 23: change "triethyleamine" to -- triethylamine --.

Column 11, line 39: change "pssible" to -- possible --.

Column 12, line 32: change "substituents susceptible" to -- substituent is susceptible --.

Column 13, line 39: change "he formula" to -- the formula --.

UNITED STATES PATENT AND TRADEMARK OFFICE
CERTIFICATE OF CORRECTION

PATENT NO. : 4,783,462
DATED : NOVEMBER 8, 1988
INVENTOR(S) : Motoo MUTSUKADO et al It is certified that error appears in the above-identified patent and that said Letters Patent is hereby corrected as shown below:

```
Column 14, line 12:   change "defiend" to -- defined --;

line 47:   change "isoation" to -- isolation --.

Column 15, line  2:   delete "-continued
                              Process 11".

Column 15, line 21:   below "(XXVIII)",
                      insert -- -continued
                              Process 11 --.

Column 17, line 24:   change "preferably a a"
                      to -- preferably at a --.

Column 18, line 53:   change "Jone's " to -- Jones --;

line 54:   change "Collin's" to
                      -- Collins --;

line 55:   change "dicyclohexylcarbodimide"
                      to -- dicyclohexylcarbodiimide --.

Column 19, line 37:   change "tratiing"
                      -- trating --.
```

UNITED STATES PATENT AND TRADEMARK OFFICE
CERTIFICATE OF CORRECTION

PATENT NO. : 4,783,462
DATED : NOVEMBER 8, 1988
INVENTOR(S) : Motoo MUTSUKADO et al It is certified that error appears in the above-identified patent and that said Letters Patent is hereby corrected as shown below:

Column 20, line 33: change "50°C." to -- 150°C. --;

line 35: change "reaciton" to -- reaction --.

Column 23, line 1: after "mine.", "Process" should start a new paragraph.

Column 26, line 10: change "such a" to -- such as --.

Column 29, line 25: after "wherein", insert -- $\ell$ --.

Column 30, line 62: under "$R_1$", change "iPr" to -- i-Pr --.

Column 33, line 1: change "methyl cellulose" to -- methylcellulose --;

line 2: change "carboxymethyl cellulose" to -- carboxymethylcellulose --;

line 10: change "propylene glycole" to -- propylene glycol --;

line 14: change "caster" to -- castor --;

line 16: change "methyl cellulose" to -- methylcellulose --;

line 27: change "bronchoconstiriction" to -- bronchoconstriction --.

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

| | |
|---|---|
| Column 34, line 64: | Table 3, at Test Compound No. 117, Antagonism (%), change "98" to -- 96 --. |
| Column 35, line 26: | change "incuated" to -- incubated --. |
| Column 36, line 26: | after "administration of", delete "the". |
| Column 38, line 31: | change "presen" to -- present --; |
| line 43: | change "a acetyl" to -- an acetyl --. |
| Column 39, line 4: | change "hydrogenchloride" to -- hydrogen chloride --; |
| line 54: | change "gal" to -- gel --. |
| Column 40, line 60: | change "a" to -- an --. |
| Column 41, line 16: | change "6.81(1h, d)" to -- 6.81 (1H, d) --. |
| Column 42, line 42: | change "prepare" to -- prepared --; |
| line 65: | change "exracted" to -- extracted --. |

UNITED STATES PATENT AND TRADEMARK OFFICE
CERTIFICATE OF CORRECTION

PATENT NO. : 4,783,462
DATED : NOVEMBER 8, 1988
INVENTOR(S) : Motoo MUTSUKADO et al It is certified that error appears in the above-identified patent and that said Letters Patent is hereby corrected as shown below:

Column 43, line 19: change "chromatograph" to -- chromatography --.

Column 44, line 22: change "only" to -- oily --;

line 45: change "shaked" to -- shaken --;

line 58: change "hydroxy2" to -- hydroxy-2 --.

Column 47, line 37: change "shaked" to -- shaken --;

line 40: change "was recrystallized" to -- were recrystallized --.

Column 49, line 24: change "shaked" to -- shaken --.

Column 52, line 20: after "3.84(3H,s)", insert -- , --.

Column 53, line 67: change "was" to -- were --.

Column 54, line 39: change "choroform" to -- chloroform --.

Column 55, line 2: change "off t" to -- off to --.

Column 56, line 11: change "Choloro" to -- Chloro --;

line 23: change "choloro" to -- chloro --.

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

Column 57, line 18:  change "cyanophanoxv" to -- cyanophenoxy --.

Column 58, line 7:  change "OH" to --  --;

line 38:  change "OH" to --  --;

line 46:  change "propyonyl" to -- propionyl --.

Column 59, line 7:  change "OH" to --  --.

Column 60, line 50:  change "3-(2H)" to -- 3(2H) --.

Column 62, line 26:  change "$V_{max}^{KBr} cm^{-1})$" to -- $V_{max}^{KBr}) cm^{-1}$ --;

line 13:  change "carboxy phenoxy" to -- carboxyphenoxy --;

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

Column 64, Table 8: under $Y_1$ and $Y_2$, Compound No. 16, it appears that "3,4-(OMe)$_2$" is indicated for $Y_2$ solely, instead of for both $Y_1$ and $Y_2$, as intended;

Table 8: under "Example No.", Compound No. 17, insert -- 4 --.

Column 65, Table 8: under "NMR", Compound No. 19, change "((3H,s)" to -- (3H,s) --;

Table 8: under "NMR", Compound No. 25, after "(8H,m)", insert -- , --.

Column 67, Table 8: under "NMR", Compound No. 33, after "4.38 (2H,t)", insert -- , --;

Table 8: under "Example No.", Compound No. 28, insert -- 2 --.

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

Column 68, Table 8: under headings "mp(°C.)" and "NMR (CDCl$_3$)δ", under bottom line, insert -- substance -- and -- 3.73(4H,s), 1.33(6H,d) -- respectively; and delete these two insertions from the top line of Column 69, Table 8;

Table 8: under "Example No.", Compound No. 34, insert -- 2 --.

Table 8: under "NMR", Compound No. 36, after "3.76 (2H,t)", insert -- , --;

Table 8: under "NMR", Compound No. 40, after "2.88 (2H,t)", insert -- , --;

Table 8: under "Example No.", Compound No. 41, insert -- 9 --.

Column 69, Table 8: change heading "NMR (CDCl$_3$)δ" to -- MS (m/e) --.

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

Column 83, line 11:     change "carboxymethyl cellulose" to -- carboxymethylcellulose --;

line 43:     before "Compound No. 117", insert -- or --;

line 61:     change "obtalned" to -- obtained --.

Column 84, line 13:     change "-CH(OH$_4$)-" to -- -CH(OR$_4$)- --;

line 15:     change "singel" to -- single --;

line 20:     change "or" (first occurrence) to -- of --;

line 34:     change "an" to -- and --.

Column 85, line 22:     after "rine", insert -- or bromine; R$_3$ is hydrogen or methyl; X is -(CH$_2$)$_n$-, --;

UNITED STATES PATENT AND TRADEMARK OFFICE
CERTIFICATE OF CORRECTION

PATENT NO. : 4,783,462
DATED : NOVEMBER 8, 1988
INVENTOR(S) : Motoo MUTSUKADO et al It is certified that error appears in the above-identified patent and that said Letters Patent is hereby corrected as shown below:

Column 86, line 5: change "alkyl" to -- allyl --;

line 22: please delete the extra print between the lines;

line 30: delete "methoxy-car-";

line 31: delete in its entirety;

line 32: delete in its entirety;

line 33: delete "ethyl-3(2H)pyridazinone";

line 37: change "proyylamino" to -- propylamino --;

line 39: change "cynophenoxy" to -- cyanophenoxy --;

line 43: change "3-(2H)" to -- 3(2H) --;

line 49: change "3-(2H)" to -- 3(2H) --;

line 51: change "n propyl" to -- n-propyl --;

line 52: change "3-(2H)" to -- 3(2H) --;

line 53: change "pyrdazinone" to -- pyridazinone --;

UNITED STATES PATENT AND TRADEMARK OFFICE
CERTIFICATE OF CORRECTION

PATENT NO. : 4,783,462

DATED : NOVEMBER 8, 1988

INVENTOR(S) : Motoo MUTSUKADO et al

It is certified that error appears in the above-identified patent and that said Letters Patent is hereby corrected as shown below:

```
Column 86, line 68:    change "3-(2H)" to -- 3(2H) --.

Column 87, line  2:    change "[3-2" to -- [3-(2 --;

line  5:    change "[3-2" to -- [3-(2 --;

line  6:    change "2ethyl" to -- 2-ethyl --;

line 12:    delete "2-" at end of line;

line 20:    change "pyidazinone"
                       to -- pyridazinone --.

Column 88, line  6:    change "3-(2H)" to -- 3(2H) --;

line  9:    change "1" (first occurrence)
                       to -- I --.
```

Signed and Sealed this

Sixteenth Day of June, 1992

Attest:

DOUGLAS B. COMER

*Attesting Officer*    Acting Commissioner of Patents and Trademarks